(12) United States Patent
Nakasuji et al.

(10) Patent No.: US 7,425,703 B2
(45) Date of Patent: Sep. 16, 2008

(54) ELECTRON BEAM APPARATUS, A DEVICE MANUFACTURING METHOD USING THE SAME APPARATUS, A PATTERN EVALUATION METHOD, A DEVICE MANUFACTURING METHOD USING THE SAME METHOD, AND A RESIST PATTERN OR PROCESSED WAFER EVALUATION METHOD

(75) Inventors: Mamoru Nakasuji, Kanagawa-ken (JP);
Tohru Satake, Kanagawa-ken (JP);
Nobuharu Noji, Kanagawa-ken (JP);
Takeshi Murakami, Tokyo (JP); Kenji Watanabe, Kanagawa-ken (JP);
Toshifumi Kimba, Kanagawa-ken (JP);
Kenichi Suematsu, Kanagawa-ken (JP)

(73) Assignee: Ebara Corporation, Tokyo (JP)

( * ) Notice: Subject to any disclaimer, the term of this patent is extended or adjusted under 35 U.S.C. 154(b) by 448 days.

(21) Appl. No.: 11/058,216

(22) Filed: Feb. 16, 2005

(65) Prior Publication Data
US 2005/0214958 A1    Sep. 29, 2005

(30) Foreign Application Priority Data

| Feb. 20, 2004 | (JP) | ............................. 2004-043800 |
| Mar. 2, 2004 | (JP) | ............................. 2004-057014 |
| Mar. 23, 2004 | (JP) | ............................. 2004-084006 |

(51) Int. Cl.
*G01N 23/225*    (2006.01)
(52) U.S. Cl. ....................................... 250/310; 313/455
(58) Field of Classification Search ................. 250/310
See application file for complete search history.

(56) References Cited

U.S. PATENT DOCUMENTS 3,628,014 A * 12/1971 Grubic, Jr. .................. 250/310

(Continued)

FOREIGN PATENT DOCUMENTS

JP            63-17523 A       1/1988

(Continued)

OTHER PUBLICATIONS

Y. Kumashiro et al., *Electron-Emission Characteristics and Surface States of Carbides Emitters—TiC Single Crystal and Other Transition Metal Carbides-*, Journal Applied Physics, vol. 45, No. 7, 1976, pp. 607-614.

(Continued)

*Primary Examiner*—David A. Vanore
*Assistant Examiner*—Phillip Johnston
(74) *Attorney, Agent, or Firm*—Westerman, Hattori, Daniels & Adrian, LLP.

(57) ABSTRACT

An object of the present invention is to provide an electron beam apparatus, in which a plurality of electron beams, e.g., four electron beams, is produced for one optical axis with a relatively high current achieved for each electron beam.

Provided is an electron beam apparatus comprising: an electron beam emitter (32) having an electron gun (30), said electron gun (30) disposed along an optical axis (23) and operable to emit a plurality of off-axis electron beams along a direction defined by a certain angle with respect to the optical axis (23); a plurality of apertures (34) disposed at a location offset from the optical axis (23); and an electromagnetic lens (7) for forming a magnetic field between the electron gun (30) and the apertures (34) to control the plurality of off-axis electron beams emitted from the electron gun (30) so that the plurality of off-axis electron beams passes through the apertures (34).

3 Claims, 32 Drawing Sheets

U.S. PATENT DOCUMENTS 4,091,311 A * 5/1978 Mendelsohn et al. ........ 315/382

FOREIGN PATENT DOCUMENTS

JP 7-249393 A 9/1995

OTHER PUBLICATIONS

Dr. Jayant Neogi, et al. "Next generation Electron Beam mask repair tool", Collection of Abstracts, NGL 2003, Jul. 10-11, 2003, pp. 129-130.

* cited by examiner (a)

(b)

$\Delta y_{51-52} = \Delta y_{52-53}$
$= \Delta y_{53-54} = \Delta y_{54-55}$
$= \Delta y_{55-56} = 1 \mu m$ $\Delta x_{51-52} = \Delta x_{52-53}$
$= \Delta x_{54-55} = \Delta x_{55-56}$
$= 0.3 \mu mm$ $x_{51} = x_{54}$

ELECTRON BEAM APPARATUS, A DEVICE MANUFACTURING METHOD USING THE SAME APPARATUS, A PATTERN EVALUATION METHOD, A DEVICE MANUFACTURING METHOD USING THE SAME METHOD, AND A RESIST PATTERN OR PROCESSED WAFER EVALUATION METHOD

BACKGROUND OF THE INVENTION

The present invention relates to an electron beam apparatus allowing for an evaluation of a substrate as large as 8 inches or 12 inches with high precision (50 nm pixel to 25 nm pixel) as well as high throughput. Using a multi-beam is advantageous to achieve the high throughput, and an electron gun with a greater intensity of angular current is required to obtain the highly intensified multi-beam from a single electron gun, which may be represented by the electron gun of $LaB_6$ and W hairpin having well-known angular current intensity values of $10^5$ μA/Sr and $3.93 \times 10^6$ μA/Sr, respectively.

It can be seen from the comparison in the values of specific angular current intensity that the value of $10^4$ μA/Sr for TaC is higher than 600 μA/Sr for ZrO/W but lower than $3.93 \times 10^6$ μA/sr for the W hairpin. The electron gun of TaC, however, emits intensive beams in the four different off-optical axial directions and this makes it easier to form the multi-beam. In this environment, the present invention is directed to an apparatus aimed at producing a multi-beam with a thermal electric field emission electron gun using a cathode made of TaC, for example, and also to a device manufacturing method which allows for the device to be manufactured with high yield by evaluating a wafer using the same electron beam apparatus.

In the background of this field of technology, for example, in regard to the emission of electrons from a carbide emitter of transition metal, Kumashiro, et al. have made a detailed report in their research paper, entitled "*Electron emission of carbide emitter and surface thereof*", on the electron emission characteristics in an emitter employing TaC single crystal and a polycrystalline thermal emitter (see, the journal, "*Applied physics*", Vol. 45, No. 7 (1976)).

As for the angular current intensity of the electron beam emitted from the thermal electric field emission electron gun, there are known values including, for example, $10^4$ μA/Sr for the TaC and 600 μA/Sr for the ZrO/W. The W hairpin has a problem that a beam current could not be so high.

There is a problem in an electron gun of the Schottky cathode made of ZrO/W, $LaB_6$ or carbide of transition metal that only a single beam along an optical axis has been used and inevitably a scanning operation with such a single beam consumes a lot of time.

Thus the present invention is directed to solve the above-described problem, or the problem that the long time is required to evaluate a large-sized substrate, such as an eight-inch wafer or a 12-inch wafer, with high precision (50 nm pixel to 25 nm pixel), and accordingly a first object of the present invention is to provide an electron beam apparatus allowing a number of electron beams, for example, four beams of electrons, to be produced for each optical axis yet with a relatively high current for every single beam of electrons.

The present invention further relates to an electron beam apparatus allowing for an image of a sample having a fine pattern to be taken with high resolution at a high rate.

In a practice to take a surface image of a sample, such as a wafer, according to the prior art, the sample surface is scanned with a narrowly converged electron beam and thus generated secondary electrons are detected to produce an SEM image for the purpose of enhancing the resolution of the image.

However, as the beam size is reduced, the beam current is also reduced in proportion to the fourth power of the dimension of beam diameter. To show one example, assuming that the pixel size is equal to the beam size, the following relations may be obtained:

| Beam size | Beam current | Pixel frequency | Frame time (sec) |
| --- | --- | --- | --- |
| 0.1 μmφ | 100 nA | 100 MHz | 1 sec/mm² |
| 0.05 μmφ | 6.25 nA | 6.25 MHz | 64 sec/mm² |
| 25 nmφ | 390 PA | 390 KHz | 4,096 sec/mm² |
| 10 nmφ | 10 PA | 10 KHz | $1 \times 10^6$ sec/mm² |

Accordingly, since the beam current is reduced exponentially in association with the reduction of the beam size, the beam current of the secondary electrons emanating from a sample, such as a wafer, is reduced, which makes it impossible to increase an S/N ratio of the image. Due to this, there has been no other choice than decreasing the scanning rate over the sample with the beam of primary electrons, or decreasing the pixel frequency exponentially, in order to increase the emission of the secondary electrons, and this has led to a problem that a considerably long time period, that is exponentially increased, is required to scan the image of a finite area.

Thus the present invention is also directed to solve the above-indicated problem, or the problem that if the beam size is reduced in order to take the surface image of the sample, such as the wafer, with high resolution, then more time is required to take the image, and accordingly a second object of the present invention is to provide an electron beam apparatus that allows for a beam of electrons having a certain beam size larger than the conventional beam size to be used for scanning the sample, that takes an image at a high rate based on the secondary electrons emanating from the sample and resultantly produces the image with high resolution.

The present invention further relates to an electron beam apparatus that carries out a defect inspection and a defect review of a sample having a fine pattern defined by a minimum line width not greater than 0.1 μm with high throughput and also to a device manufacturing method using the same electron beam apparatus.

This electron beam apparatus is applicable to improving a process condition and to classifying a defective wafer by specifying a factor in developing a defect of bad conductivity based on an inspection result of the sample from a defect detecting apparatus. Thus, it is required to acquire the state of the defect of bad conductivity precisely in order to specify the factor in developing the defect of bad conductivity, and to address this, confirming a high resolution image identifying a location of the defect of bad conductivity, or a bad conductivity defect review, may be useful.

Conventionally, a defect detecting apparatus needs a relatively high beam current due to its nature that a high throughput is required, and thus has employed an electron optical system with a compromise resolution performance. On the other hand, a defect reviewing apparatus has employed an electron optical system with a compromising level of beam current due to its nature that a high resolution is required. Thus, since those two apparatuses use respective beams that are different from each other, there has been almost no apparatus operable satisfactorily to provide the defect evaluation in both of the defect detection and the defect reviewing.

If both of the defect detecting apparatus and the defect reviewing apparatus are installed in a clean room, another problem would be encountered that a large floor area should be necessary. There would occur an additional problem of large time-loss because after the detection of the defect by the defect detecting apparatus, the detected defect has to be searched for in the separate defect reviewing apparatus.

Accordingly, a third object of the present invention is to provide an integrated apparatus that can provide the defect detection and the defect reviewing in a serial manner in a small foot print. Another object of the present invention is to provide a device manufacturing method using the same apparatus.

The present invention further relates to an electron beam apparatus, in which a primary electron beam is irradiated on a sample, and secondary electrons or the like emitting from the sample are formed into an image in a image-projection optical system to thereby form a sample image.

In a conventional electron beam apparatus employing the image projection optical system according to the prior art, the primary electron beam is incident upon the sample surface from an oblique direction with respect to a normal line of the sample and then deflected into a direction of the normal line by an E×B separator to irradiate the sample.

However, such an electron beam apparatus as described above has been had problems, including an increased chromatic aberration in a secondary electron beam caused by the E×B separator, a bad balance of a primary optical system that has been mounted obliquely, and an upper limit of irradiation dose imposed by a fact that the intensity and the emittance of the electron gun are finite and by a further fact that the secondary electron beam is blurred due to space charges from the primary electron beams.

Accordingly, a fourth object of the present invention is directed to solve the above-described problem and a goal thereof is to provide an electron beam apparatus that is free from the limited irradiation dose, the need for the primary optical system and the chromatic aberration of deflection possibly caused by the E×B separator.

The present invention further relates to an electron beam apparatus, and specifically to an electron beam apparatus equipped with a position measuring device for measuring a position of a sample table used in the electron beam apparatus that carries out an evaluation of a sample having a minimum line width not greater than 0.1 μm with high precision and high throughput.

Conventionally, an electron beam apparatus of the above-specified type has been equipped with a position measuring device for measuring a position of a sample table carrying a sample, such as a substrate, for the purpose of irradiating an electron beam to the sample precisely.

Such a position measuring device is operative in such a manner that a laser beam from a single laser oscillator is split into two beams, which are irradiated onto one laser mirror in parallel with x-axis and the other laser mirror in parallel with y-axis, respectively, wherein one laser beam is irradiated from the x-axis side onto the sample table, while the other laser beam is irradiated from the y-axis side onto the sample table so as to measure an irradiation point of an electron beam and the x- and y-directional positions of the sample table accurately.

It has been conventionally recognized that the sample table, during its movement, is subject to the Yaw motion to some extent depending on a tolerance of a stage operable to move the sample table. In the position measuring device of the prior art, in which both of the one laser beam irradiated from the x-axis side to the sample table and the other laser beam irradiated from the y-axis side to the sample table are directed to one and the same optical axis, any misalignment of the sample table slightly offset from an ideal position of the sample table resultant from its Yaw motion could not be a problem but is negligible, so far as only one optical axis is used. However, in the electron beam apparatus having a plurality of optical axes, specifically for a primary electron beam along an optical axis positioned differently from the laser axis along which the laser beam is irradiated, the misalignment would be no more neglected but would problematically induce what is called Abbe's error. Further, disadvantageously, there has been a problem that a movable mirror for the laser is greatly enlarged in size as the sample size becomes larger, and specifically in the case of a stationary mirror for the laser that has been fixedly mounted on a sidewall of a sample chamber, there has been another problem that a measurement error is induced due to an expansion and a contraction of the sidewall of the sample chamber.

Thus the present invention is also directed to solve the above-described problems, and accordingly, a fifth object thereof is to provide a position measuring device for a sample table used in an electron beam apparatus of high precision and high throughput, which eliminates the Abbe's error even in an apparatus having a plurality of optical axes. The present invention further provides an apparatus contemplated advantageously from the viewpoint of preventing growing in size of the sample table due to the movable laser mirror and for eliminating any measurement errors resultant from the expansion and contraction of the sidewall of the sample chamber.

The present invention further relates to a method for evaluating a sample having a pattern defined by a minimum line width not greater than 0.1 μm with high throughput and also to a method for manufacturing a device with high yield by using the same evaluation method.

To carry out a defect inspection of a semiconductor device, a CD (Critical Dimension) measurement and a pattern evaluation including a measurement of alignment accuracy, all by using an electron beam, a method has been conventionally suggested that a multi-beam be formed in a single optical system and a scanning operation be performed with said multi-beam so as to obtain a two-dimensional image.

However, such a technique has not yet been known in the prior art that small sized two-dimensional images obtained from a plurality of detectors corresponding to respective beams are joined together so as to produce a single large-sized image. In this arrangement, the evaluation has been performed as per each beam, and, inefficiently, this needs a complicated procedure.

Further, there has been suggested another technology according to the prior art for producing the multi-beam, in which electron beam emitted from a plurality of emitters are irradiated to apertures equally spaced from an optical axis so as to form a multi-beam.

However, owing to the features of this technology of the prior art characterized by a relatively large spacing between beams of the multi-beam, advantageously it is easier to detect secondary electrons independently, whereas the beams are located relatively distant from the optical axis, and this causes drawbacks including astigmatism and coma aberration in a primary electron beam, problematically inhibiting the primary beam from being converged to be narrow.

Further, in the conventional practice for the CD measurement or the alignment accuracy measurement, the electron beam is converged to be 10 nm or narrower and a thus narrowly converged electron beam is used to measure a line width or a line spacing, thus performing the measurement operation.

However, since a beam current is lower due to a smaller beam size inherent to the prior art, a scanning rate must be reduced in order to obtain a good S/N ratio and thus improve precision, which leads to another problem of the throughput being reduced.

There has been further suggested a method for evaluating a sample by scanning a sample surface with a plurality of beams, including a method using a multi-column and a method using an arrangement of a plurality of beams positioned along a circumference of a circle around an optical axis.

However, the method using the multi-column has a drawback that the throughput would not be improved distinctively since even with a wafer size as large as 12 inches, all that could be contemplated is simply to arrange some columns over the wafer, and at the same time this disadvantageously makes the whole apparatus expensive. Besides, in the method using an arrangement of the multi-beam positioned along the circumference of the circle, it is required to increase the diameter of the circle to generate more beams, and this would inversely intensify the effect of other aberrations than the curvature of field, including the astigmatism and the coma aberration, problematically inhibiting the beam from being converged to be narrow.

Accordingly, a sixth object of the present invention is to provide a method for producing a single large-sized two-dimensional image by joining together a plurality of small-sized two-dimensional images corresponding to a plurality of beams.

Further, a seventh object of the present invention is to provide a pattern evaluation method that is free from any obstacles in converging a primary beam to be narrower, and which can provide an efficient detection of secondary electrons without any cross talks among them.

Further, an eighth object of the present invention is to provide a method for performing a CD measurement and/or measuring an alignment accuracy with high throughput.

Further, a ninth object of the present invention is to provide a pattern evaluation method, in which a multi-beam is generated proximally to a single optical axis, and secondary electrons from respective beams in the concurrent scanning with those beams can be detected efficiently, yet using an electron optical system having a lesser number of lens stage.

The present invention further relates to an evaluation method for evaluating a resist pattern or a subsequently processed wafer, which enables highly accurate and quick evaluation of a lithography margin in a resist pattern written by an electron beam writer and/or in a resist pattern exposed by an ArF, $F_2$ excimer laser stepper.

Conventionally, a defect inspection apparatus employing a light has been used to evaluate the lithography margin or to determine whether or not an optical proximity effect is adequately compensated for. However, in the case where the writer of electron beam direct-writing type or the ArF, $F_2$ excimer laser stepper has been employed as the lithography apparatus, a size of a defect to be detected should be 100 nm or smaller, resulting in a problem of insufficient resolution of the defect inspection apparatus using the light.

In the light of the above problems, a defect inspection apparatus has been suggested that uses an electron beam instead of the light so as to enhance the resolution (see, for example, Patent Document 1 and 2).

[Patent Document 1]
Japanese Patent Laid-open Publication No. Sho 63-17523
[Patent Document 2]
Japanese Patent Laid-open Publication No. Hei 7-249393

Accordingly, a tenth object of the present invention is to provide an evaluation method for evaluating a resist pattern or a subsequently processed wafer, which allows for measurement of a lithography margin with high resolution in a short time with a defect inspection apparatus having a specific performance of minimum size of defect detection not greater than 100 nm.

SUMMARY OF THE INVENTION

To accomplish the first object described above, the present invention provides an electron beam apparatus comprising:

an electron beam emitter having an electron gun, said electron gun including a cathode disposed along an optical axis, and operable to emit a plurality of off-axis electron beams around said optical axis each along the direction defined by a certain angle with respect to said optical axis;

a plurality of apertures each disposed at a location out of said optical axis; and an electromagnetic lens for controlling an on-axis electron beam and said plurality of off-axis electron beams emitted from said electron gun so that said plurality of off-axis electron beams passes through said apertures.

According to the electron beam apparatus provided by the first invention of this patent application, owing to its configuration in which the on-axis electron beam and the off-axis electron beams emitted from the electron gun are controlled by the electromagnetic lens so that only the off-axis electron beams are permitted to pass through the apertures, advantageously it becomes possible to use the off-axis electron beams that have higher current than the on-axis electron beam in the inspection of the sample and thus to achieve a highly precise evaluation thereof. Further, since the plurality of electron beams can be used to scan and thus to inspect the sample surface, the present invention allows for the evaluation of the sample with high throughput.

To accomplish the second object described above, the present invention provides an electron beam apparatus comprising:

an electron beam source for emitting a primary electron beam;

a primary optical system for guiding said primary electron beam onto a sample surface so as to scan said sample with said primary electron beam;

a secondary electron detecting unit having a detection surface for detecting a secondary electron beam emitted from said sample; and a secondary optical system for guiding an image of said secondary electron beam emitted from said sample onto the detection surface of said secondary electron detecting unit to thus form a focused image, wherein said primary optical system comprises a converging lens operable to converge said primary electron beam emitted from said electron beam source to a size larger than a pixel size on said sample surface, and said secondary optical system comprises:
    a magnifying lens to magnify the image of said secondary electron beam emitted from said sample into the focused image on said detection surface; and
    an aperture disposed between said magnifying lens and said detection surface of said secondary electron detecting unit, and operable to selectively permit only the secondary electron beams that have been emitted from an area on the sample corresponding to the pixel size on said sample surface to pass therethrough from among the secondary electron beams that have been emitted from said sample and passed through said magnifying lens.

According to the second invention, since the primary electron beams having a beam size sufficiently larger than the pixel size on the detection surface of the secondary electron detecting unit are used to scan the sample surface, and only the specific portions of the secondary electron beams emitted from the sample that correspond to this pixel are exclusively permitted to enter the detection surface of the secondary electron beam detecting unit, advantageously the present invention brings about an effect that the image can be taken in high resolution at a high rate.

To accomplish the third object as described above, the present invention provides an electron beam apparatus comprising:

an electron gun;

a set of apertures for forming a plurality of primary electron beams for defect detection (hereafter referred to simply as an aperture for defect detection) for forming a primary electron beam emitted from said electron gun into a plurality of primary electron beams for defect detection to be used to perform a defect detection;

an aperture for forming at least one primary electron beam for defect reviewing (hereafter referred to as an aperture for defect reviewing) for forming a primary electron beam emitted from said electron gun into at least one primary electron beam for defect reviewing to be used to perform a defect reviewing;

said aperture for defect reviewing being smaller in size than said aperture for defect detection, thus allowing said primary electron beam for defect reviewing to be made narrower than said primary electron beam for defect detection;

an objective lens for reducing said primary electron beam for defect detection or said primary electron beam for defect reviewing transmitted through either one of said aperture for defect detection or said aperture for defect reviewing to be focused on a sample;

a separator for deflecting a secondary electron beam emitting from the sample; and a secondary electron detector for detecting the deflected secondary electron beam, wherein defect detection and defect reviewing are performed by selecting either of said aperture for defect detection or said aperture for defect reviewing and using either of said primary electron beam for defect detection or said primary electron beam for defect reviewing in association with said selected aperture.

Further, in said electron beam apparatus, said aperture for defect detection and said aperture for defect reviewing may be arranged in a single aperture plate.

Alternatively, in said electron beam apparatus, said aperture for defect detection and said aperture for defect reviewing may be arranged independently in separate aperture plates.

According to the third invention, owing to the configuration allowing for both of the defect reviewing and the defect detection of the sample to be performed in the same apparatus, an advantage of a successfully reduced foot print can be brought about. Further, this configuration can eliminate such time-consuming work that a defect is firstly detected in a defect detecting unit and then the detected defect is searched for in a separate defect reviewing device, thus advantageously reducing a loss-time and achieving the reduction in half of a loading and unloading time and a registration time of the sample.

To accomplish the fourth object as described above, the present invention provides an electron beam apparatus comprising:

an electron gun comprising a cathode in a ring configuration for emitting from its tip a primary electron beam composed of a hollow beam, and an anode and a Wehnelt for controlling a direction of said hollow beam emitted from said cathode; and a lens for converging said hollow beam emitted from said electron gun to be irradiated on the sample, wherein secondary electrons or back scattering electrons emitted from said sample are focused by said lens into an image.

Further, said electron beam apparatus may have a configuration, in which said anode has an inner anode that is grounded and an outer anode that is applied with a voltage, and said cathode is disposed in such a position that allows the primary electron beam to be incident upon the optical axis of the sample and the secondary electrons or the back scattering electrons emitting from said sample to be focused into the image by modifying a lens condition defining a focal distance of said lens and an irradiation condition in said electron gun defining an emission direction of the primary electron beam, wherein said lens condition of said lens can be controlled by changing a voltage applied to said lens, and said irradiation condition of said electron gun may be controlled by changing a voltage applied to said outer anode.

Further, said electron beam apparatus may have a configuration, in which, said lens comprises a multi-stage of lenses, and said electron gun is disposed between the lenses of said multi-stage of lenses.

To accomplish the fourth object as described above, the present invention provides an electron gun comprising:

a cathode in a ring configuration for emitting a primary electron beam composed of a hollow beam, and an anode and a Wehnelt for controlling a direction of said hollow beam emitted from said cathode, in which said cathode is made of cathode material that has been formed in a pipe shape and operable to emit a primary electron beam from its end surface by being heated from outside thereof, said anode has an inner anode and an outer anode, and said Wehnelt has an inner Wehnelt and an outer Wehnelt, wherein said inner anode and said inner Wehnelt are disposed on the inner side with respect to said cathode, and said outer anode and said outer Wehnelt are disposed on the outer side with respect to said cathode, wherein said inner anode and said outer anode are insulated from each other and an angle between said hollow beam and the optical axis can be adjusted by changing a potential difference between said inner anode and said outer anode, or by isolating said inner Wehnelt and said outer Wehnelt from each other and changing a potential difference between said inner Wehnelt and said outer Wehnelt.

According to the fourth invention, which has eliminated the E×B separator, advantageously the increase in chromatic aberration of the secondary electron beam due to the E×B separator can be prevented. Further, since the apparatus employs the electron gun comprising a ring-shaped cathode but the primary optical system is no more necessary, such a disadvantage as bad balance due to the oblique installation of the primary optical system can be avoided and thus stability can be ensured. Still further, since the electron gun comprising the ring-shaped cathode can emit an electron beam having high intensity and high emittance, allowing the primary electron beam to pass an outside of the secondary electron beam and thereby preventing any negative effect from the space charge effect, such an effect can be brought about that the dose of the electron beam is free from an upper limit.

To accomplish the fifth object as described above, the present invention provides a position measuring device for a sample table in an electron beam apparatus, said electron beam apparatus being adapted to perform an evaluation of a sample by irradiating a plurality of primary electron beams having a plurality of optical axes onto a sample carried on a sample table movable along an x-y plane having a x-axial direction and a y-axial direction, said position measuring device comprising:

a first measuring device operable to irradiate a first laser beam directed to the sample table along one of the x-axial direction and the y-axial direction for measuring a position of the sample table along said one of said axial directions;

a second measuring device operable to irradiate a second and a third laser beam directed to the sample table along the other of the x-axial direction and the y-axial direction for measuring two positions of the sample table along said other of said axial directions;

said second laser beams and said third laser beams being irradiated to said sample table along said other of said axial directions with an arrangement spaced apart from each other; and a controller for detecting a rotation of said sample table within the x-y plane based on a measurement from said first measuring device and a measurement from said second measuring device.

Said position measuring device may further comprise:

at least one laser source for radiating a laser beam; and a first splitting device for splitting the laser beam radiated from said laser source into at least two different laser beams, wherein said first measuring device uses one of said beams that have been split by said splitting means as said first laser beam, and said second measuring device may comprise a second splitting device for splitting the other of said beams that have been split by said first splitting means into said second and said third laser beams.

Further, said position measuring device may have a configuration, in which said first measuring device comprises a first reflecting mirror disposed along the other axial direction of said two axial directions of said sample table, a first guiding device for guiding said first laser beam that has been split in said first splitting device toward said first reflecting mirror and a first receiver for receiving said first laser beam that has been reflected on said first reflecting mirror;

said second measuring device comprises a second reflecting mirror disposed along said one axial direction of said two axial directions of said sample table; and said second splitting device has a second guiding device for guiding said second laser beam that has been split in said second splitting device toward said second reflecting mirror, wherein said second measuring device may further comprise:

a third guiding device for guiding said third laser beam that has been split in said second splitting device toward said second reflecting mirror;

a second receiver for receiving said second laser beam that has been reflected on said second reflecting mirror; and a third receiver for receiving said third laser beam that has been reflected on said second reflecting mirror.

Said position measuring device may have a configuration, in which said first measuring device further comprises a first stationary mirror installed on a sidewall of an objective lens in said electron beam apparatus disposed above said sample table, at a location on said sidewall defined in the first reflecting mirror side; and said first guiding device has a first beam splitter serving both for guiding said first laser beam that has been split in said first splitting device toward said first reflecting mirror and for splitting a fourth laser beam from said first laser beam, wherein said first measuring device may further comprise a first laser mirror for reflecting and irradiating said fourth laser beam toward said stationary mirror; and said second measuring device may further comprise:

a second stationary mirror installed on a sidewall of the objective lens in said electron beam apparatus, at a location on said sidewall defined in the second reflecting mirror side;

a second beam splitter serving both for guiding said second laser beam from said second guiding device toward said second reflecting mirror and for splitting a fifth laser beam from said second laser beam;

a second laser mirror for reflecting and irradiating said fifth laser beam toward said second stationary mirror;

a third beam splitter serving both for guiding said third laser beam from said third guiding device toward said second reflecting mirror and for splitting a sixth laser beam from said third laser beam; and a third laser mirror for reflecting and irradiating said sixth laser beam toward said second stationary mirror.

Further, to accomplish the fifth object as described above, the present invention provides an electron beam apparatus for evaluating a sample carried on a sample table movable along an x-y plane having the x-axial direction and the y-axial direction by irradiating a plurality of primary electron beams having a plurality of optical axes to said sample, said apparatus comprising:

a deflector for deflecting and irradiating said plurality of primary electron beams to said sample; and any one of said position measuring devices for the sample table as designated above, wherein said controller of said position measuring device controls said deflector based on a rotation within the x-y plane of said sample table, and said deflector, in response to said control, deflects each of said plurality of primary electron beams to compensate for any offset from an ideal course of movement of said sample and thus corrects the irradiation position of the primary electron beam on said sample.

Further, said electron beam apparatus may comprise:

an objective lens having said plurality of optical axes, which is disposed above said sample table, wherein said objective lens may be an electromagnetic lens in an integrated structure.

Further, in said position measuring device, said electron beam apparatus may comprise a plurality of optical systems for forming said plurality of primary electron beams, wherein each of said plurality of optical systems may have an objective lens having a plurality of optical axes, which is disposed above said sample table.

Further, in said position measuring device, each of said plurality of optical systems may be adapted to irradiate a plurality of primary electron beams across said sample.

According to the fifth invention, the configuration enables the measurement at two locations in the sample table along at least one axial direction of the x-axial direction and the y-axial direction in order to detect the rotation within the x-y plane of the sample table, thus an accurate sample evaluation can be provided, even if the sample table is driven into the Yaw motion. Further, eight of optical axes, if provided, can make the evaluation rate as much as eight times as high as that with a single beam. Therefore, the fifth invention can bring about an effect that the evaluation of the sample can be provided with high precision and high throughput.

To accomplish the sixth object as described above, the present invention provides a first pattern evaluation method, in which a plurality of beams is irradiated onto a sample for evaluating a pattern, said method comprising the steps of:

a. irradiating an electron beam emitted from an electron gun over a plurality of apertures;

b. forming reduced images of respective apertures on a sample surface;

c. scanning with said formed images of plurality of beams to obtain a plurality of two-dimensional images, one for each beam;

d. producing a single large-sized two-dimensional image by joining together said plurality of two-dimensional images obtained independently for respective beams;

e. measuring a space along one axial direction between beams of said plurality of beams; and f. adjusting said space to be an integer multiple of a pixel size.

In the above method, since the plurality of beams is used and the spacing between beams along one axial direction is adjusted to meet the integer multiple of the pixel size in order to form the large-sized two-dimensional image by joining together the two-dimensional images obtained by respective beams, it becomes possible to make an accurate operation of joining images between a small-sized two-dimensional image obtained by the scanning with one beam and another small-sized two-dimensional image obtained by the scanning with an adjacent beam and thus to achieve the pattern evaluation of high precision.

Further, to accomplish the sixth object as described above, the present invention provides a second pattern evaluation method, in which a plurality of beams is irradiated onto a sample to evaluate a pattern, said method comprising the steps of:

a. irradiating an electron beam emitted from an electron gun over a plurality of apertures;

b. forming reduced images of respective apertures on a sample surface;

c. scanning with said formed images of plurality of beams along one axial direction by a width of a stripe to obtain a two-dimensional image; and d. during obtaining said two-dimensional image in step (c), moving the sample table continuously in the other axial direction, suspending said movement in the other direction upon reaching a terminal end of a region to be evaluated, and step-moving a stage in said one axial direction by a width of a stripe, wherein an interface between said stripes has concavity and convexity corresponding to the positions of said plurality of beams along said one axial direction.

According to the above method, since in the evaluation of the pattern with a plurality of beams, the evaluation is provided for each stripe with the plurality of beams, wherein the interface between one stripe and another defines concavity and convexity corresponding to the positions of the plurality of beams along the one axial direction, therefore this manner can eliminate any duplicated or skipped scanning but provide an efficient evaluation with a plurality of beams.

Further, to accomplish the sixth object as described above, the present invention provides a third pattern evaluation method, in which a plurality of beams is irradiated onto a sample to evaluate a pattern, said method comprising the steps of:

a. irradiating an electron beam emitted from an electron gun over a plurality of apertures;

b. forming reduced images of respective apertures on a sample surface;

c. scanning with said formed images of plurality of beams along one axial direction to obtain a plurality of two-dimensional images by signals from detectors, each associated with one beam;

d. moving the position of said two-dimensional image by a predetermined distance both in the x-axial direction and the y-axial direction between respective beams on the sample to thereby join said two-dimensional images to be formed into a single two-dimensional image encompassing a larger area.

According to the above method, since in the evaluation of the pattern with a plurality of beams, the position of the small-sized two-dimensional image obtained from each beam is shifted by the predetermined distances along both of the x-axis and the y-axis between the beams on the sample for joining the images, therefore it becomes possible to obtain the resultant large-sized two-dimensional image formed by joining together all of the small-sized two-dimensional images obtained from the plurality of beams.

Further, to accomplish the sixth object as described above, the present invention provides a fourth pattern evaluation method, in which a plurality of beams is irradiated onto a sample to evaluate a pattern, said method comprising the steps of:

a. generating a plurality of beams;

b. scanning with a plurality of beams across a mark having an x-directional patterned side or a y-directional patterned side and detecting generated electrons from respective beams by detectors, each associated with one beam, so as to form a plurality of two-dimensional images;

c. joining together said plurality of two-dimensional images from respective detectors based on a predetermined value of inter-beam distance;

d. modifying the inter-beam distance to produce a normal geometry of the mark image that has been obtained in the joining step, re-joining the images, and then storing a particular inter-beam distance that can produce a most normal mark image; and e. obtaining a plurality of two-dimensional images of the sample to be evaluated by respective beams and joining together said plurality of two-dimensional images obtained from respective beams by using said stored value of the inter-beam distance so as to obtain a single two-dimensional image encompassing a larger area of the sample.

According to the method as described above, since in forming a large-sized two-dimensional image by joining together a plurality of small-sized two-dimensional images obtained from respective beams, not only the position of the small-sized two-dimensional image is shifted by the predetermined distance along both of the x- and the y-axial directions between the beams on the sample for joining the images, but also the inter-beam distance is modified for joining images to thereby compensate for the actual offset so as to create the normal geometry of the mark image to be obtained by joining, therefore it becomes possible to obtain the resultant large-sized two-dimensional image of high precision.

Further, to accomplish the seventh object as described above, the present invention provides a fifth pattern evaluation method, in which a pattern formed on a substrate is scanned by a multi-beam and secondary electrons emitting from scanning points are detected to evaluate said pattern, said method comprising the steps of:

a. accelerating an electron beam emitted from an electron gun up to AKV;

b. irradiating said accelerated electron beam over an aperture plate having a plurality of apertures;

c. reducing a plurality of beams, that has been formed through said apertures, into images on a sample applied with a voltage of −BkV for scanning said sample;

d. extending a spacing between groups of secondary electrons emanating from the scanning points and guiding them to a detector; and e. detecting said groups of secondary electrons independently by said detector to form two-dimensional images, wherein said AkV and BkV are defined as A-B$\leq$0.6 kV, and said groups of secondary electrons have a common passage defined by a two-stage lens which are shared with the primary electron beams.

According to the above method, in the electron optical system having the two-stage of lenses defining the common passage for the primary and the secondary electron beams, the ratio of the landing energy of the primary electron beam to the energy of the secondary electron beam is considerably smaller than that associated with the prior art, and so the focal condition can be easily adjusted to be compatible between the primary beam and the secondary beam, which can help form the multi-beam in the vicinity of a single optical axis.

Further, to accomplish the seventh object as described above, the present invention provides a sixth pattern evaluation method, in which a pattern formed on a substrate is scanned by a multi-beam, and secondary electrons emitting from scanning points are detected to evaluate said pattern, said method comprising the steps of:

a. accelerating an electron beam emitted from an electron gun up to AKV;

b. shaping said electron beam by means of a plurality of apertures into a multi-beam;

c. reducing said multi-beam into images on a sample applied with a voltage of −BkV for scanning said sample;

d. extending a spacing between groups of secondary electrons emitted from the scanning points and guiding them to a detector; and e. detecting said groups of secondary electrons independently by said detector to form two-dimensional image, wherein said AkV and BkV are defined as A-B$\leq$0.3 (kV), and said groups of secondary electrons have a common passage defined by one-stage of lens which are shared with the primary electron beams.

According to the above method, in the electronic optical system having the one-step of lens defining the common passage of the primary and the secondary electron beams, a similar operational effect to the above sixth pattern evaluation method can be obtained.

Further, to accomplish the seventh object as described above, the present invention provides a seventh pattern evaluation method, in which a pattern formed on a substrate is scanned by a multi-beam and secondary electrons emanating from scanning points are detected to evaluate said pattern, said method comprising the steps of:

a. accelerating an electron beam emitted from an electron gun up to AKV;

b. shaping said electron beam by means of a plurality of apertures into a multi-beam;

c. reducing said multi-beam into images on a sample applied with a voltage of −BkV for scanning said sample; and d. detecting said groups of secondary electrons emanating from said scanning points to form a plurality of two-dimensional images, wherein said AkV and BkV are defined as A-B$\leq$0.5 (kV), and a lens most proximal to the sample and used in common by the primary and the secondary electron beams includes an electromagnetic lens.

According to the above method, in the electron optical system having the lens most proximal to the sample and defining the common passage for both of the primary and the secondary electron beams, which includes the electromagnetic lens, a similar operational effect to the above sixth pattern evaluation method can be obtained.

Further, to accomplish the seventh object as described above, the present invention provides an eighth pattern evaluation method, in which a pattern formed on a substrate is scanned by a multi-beam, and secondary electrons emanating from scanning points are detected to evaluate the pattern, said method comprising the steps of:

a. accelerating an electron beam emitted from an electron gun up to AKV;

b. irradiating said accelerated electron beam over an aperture plate having a plurality of apertures, c. reducing a multi-beam, which has been shaped through said aperture plate, into images on a sample applied with a voltage of −BkV for scanning said sample;

d. extending a spacing between groups of secondary electrons emitting from the scanning points and guiding them to a detector; and e. detecting said groups of secondary electrons independently by said detector to form a plurality of two-dimensional images, wherein said AkV and BkV are defined as A-B$\leq$0.5 kV, and a lens most proximal to said sample includes an electromagnetic lens.

According to the above method, in the electron optical system having the lens most proximal to the sample and defining the common passage for both of the primary and the secondary electron beams, which includes the electromagnetic lens, a similar operational effect to the above sixth pattern evaluation method can be obtained.

To accomplish the seventh object as described above, the present invention provides a ninth pattern evaluation method in accordance with any one of the above-defined fifth to eighth pattern evaluation methods, in which said electron optical system has a plurality of optical axes with the optical axes projected along one axial direction being equally spaced.

According to the above method, owing to the configuration allowing said electron optical system to have a plurality of optical axes, the method can improve, in addition to those advantages associated with the above different methods, the throughput in proportion to the number of optical axes.

To accomplish the eighth object as described above, the present invention provides a tenth pattern evaluation method, in which a multi-beam is used to evaluate a pattern, said method comprising the steps of:

a. irradiating an electron beam emitted from a thermionic emission electron gun over an aperture plate having a plurality of apertures;

b. reducing said electron beam, which has passed through said aperture plate, to be focused on a sample;

c. scanning with respective beams of the multi-beam concurrently in the direction orthogonal to a patterned side;

d. detecting a secondary corpuscular beam emitted from scanning points by a multi-detector corresponding to the multi-beam, and obtaining and storing a plurality of signal waveforms; and e. calculating a CD value or a pattern spacing from the plurality of signal waveforms corresponding to said multi-beam.

Further, to accomplish the eighth object as described above, the present invention provides an eleventh pattern evaluation method in accordance with the above-defined tenth pattern evaluation method, in which the beams of said multi-beam are aligned along a straight line not in parallel with the x-axis or the y-axis.

According to those tenth and eleventh pattern evaluation methods, since the CD value or the spacing between the patterns can be calculated from the number of signal waveforms corresponding to the beams of the multi-beam, the measuring time required in the evaluation of the CD value or the pattern spacing can be shortened by an inverse of the number of beams.

Further, to accomplish the eighth object as described above, the present invention provides a twelfth pattern evaluation method, in which a multi-beam is used to evaluate a pattern, said method comprising the steps of:

a. irradiating an electron beam emitted from a thermionic emission electron gun over an aperture plate having a plurality of apertures;

b. reducing said electron beam, which has passed through said aperture plate, to be focused on a sample;

c. scanning with respective beams of the multi-beam concurrently in the direction orthogonal to a patterned side;

d. detecting a secondary corpuscular beam emitted from scanning points by a multi-detector corresponding to the multi-beam, and obtaining and storing a plurality of signal waveforms;

e. moving the multi-beam serially by one-pixel in the direction parallel with a patterned side and then repeating the steps of (c) and (d);

f. forming a two-dimensional image of said pattern from a plurality of signal waveforms corresponding to said multi-beam; and g. calculating an edge roughness from the pattern obtained in the step (f).

According to the above method, since the edge roughness is calculated from the number of signal waveforms corresponding to the beams of the multi-beam, the measuring time required in the evaluation of the edge roughness can be shortened by an inverse of the number of beams.

Further, to accomplish the eighth object as described above, the present invention provides a thirteenth pattern evaluation method in accordance with any one of the above-defined tenth to twelfth pattern evaluation methods, in which said electron gun has a thermionic emission cathode and actuates said cathode under a space charge limited condition.

According to the above method, in any one of the above-defined tenth to twelfth pattern evaluation methods, a shot noise can be reduced.

Further, to accomplish the ninth object as described above, the present invention provides a fourteenth pattern evaluation method, in which a plurality of beams is used to scan a sample surface to thereby evaluate said sample, said method comprising the steps of:

a. adjusting an emission angle of an electron beam emitted from an electron gun by means of an anode having at least two electrodes;

b. converging said electron beam with said emission angle already adjusted, by a condenser lens to form a crossover in an NA aperture;

c. forming a multi-beam with a multi-aperture disposed in the vicinity of said condenser lens;

d. forming an image of the NA aperture by a reduction lens in the vicinity of a principal plane of an objective lens;

e. focusing a reduced image of the multi-aperture on a sample surface by a reduction lens and the objective lens;

f. scanning with the multi-beam across the sample surface, while applying a dynamic focusing;

g. accelerating secondary electrons emanating from the sample by the objective lens to allow them to pass through the objective lens;

h. deflecting the secondary electrons by an E×B separator to advance toward a secondary optical system;

i. extending a spacing between beams of the multi-beam of secondary electrons and detecting them on a plurality of detectors; and j. detecting beams of the multi-beam of secondary electrons independently to form a two-dimensional image for evaluating the sample.

According to the above method, since the emission angle and/or the crossover size of the beam from the electron gun can be adjusted by the lens including a plurality of anodes, therefore the required lens can be simplified into one-step of lens and its associated axial-aligning device is no more necessary but the multi-beam can be formed with a thus simplified optical system.

Further, to accomplish the ninth object as described above, the present invention provides a fifteenth pattern evaluation method, in which a plurality of beams is used to scan a sample surface to thereby evaluate said sample, said method comprising the steps of:

a. focusing an electron beam emitted from an electron gun in an NA aperture by a condenser lens;

b. focusing an image of said NA aperture by a reduction lens in the vicinity of a principal plane of an objective lens;

c. forming a multi-beam by means of a multi-aperture disposed in front of or behind a condenser lens;

d. focusing said multi-beam on the sample surface by a reduction lens and the objective lens;

e. scanning with the multi-beam across the sample, while applying dynamic focusing;

f. accelerating secondary electrons emitting from the scanning points by the objective lens to allow them to pass through the objective lens;

g. deflecting the secondary electrons by an E×B separator to advance toward a secondary optical system;

h. extending a spacing between beams of a multi-beam of secondary electrons and detecting them by a plurality of detectors; and i. detecting beams of the multi-beam of secondary electrons independently to form a two-dimensional image for evaluating the sample, wherein an electric field intensity in the vicinity of said sample can be adjusted within a range of 1.5 kV/mm to 5.5 kV/mm.

According to the above method, during a series of evaluation processes in which the multi-beam is focused on the sample surface to scan it and to thereby produce the two-dimensional image for evaluating the pattern of the sample, the electric field intensity in the vicinity of the sample can be adjusted in a range of 1.5 kV/nm to 5.5 kV/nm, and thus the invention can successfully provide the pattern evaluation method in which the out-of-focus level of the secondary electrons on the detector can be reduced by adjusting the electric field intensity appropriately according to the features on the sample surface, and which is free from a fear of discharge that might be otherwise induced between the lens and the sample.

Further, to accomplish the ninth object as described above, the present invention provides a sixteenth pattern evaluation method, in which a plurality of beams is used to scan a sample surface to thereby evaluate said sample, said method comprising the steps of:

a. irradiating an electron beam emitted from an electron gun having a thermionic emission cathode over a multi-aperture;

b. focusing the electron beam, which has passed through the multi-aperture, in an NA aperture;

c. reducing a group of electron beams, which have been separated independently through the multi-aperture, by a reduction lens and an objective lens to scan the sample surface;

d. accelerating secondary electrons emitting from the scanning points on the sample by the objective lens to allow them to pass through the objective lens;

e. deflecting the secondary electrons by an E×B separator to advance toward a secondary optical system;

f. extending a spacing between beams of the multi-beam of secondary electrons and detecting them by a plurality of detectors; and g. detecting beams of the multi-beam of secondary electrons independently to form a two-dimensional image for evaluating the sample, wherein an arrangement of said multi-beam is defined by an array of m-row×n-column, in which a spacing between i-row, j-column and i+1-row, j-column is substantially equal to the spacing between i-row, j-column and i-row, j+1-column.

According to the above method, the beams in the primary optical system can have a higher resolution than the beams in the secondary optical system and also a maximum possible number of beams can be arranged in a smallest possible circle under the condition that the beams are equally spaced along the one axial direction, and this allows the beams to be converged narrow without inversely increasing the astigmatism and/or the coma aberration.

Further, to accomplish the ninth object as described above, the present invention provides a seventeenth pattern evaluation method in accordance with any one of the above-defined fourteenth to sixteenth pattern evaluation methods, in which plural sets of said electron gun, said primary optical system, said secondary optical system and said detecting system are disposed over a single wafer, wherein the lens of said primary optical system includes a plurality of electrodes in a stack on a single substrate of ceramics, each of said electrodes having a number of holes corresponding to a number of optical axes in association with the number of optical systems arranged.

According to the above method, the throughput in the pattern evaluation can be improved in proportion to the number of optical systems used, yet with the simple structure which facilitates the fabrication and assembling of the electron optical system for providing the pattern evaluation, thus allowing building of the system at a lower cost.

Further, the present invention is characterized in that in manufacturing devices, an evaluation of a wafer in the course of or after processing is provided by using any one of the above-defined pattern evaluation methods.

According to the above method, the device manufacturing method having each different advantage associated with each pattern evaluation method can be obtained.

To accomplish the tenth object as described above, the present invention provides an evaluation method for evaluating a resist pattern formed by an electron beam direct writer and/or an exposing device, such as an excimer laser stepper, or a subsequently processed wafer, said method comprising the step of:

preparing an exposed wafer through a process in which a dose is changed by steps in a row direction, while a focal condition is changed by steps in a column direction, with respect to a plurality of dies arranged in matrix on a wafer, so that the exposure can be carried out with the dose and the focal condition changing in two-dimensional matrix;

measuring a predetermined number of line width at a predetermined locations for each of said plurality of dies;

making a determination on each die whether or not a line width thereof falls in a predetermined range based on said measurement;

applying a defect inspection to the die having the line width falling in said range; and evaluating a lithography margin from a resultant defect distribution obtained in the previous step.

Further, the present invention provides an evaluation method in accordance with the above-defined evaluation method, in which said step of applying a defect inspection comprises:

irradiating an electron beam to a region including a plurality of pixels on said wafer; and magnifying secondary electrons or back-scattered electrons emitting from said region on said wafer by an optical system to obtain a two-dimensional image.

Further, the present invention provides an evaluation method in accordance with the above-defined evaluation method, in which it is determined whether or not said detected defect is resultant from the lithography.

Further, the present invention provides an evaluation method in accordance with the above-defined evaluation method, in which said defect resultant from the lithography is a defect induced by an excessive or insufficient correction to the proximity effect.

Further, the present invention provides an evaluation method in accordance with the above-defined evaluation method, in which said step of applying a defect inspection comprises a step of performing a defect detection of said die by scanning with the electron beam in the direction orthogonal to one axial direction, while moving said wafer continuously in said one axial direction.

Furthermore, the present invention provides a semiconductor device manufacturing method which employs any one of the above-defined evaluation methods.

Those and other objects, features and advantages of the present invention will be apparent by reading the following description with reference to the attached drawings showing illustratively preferred embodiments of the present invention.

BRIEF DESCRIPTION OF THE DRAWINGS

FIG. 7 is a schematic diagram, wherein FIG. 7*a* shows a schematic view of an electron beam apparatus according to another embodiment of the second invention, FIG. 7*b* shows a schematic view of a multi-aperture 2-45 and FIG. 7*c* shows a schematic view of a multi-aperture 2-58 disposed in front of a detector 2-60, respectively;

FIG. 8 is a schematic diagram, wherein FIG. 8*a* shows a schematic view of the multi-aperture 2-45 and FIG. 8*b* shows a state of scanning of the primary electron beams that have passed through the multi-aperture 2-45 shown in FIG. 7*a*;

DESCRIPTION OF THE PREFERRED EMBODIMENTS

Preferred embodiments of the present invention will now be described with reference to the attached drawings.

FIRST EXAMPLE

First, an overview of an electron beam apparatus according to the first invention will be presented.

Figures 1, 2:
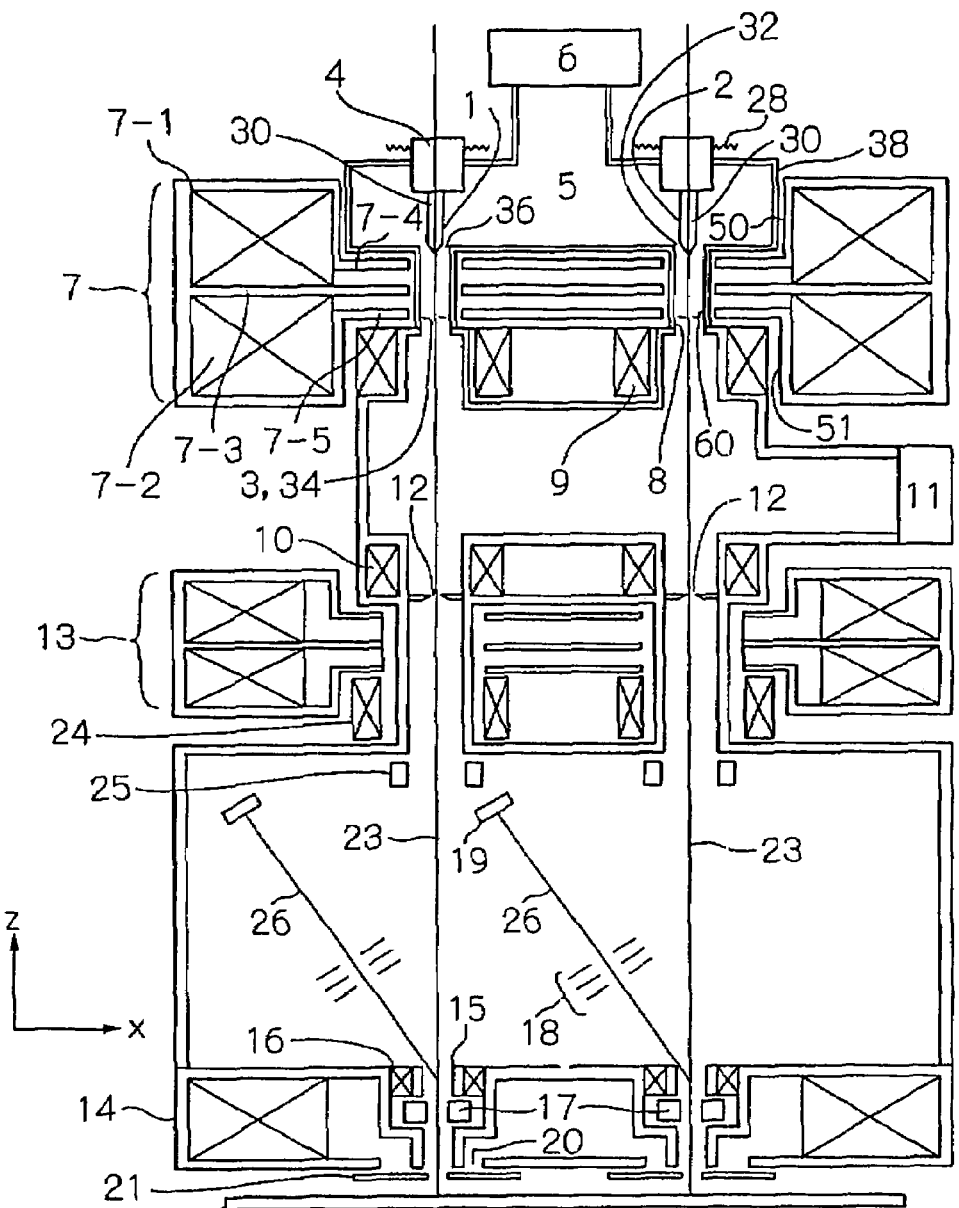
FIG. 1 is a schematic view showing an electron beam apparatus according to an embodiment of a first invention.
FIG. 2 is a plan view of an anode.

An electron beam apparatus according to an embodiment of the present invention as shown in FIG. 1 comprises an electron beam emitter section 32 having an electron gun 30, a plurality of apertures 34 disposed at a location out of an optical axis 23 and an electromagnetic lens 7 operable to control an on-axis electron beam and a plurality of off-axis electron beams emitted from the electron gun 30 so that said plurality of off-axis electron beams may pass through the apertures 34.

The electron beam emitter section 32 comprises two electron guns 30 and a housing 38 serving for holding the electron guns 30 as well as defining an electron gun chamber 5, and an ion pump 6 for evacuating the electron gun chamber 5 to high vacuum is attached to the housing 38. Further, each of the electron guns 30 is connected with a mechanism 28 for activating the electron gun 30 mechanically. Although, in the illustrated embodiment, the electron beam apparatus includes two electron guns 30, the present invention is not limited to this, but only one or two or more electron guns 30 may be arranged.

Each of the electron guns 30 emits a single on-axis electron beam along the optical axis 23 and also a plurality of off-axis electron beams around said on-axis electron beam along the optical axis 23. In the illustrated embodiment, the electron gun 30 emits four off-axis electron beams that are equally spaced along a circle surrounding the on-axis electron beam. However, the present invention is not limited to the four off-axis electron beams but may include at least two or more off-axis electron beams. The electron gun 30 has a cathode 36 and an anode 3. The cathode 36 is made up of ZrO/W chip 1 that has been spot-welded to a tungsten heater 2. It is to be noted that such a cathode 36 is commercially available in the market. The electron gun 30 may be made either one of ZrO/W, carbide of transition metal or a Schottky cathode 36, for example. The anode 3 is disposed at a location not much away from the ZrO/W chip 1 of the electron gun 30.

As shown in FIG. 2, the anode 3 is provided with four apertures of 10 μmφ at four positions out of the optical axis 23 symmetrically along a circle surrounding the optical axis 23. The anode 3 is grounded and the ZrO/W chip 1 is applied with a voltage of −4.5 kV. This diode structure can induce the Schottky emission effect. The electron beams emitted from the ZrO/W chip 1 include a single on-axis electron beam along the optical axis 23 and the four off-axis electron beams around the on-axis electron beam along the optical axis 23. A conventional apparatus has employed only one on-axis electron beam that is emitted in the direction of the optical axis 23. However, since the four off-axis electron beams are associated with extremely high current level as compared to the on-axis electron beam, the on-axis electron beam is hereby discarded but the four off-axis electron beams 34 are permitted to pass through the apertures 34.

The electromagnetic lens 7 forms a magnetic field extending to the anode 3 region. To explain this more specifically, the magnetic field extends from the ZrO/W chip 1 of the electron gun 30 to the vicinity downstream to the anode 3 so that among the electron beams emitted from the ZrO/W chip 1, the four off-axis electron beams can exclusively pass through the apertures 34.

The electromagnetic lens 7 defines a circular configuration in the vicinity of the optical axis 23 viewed from the electron gun 30 side and includes an upstream recess 50 formed in a central portion of its surface defined in the electron gun side, with which a part of the electron gun chamber 5 is fitted. The electromagnetic lens 7 further includes a downstream recess 51 substantially in the same configuration as the upstream recess 50.

The electromagnetic lens 7 comprises a pair of annular coils 7-1 and 7-2 positioned around the optical axis 23, a central magnetic pole 7-3 interposed between said pair of coils, an upstream magnetic pole 7-4 disposed in the upstream side of the central magnetic pole with respect to the optical axis and, a downstream magnetic pole 7-5 disposed in the downstream side of the central magnetic pole with respect to the optical axis. The central magnetic pole 7-3, the upstream magnetic pole 7-4 and the downstream magnetic pole 7-5 are made of ferromagnetic material, respectively. The upstream magnetic pole 7-4 and the downstream magnetic pole 7-5 are also serving as a magnetic circuitry covering the pair of annular coils 7-1 and 7-2.

The electromagnetic lens 7 further includes an opening 60 in a location facing the electron gun 30, which is formed through the central, the upstream and the downstream magnetic poles for permitting the electron beam to pass therethrough. The anode 3 provided with the four apertures 34 is disposed within the opening in the vicinity of the downstream magnetic pole. The magnetic field is produced within the opening with the aide of the central, the upstream and the downstream magnetic poles so as to control the electron beam passing through the opening such that only the off-axial electron beams may pass through the corresponding apertures 34.

The pair of coils consists of the upstream coil 7-1 disposed in the upstream side of the central magnetic pole and the downstream coil 7-2 disposed in the downstream side of the central magnetic pole. The upstream and the central magnetic poles together with the upstream coil define an upstream lens. The downstream and the central magnetic poles 7-5, 7-3 together with the downstream magnetic pole 7-3 define a downstream lens. Thus, the central magnetic pole 7-3 is serving as a common magnetic pole between the upstream lens and the downstream lens. The four off-axis electron beams emitted from the ZrO/W chip 1 are converged while being rotated by these two lenses or the upstream and the downstream lenses. The intensity of the convergence and the rotation angle of the electron beams are controlled appropriately such that the four off-axial electron beams may pass through the apertures 34 disposed in the anode 3. That is, the upstream coil and the downstream coil are applied with respective currents in opposite directions and the intensity of the currents and the ratio between the currents are appropriately controlled. Controlling of the lens intensity can tune the intensity of the convergence (i.e., the R direction, or the radial direction, with respect to the optical axis 23) and the controlling of the current ratio between the upstream lens and the downstream lens can tune the rotation angle (i.e., the θ direction, or the rotational direction). The axial alignment of the electron beams relative to the electromagnetic lens 7 may be provided by the mechanism 28 for moving the electron gun 30 mechanically.

Axial aligning coils 9 and 10, an NA aperture 12 and an electromagnetic lens 13 are disposed in this order downstream to the apertures 34. The electromagnetic lens 13 has the same structure as the electromagnetic lens 7. The axial aligning coil 9 is fitted in a recess of the electromagnetic lens 7 in the downstream side thereof and the axial aligning coil 10 is fitted in a recess of the electromagnetic lens 13 in the upstream side thereof, respectively. The NA aperture 12 is arranged at a location a little closer to the sample than the axial aligning coil 10 and the electron beam having passed through the NA aperture 12 is controlled by the electromagnetic lens 13. In the downstream side of the electromagnetic lens 13 are disposed an axial aligning deflector 24, a first scanning deflector 25, E×B deflectors 15 and 16, a scanning deflector 17, an electromagnetic lens 14, an axisymmetric electrode 21 and a sample 22 in this order. The electron beam apparatus of this illustrated embodiment further comprises a secondary optical system. The axial aligning deflector 24 is fitted in a recess of the electromagnetic lens 13 in the downstream side thereof. The electromagnetic lens 14 includes a gap 20 defined in the side facing to a sample 22, and a lens effect induced by an on-axis magnetic field produced by the gap 20 and an electric field produced by the axisymmetric electrode 21, the sample surface and the electromagnetic lens 14 causes a reduced image of the aperture 34 to be focused on the surface of the sample 22. That is, a plurality of apertures 34 are firstly reduced by a reduction lens 13, and the resultant image thereof is further reduced by an objective lens (a synthetic lens system comprising the electromagnetic lens 14 in combination with an electrostatic lens implemented by the electrode 21 and the like) to form a multi-beam in a size of 50 nmφ to 100 nmφ on the sample 22. Although the electromagnetic lens 14, similarly to the electromagnetic lens 7, 13, has a circular configuration viewed from the upstream side, it includes two recesses formed only in the periphery of the region in upstream side defining the passage of the electron beam. The E×B deflectors 15 and 16 and the scanning deflector 17 are fitted in the recess.

Figure 3:
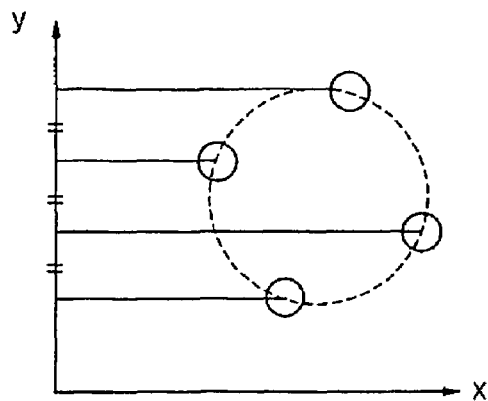
FIG. 3 is a schematic diagram for illustrating how to adjust a rotation of a group of beams by using an electromagnetic lens 13.

The four off-axial electron beams having passed through the apertures 34 form a crossover in the NA aperture 12 with the aid of the convergence effect from the electromagnetic lens 7. The axial aligning with respect to the NA aperture 12 and the electromagnetic lens 13 is carried out by the axial aligning coils 9 and 10. The off-axis electron beams passed through the NA aperture 12 are focused by the electromagnetic lens 13 in position on a principal plane of the objective lens 14, 21, so that the lens aberration in the formation of the images of the apertures 34 on the sample surface can be minimized. As for the electromagnetic lens 13, similarly to the electromagnetic lens 7, the lens intensity and the rotation are independently controllable, and this works to control the orientation on the sample of the four off-axis electron beams that have passed through the apertures 34, so that the four off-axis electron beams projected along the y-axis are all equally spaced, as shown in FIG. 3. After having been adjusted by the electromagnetic lens 13, the four off-axis electron beams are subject to the axial aligning relative to the objective lens 14, 21 by the axial aligning deflector 24. The electron beams are focused into images on the sample 22 by the objective lens 14, 21 and driven by the scanning deflector 25, 17 to scan the sample 22. Secondary electrons emanating from the scanning points on the sample 22 are accelerated by the electric field produced by a positive voltage applied to the axisymmetric electrode 21 and a negative voltage applied to the sample 22 and deflected by the E×B deflector 15, 16 toward a secondary optical system 26. The magnifying lens 18 creates magnified images of the secondary electrons on the detector 19, where the secondary electrons originated from the four off-axis electron beams can be detected without any interference therebetween and resultantly SEM images of four channels per one optical axis 23 can be created.

The electron beam apparatus comprises the electromagnetic lens 7 and the aperture 34 in the anode 3 disposed in the location out of the optical axis 23, wherein the electromagnetic lens 7 can be adjusted such that the plurality of electron beams emitted from the ZrO/W cathode 36 may pass through the apertures 34. This allows the most intensive four off-axis electron beams among a plurality of electron beams emitted from the ZrO/W cathode 36 to be accurately aligned with the positions of the apertures 34 by using the electromagnetic lens 7, which means that the magnified and uniformly intensified four electron beams can be obtained, thus realizing a highly precise evaluation. Further advantageously, the present invention using the four off-axis electron beams for the scanning operation on the sample can provide the evaluation of a substrate with high throughput.

Further, in the present invention, the orientation of the group of four off-axis electron beams in the rotational direction on the sample can be adjusted by the electromagnetic lens 13, and the crossover position can be controlled to meet the requirement to reduce the aberration in the vicinity of the objective lens 14, 21, as well.

The electron gun chamber 5 in the above-illustrated embodiment is isolated from the sample 22 by the apertures 34 and the NA apertures 12 defining orifices of low vacuum conductance, in which the space between the orifices is exhausted by an ion pump 11, contributing to longer operating life and stable operation of the ZrO/W cathode.

SECOND EXAMPLE

Figure 4:
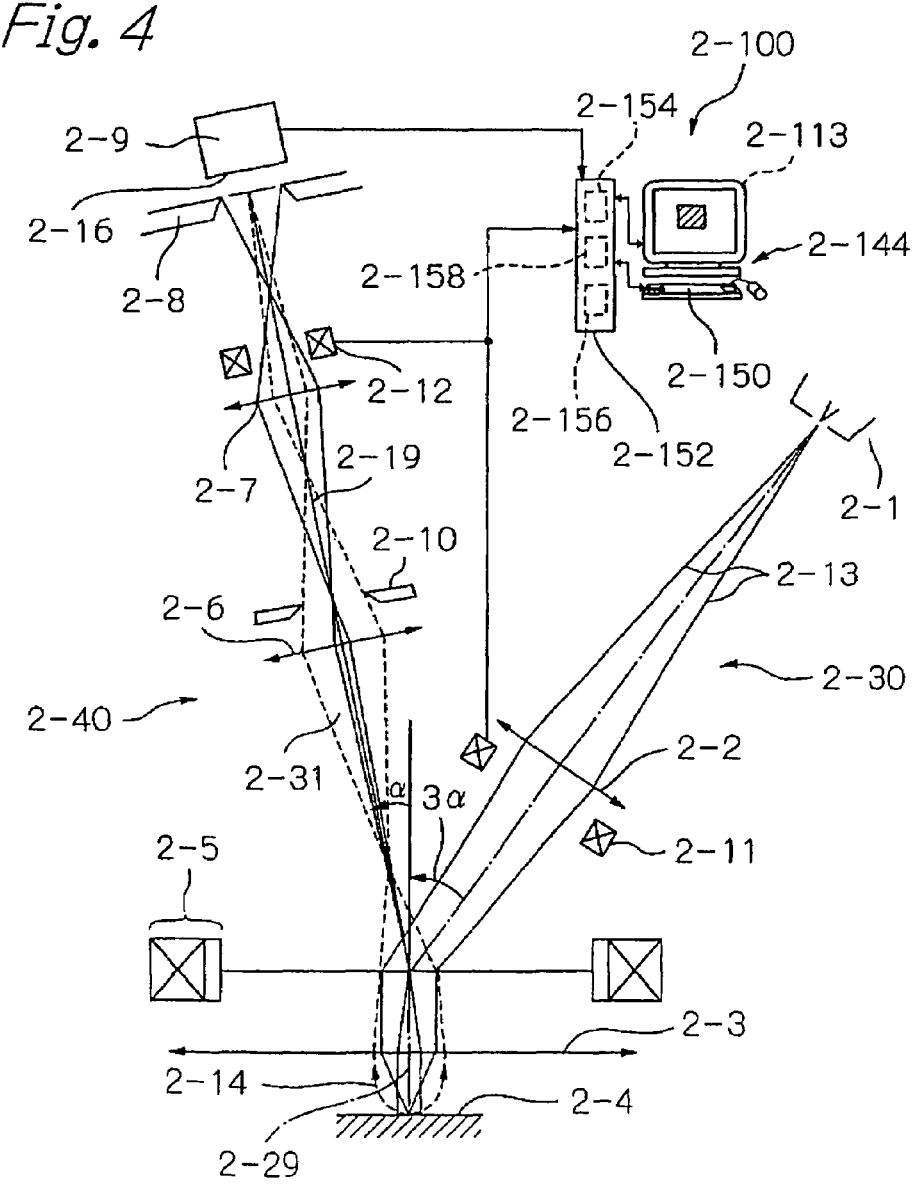
FIG. 4 is a schematic view showing an electron beam apparatus according to an embodiment of a second invention.

A first embodiment using a single beam embodying the second invention will now be described with reference to FIG. 4. An electron beam apparatus of this illustrated embodiment comprises an electron gun 2-1 serving as an electron beam source emitting a primary electron beam 2-13, a primary optical system 2-30 for guiding the primary electron beam onto a sample 2-4 to scan said sample 2-4 with the primary electron beam, a secondary electron detecting unit 2-9 having a detection surface 2-16 for detecting a secondary electron beam 2-14 emitting from the sample 2-4, a secondary optical system 2-40 for guiding the secondary electron beam 2-14 emitting from the sample 2-4 to be focused into an image on the detection surface 2-16 of the secondary electron detecting unit 2-9 and a controller 2-100 for controlling the electron beam apparatus.

The electron gun 2-1 of thermionic beam source type has been employed, in which electrons are emitted by heating an electron emission material (cathode). The electron emission material (emitter) serving as the cathode has employed lanthanum hexaboride ($LaB_6$). The electron beam source used herein may be of electric field emission type or of thermal electric field emission type. For the SEM type of apparatus, the electron beam source of Schottky emission type or of thermal electric field emission type is used.

The primary optical system 2-30 comprises a condenser lens 2-2, 2-3 for irradiating the primary electron beam 2-13 emitted from the electron gun 2-1 in a larger size than a pixel size defined on the sample surface and a scanning deflector 2-11 for performing a raster scanning with the primary electron beam on the sample 2-4.

In the illustrated embodiment, the condenser lens is composed of a condenser lens 2-2 and an objective lens 2-3. The condenser lens 2-2 is disposed in the sample side with respect to the electron gun 2-1 or downstream to the electron gun 2-1, and the objective lens 2-3 is disposed downstream to the condenser lens 2-2 and immediately upstream to the sample 2-4. The condenser lens 2-2 and the objective lens 2-3, thus arranged to serve as the converging lens system, can converge the primary electron beam emitted from the electron gun 2-1 to a size two or three times as large as the pixel size on the sample.

The scanning deflector 2-11 is disposed immediately downstream to the condenser lens 2-2. The scanning deflector 2-11 is controlled by the controller 2-100, in which the deflector 2-11 in response to the instruction from the controller 2-100 deflects the primary electron beam, that has been converged to the specified size through the condenser lens 2-2, to thereby provide the raster scanning with the primary electron beam 2-13 on the sample 2-4.

The primary optical system 2-30 further comprises an E×B separator 2-5 for deflecting the primary electron beam, that has passed through the condenser lens 2-2 and the scanning deflector 2-11, toward the sample 2-4 via the objective lens 2-3. The E×B separator 2-5 forms the electric field and the magnetic field in directions orthogonal to each other, and specifically the E×B separator 2-5 embodies a unit of deflection optical system having the electric field and the magnetic field crossing at a right angle. Selective application of the electromagnetic field can control the electron beam entering the field from one direction to be deflected at a specified angle and the electron beam entering the field from the opposite direction to be deflected at a specified angle in the effect from a force applied by the electric field and a force applied by the magnetic field. The E×B separator 2-5 deflects the primary electron beam 2-13 that has passed through the condenser lens 2-2 and the scanning deflector 2-11 so that the electron beam 2-13 can be irradiated vertically onto the sample 2-4, and also deflects the secondary electron beam 2-14 emanating from the sample 2-4 toward the secondary electron detecting unit 2-9. Although the E×B separator has been herein explained to be included in the primary optical system 2-30, it may be included in the secondary optical system 2-40 or may be included in both or neither of the primary and/or the secondary optical systems, 2-30 and 2-40.

The reason the angle formed between the primary electron beam 2-13 and a normal line 2-A of the sample surface is $3\alpha$, while an angle formed between the secondary electron beam 2-14 and the normal line 2-A of the sample surface is $\alpha$ is that this can reduce the chromatic aberration due to the E×B separator 2-5. A detailed description can be found in Japanese Patent Application No. 2000-335756 and International Patent Application No. PCT/JP01/054949. The contents of those applications are hereby incorporated by reference in their entirety.

The secondary optical system 2-40 comprises the objective lens 2-3 for adjusting the locus of the secondary electron beam 2-14 emitting from the sample 2-4 to thereby reduce the aberration, magnifying lenses 2-6 and 2-7 for focusing a magnified image of the secondary electron beam on the detection surface 2-16, an NA aperture 2-10 interposed between the magnifying lenses 2-6 and 2-7, a correction deflector 2-12 interposed between the magnifying lens 2-7 and the detection surface 2-16 of the secondary electron detecting unit, and an aberration reducing aperture 2-8 interposed between the correction deflector 2-12 and the detection surface 2-16 of the secondary electron detecting unit.

Figure 5:
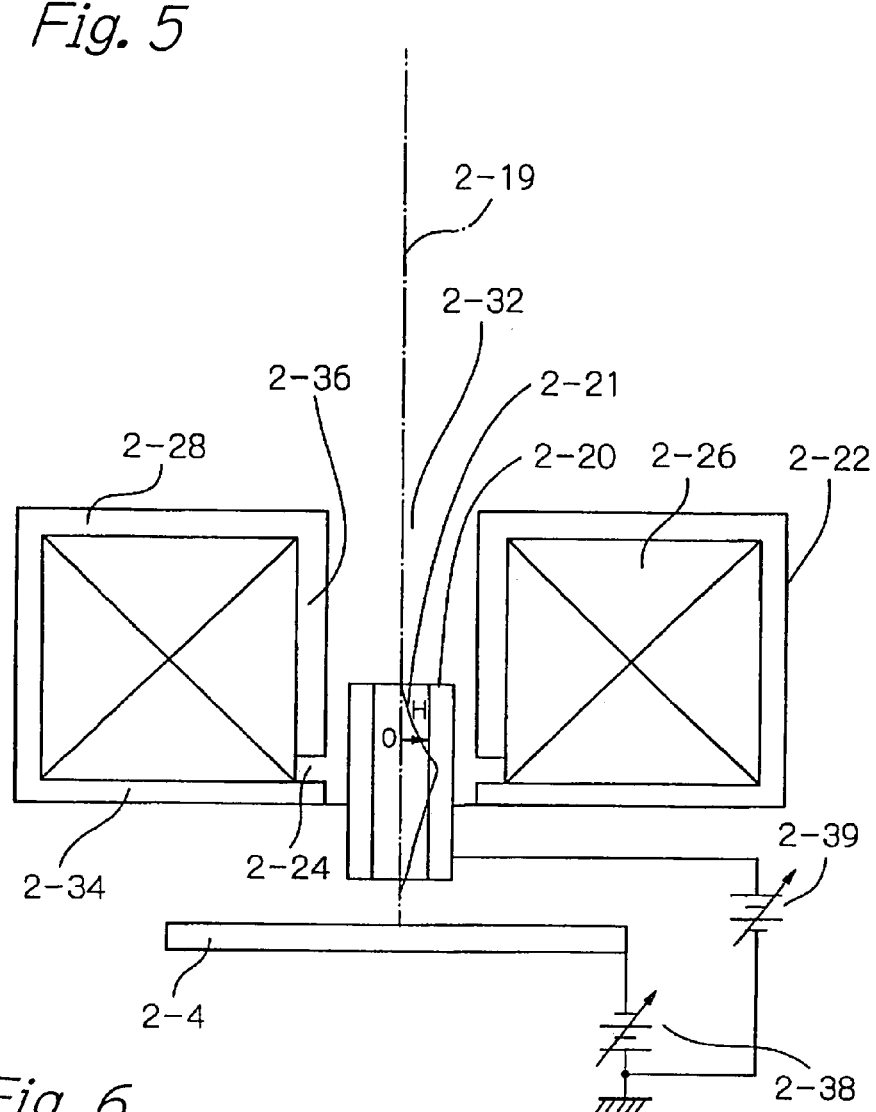
FIG. 5 is a sectional view of an objective lens 2-3.

The objective lens 2-3 is serving both for focusing the primary electron beam 2-13 on the surface of the sample 2-4 and for converging the secondary electron beam 2-14 emanating from the samples 2-14 to be a narrow beam directed to the E×B separator 2-5. A specific structure of the objective lens 2-3 is shown in FIG. 5. The objective lens 2-3 comprises an electromagnetic lens 2-22 having an annular coil 2-26 centered on the optical axis 2-19 and surrounded by a permalloy core 2-28 and a tubular cylindrical electrode 2-20 disposed along the central axis line of the electromagnetic lens or the optical axis 2-19. The electromagnetic lens 2-22 has an annular configuration with a space 2-32 defined in the central region thereof. The cylindrical electrode 2-20 is disposed within the space 2-32 of the electromagnetic lens 2-22 at a location in its sample 2-4 side and partially extending beyond a lower magnetic pole 2-34 of the electromagnetic lens 2-22 toward the sample 2-4 side. A part of the permalloy core 2-28 constitutes an upper magnetic pole 2-36 of the electromagnetic lens 2-22. An annular gap 2-24 is defined in the upper magnetic pole 2-36 in its sample side. Thus, the objective lens 2-3 comprises an ordinary electromagnetic lens having the gap 2-4 defined in the optical axis 2-19 side. An on-axis magnetic field distribution 2-21 of the objective lens 2-3 has its maximum value seen in the central region of the gap 2-24 and substantially zero value on the sample 2-4 surface. The sample 2-4 is applied with a negative voltage by a first variable voltage source 2-38, and the cylindrical electrode 2-20 is applied with a high positive voltage by the second variable voltage source 2-39. Owing to this, an electric field is formed between the sample 2-4 and the cylindrical electrode 2-20. Accordingly, the secondary electron beam emitted from the sample 2-4 is accelerated in the electric field produced by the sample 2-4 and the cylindrical electrode 2-20 and consequently has been highly energized at the time of convergence by the electromagnetic lens 2-22. Owing to this, the on-axis chromatic aberration coefficient of the objective lens 2-3 can be reduced and thus produce a lower aberration. The objective lens 2-3 is included in both of the primary and the secondary optical systems, 2-30 and 2-40.

The magnifying lenses 2-6 and 2-7 may be made of electron lens having a function for magnifying an electron beam image, respectively.

The NA aperture 2-10 is disposed between the magnifying lenses 2-6 and 2-7 to remove the electron beams emitted from the sample 2-4 at a large angle. In the illustrated embodiment, since the secondary electron beam emitted vertically from the sample 2-4, after having passed through the objective lens 2-3, intersects with the optical axis 2-19, the NA aperture 2-10 is preferably disposed at the location of the intersection or on its conjugate plane. This arrangement allows control and reduction of the aberration to a desired level.

The correction deflector 2-12 is controlled by the controller 2-100, in which the correction deflector 2-12, in response to the instruction from the controller 2-100, deflects the trajectory of the secondary electron beam 2-14 so that the image to be produced by the secondary electron beam 2-14 can be always formed on the aberration reducing aperture 2-8. More specifically, the correction deflector 2-12 in response to the instruction from the controller 2-100 actuates in synchronism with the operation of the scanning deflector 2-11 that is driving the primary electron beam to scan the sample 2-4, and corrects the trajectory of the secondary electron beam in synchronism with the scanning operation of the primary electron beam, so that the image of the secondary electron beam 2-14 emitting from the specified area of the sample 2-4 which is scanned by the primary electron beam 2-13 and corresponds to the pixel size defined on the detecting surface 2-16 can be formed over the aberration reducing aperture 2-8 at any times.

The aberration reducing aperture 2-8 allows only such a secondary electron beam to pass therethrough that has emitted from a specified area on the sample 2-4 corresponding to the pixel size on the detection surface 2-16 of the secondary electron detecting unit 2-9 among the secondary electron beams that have emanated from the sample 2-4 and passed through the magnifying lenses 2-6 and 2-7. The aberration reducing aperture 2-8 has a size substantially equal to a product of the pixel size on the sample surface and the magnification of the magnifying lenses 2-3, 2-6 and 2-7. Alternatively, the effective detection area of the detection surface 2-16 may be made equal to the size of the aperture 2-8, and in that case the aperture 2-8 may be eliminated. In case where the secondary optical system suffers from large aberration, the aperture 2-8 may be formed to be slightly smaller in its size than the product of the pixel size on the sample and the magnification scale of said magnifying lens to thereby reduce the effect of the aberration from the secondary optical system.

The controller 2-100 may be implemented by a general-purpose personal computer in one example. The computer comprises a controller main unit 2-144 for executing a control operation of the scanning deflector 2-11, the correction deflector 2-12 and the secondary electron detecting unit 2-9 and also an arithmetic operation in accordance with a specified program, a CRT 2-113 for indicating results from those operations and secondary electron images, and an input section 2-150, such as a keyboard or a mouse, allowing for an operator to input a command. It is a matter of course that the controller 2-100 may be made of hardware dedicated for the defect inspection apparatus or a workstation, for example.

The controller main unit 2-144 includes a CPU, a RAM, a ROM and a variety of control substrates, such as a video substrate, though not shown. The controller main unit 2-144 is connected with a storage device 2-152. The storage device 2-152 may be made of hard disk, for example. On the storage device 2-152 are allocated a secondary electron image storage area 2-154 for storing the secondary electron image data of the sample 2-4 received from the secondary electron detecting unit 2-9 and a reference image storage area 2-156 for storing in advance the reference image data of the sample containing no defect. The storage device 2-152 further contains a control program for controlling the entire electron beam apparatus, especially for controlling the scanning deflector 2-11, the correction deflector 2-12 and the secondary electron detecting unit 2-9, an evaluation program for evaluating the sample, and a control program 2-158 for making a compensation or a correction to any possible deviation from a design parameter value with respect to a position, an orientation (rotational position) or a distance between the beams of a plurality of primary electron beams irradiated to the sample. The image data representing the scanned surface of the sample 2-20 and stored in the secondary electron image storage area 2-154 is compared with the reference image data of the sample containing no defects that has been previously stored in the reference image storage area 2-156 to thereby detect the defect in the sample 2-4.

A general operation of the electron beam apparatus according to the above-illustrated embodiment will now be described.

The primary electron beam 2-13 is emitted from the electron gun 2-1 in the direction angled by $3\alpha$ relative to the normal line 2-A of the sample surface, converged by the condenser lens 2-2 and deflected by the E×B separator so as to be directed toward the sample 2-4. Further, the primary electron beam 2-13 is converged to be two to three times as large as the pixel size on the sample surface and thus directed to the sample 2-4. The primary electron beam is driven by the deflector 2-11 to perform the raster scanning across the sample 2-4.

The secondary electrons emanating from the sample 2-4 in the wide range of direction within ±90° are accelerated by the accelerating electric field for the secondary electrons produced by the axisymmetric cylinder 2-20 contained in the objective lens 2-3 and the sample 2-4 and then converged by the electromagnetic lens 2-22 to be a narrow beam, which in turn passes through the objective lens 2-3 as indicated by the locus 2-14 of the secondary electron. This can reduce the aberration of the objective lens 2-3. The secondary electron beam 2-14 having passed through the objective lens 2-3 is deflected by the E×B separator 2-5 at an angle of $\alpha$ relative to the normal line 2-A of the sample surface. The secondary electron beam is magnified by the magnifying lenses 2-6 and 2-7 to form an enlarged image over the aberration reducing aperture 2-8, where only some of those secondary electron beams that have been emitted from the specific area of the sample corresponding to the pixel size on the detection surface 2-16 of the secondary electron detecting unit 2-9 are allowed to pass through the aberration reducing aperture 2-8. The controller 2-100 synchronizes the correction deflector 2-12 with the scanning operation of the primary electron beam on the sample 2-4 to make a correction, so that the image of the secondary electron beam emitting from the specified area of the sample 2-4 which is scanned by the primary electron beam and corresponds to the pixel size defined on the detecting surface 2-16 can be formed over the aberration reducing aperture 2-8 at any time. The secondary electron beam having passed through the aberration reducing aperture 2-8 is detected by the secondary electron detecting unit 2-9 to produce the SEM image. In this regard, the effective detection area of the detection surface 2-16 may be made equal to the size of the aperture 2-8, and in that case the aperture 2-8 may be omitted.

Figure 6:
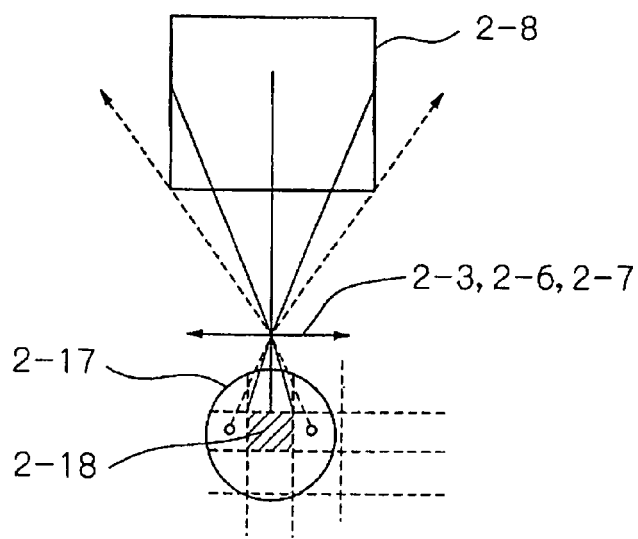
FIG. 6 is a schematic diagram illustrating a relationship among a pixel area 2-18 on a sample, an outer diameter of a primary electron beam 2-17 used in scanning the sample surface and an aperture 2-8 in a detection surface, which has been magnified by magnifying lenses 2-3, 2-6 and 2-7. Secondary electrons emitting from the outside of the pixel 2-8 (shown by dotted lines) are inhibited from passing through the aperture 2-8.

FIG. 6 shows a relationship between a pixel and an outer diameter 2-17 of the primary electron beam used to scan the sample 2-4. The outer diameter 2-17 of the primary electron beam used for the scanning has been converged on the sample 2-4 to have a diameter larger than the pixel size defined thereon. If the NA aperture is properly sized, the aberration of the objective lens 2-3 is reduced sufficiently to allow only the secondary electron beams that have been emitted from the specific region 2-18 on the sample corresponding to the pixel area on the detection surface 2-16 of the secondary electron detecting unit 2-9 to pass through the aberration reducing aperture 2-8, but intercept the rest of the secondary electron beams that have been emitted from the other region than the region 2-18 corresponding to said pixel area not to enter the secondary electron detecting unit 2-9. Owing to this, although the primary electron beam used for the scanning is large in size, this configuration only allows the information limited in the sample region 2-18 corresponding to the pixel area to enter the secondary electron detecting unit 2-9 and thus an SEM image of better resolution can be obtained.

The calculated pixel frequency and frame time in this case are listed as follows. It is to be noticed that the transmission rate of the secondary electrons is hereby assumed to be 25%.

| Pixel size | Beam size | Beam current in a pixel | Pixel frequency | Frame time |
|---|---|---|---|---|
| 0.1 μmφ | 0.2 μmφ | 16 × 100 nA | 400 MHz** | 0.25 sec/mm² |
| 0.05 μmφ | 0.2 μmφ | 400 nA | 100 MHz | 4 sec/mm² |
| 0.025 μmφ | 0.2 μmφ | 100 nA | 25 MHz | 64 sec/mm²* |
| 10 nmφ | 0.2 μmφ | 16 nA | 4 MHz | 2.5 × 10³ sec/mm²*** |

*$\{1\ mm^2/(0.025 \times 10^{-3})^2\} \times \{1/(25 \times 10^6)\} = 64\ sec$;
**$16 \times 100 \times 0.25\ MHz = 400\ MHz$;
***$\{1\ mm^2/(0.01 \times 10^{-3})^2\} \times \{1/(4 \times 10^6)\} = 2.5 \times 10^3\ sec$.

As seen from the comparison of the above table with the table in P2, the present invention has an overwhelming advantage over the prior art. Especially the present invention is advantageous in a small pixel.

THIRD EXAMPLE

Figure 7:
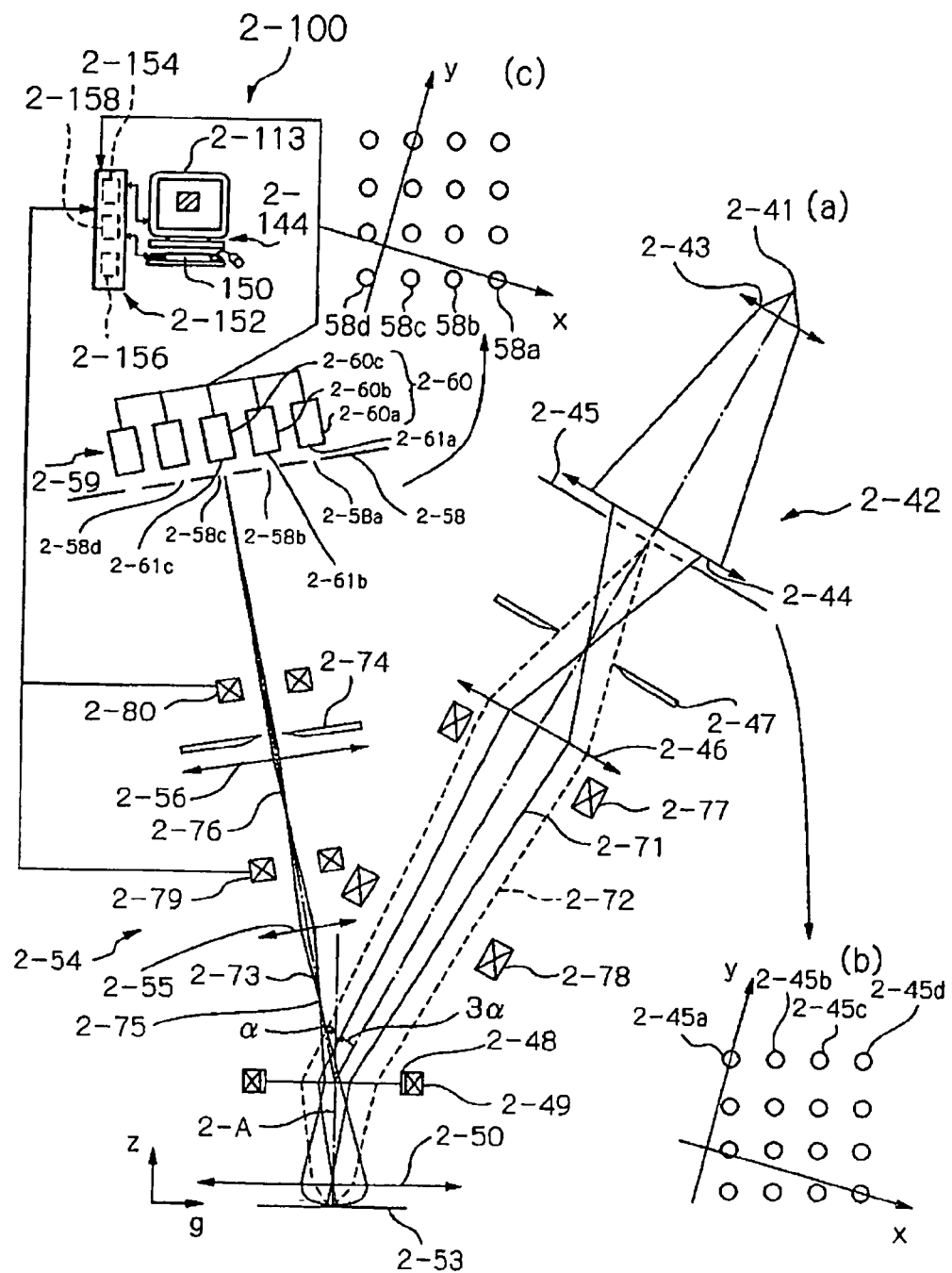

An electron beam apparatus according to a second embodiment of the second invention will now be described with reference to FIG. 7. FIG. 7 is a schematic view of an electron beam apparatus according to the second embodiment of the present invention, in which a primary electron beam is composed of a multi-beam. This electron beam apparatus, as shown in FIG. 7(a), comprises an electron gun 2-41 serving as an electron beam source for emitting a primary electron beam, a primary optical system 2-42 for guiding the primary electron beam onto a sample 2-53 to scan the sample 2-53 with the primary electron beam, a secondary electron detecting unit 2-59 including a plurality of secondary electron beam detectors provided with detection surfaces 2-61 for detecting a secondary electron beam emanating from the sample 2-53, a secondary optical system 2-54 for guiding the secondary electron beam emitting from the sample 2-53 to be focused into an image on the detection surface 2-61 of the secondary electron detecting unit 2-59 and a controller 2-100 for controlling the electron beam apparatus.

The electron gun 2-41 has the same configuration as that of the first embodiment. The primary optical system 2-42 comprises condenser lenses 2-43, 2-44 and 2-46, a multi-aperture 2-45, an NA aperture 2-47, scanning deflectors 2-77 and 2-78, and an objective lens 2-50.

The multi-aperture 2-45 is disposed at a location immediately downstream to the condenser lens 2-44. The multi-aperture 2-45 is composed of 16 apertures, 2-45$a$, 2-45$b$, 2-45$c$ . . . , wherein the primary electron beam emitted from the electron gun 2-41 passes through the multi-aperture 2-45 to be formed into sixteen primary electron beams in total to be used in scanning the sample 2-53. The plurality of apertures formed in the multi-aperture 2-45 is shifted in the rotational direction by an angle of θ as indicated in FIG. 7(b) relative to the coordinate x-y on the sample 2-53. Although the illustrated embodiment has employed 16 apertures, the number of apertures used is not limited to 16.

The condenser lenses 2-43 and 2-44 are disposed at locations defined in the sample side with respect to the electron gun 2-41 or downstream to the electron gun 2-41 and upstream to the multi-aperture 2-45. With the aid of the condenser lenses 2-43 and 2-44 arranged in this configuration, the primary electron beam emitted from the electron gun 2-41 is converged by two steps to thereby adjust the irradiation area of the primary electron beam for the irradiation over the multi-aperture 2-45. The primary electron beam having passed through the multi-aperture 2-45 is formed into a plurality of electron beams, 16 beams of primary electrons in the illustrated embodiment.

The NA aperture 2-47 is interposed between the condenser lenses 2-44 and 2-46, and a crossover image of the primary electron beam that has passed through the multi-aperture is formed in the NA aperture 2-47. The NA aperture helps reduce the aberration. The crossover image formed in the NA aperture 2-47 is focused into an image on a principal plane of an objective lens 2-50.

The condenser lens 2-46 is disposed downstream to the NA aperture 2-47 and the objective lens 2-50 is disposed immediately upstream to the sample 2-53. The condenser lens 2-46 serves to focus the crossover image formed in the NA aperture 2-47 on the principal plane of the objective lens so that every one of the 16 primary electron beams has a size two to three times as large as a pixel size on the sample surface.

The scanning deflectors 2-77 and 2-78 are arranged downstream to the condenser lens 2-46 in two steps. The scanning deflectors 2-77 and 2-78 are under the control of the controller 2-100, wherein in response to an instruction from the controller 2-100, the scanning deflectors 2-77 and 2-78 deflects the primary electron beams that have passed through the condenser lens 2-46 and thus converged into the specified size and thereby provides raster scanning with the primary electron beams in the x-axial direction across the sample 2-53. In addition, the sample table is moved continuously in the y-axial direction, and these x- and y-axial motions provide two-dimensional scanning operation with the primary electron beams on the sample.

The primary optical system 2-42 further comprises an E×B separator 2-48, 2-49 for deflecting the 16 primary electron beams having passed through the scanning deflector 2-78 toward the sample 2-53 via the objective lens 2-50. The configuration, operation and function of the E×B separator 2-48, 2-49 are the same as in the first embodiment. An optical path is defined between the E×B separator 2-48, 2-49 and the sample 2-53 for the common passage of the primary and the secondary electron beams.

An angle formed by the primary electron beam and the normal line 2-A of the sample surface is 3α and an angle formed by the secondary electron beam and the sample surface is α, similarly to the first embodiment.

The secondary optical system 2-54 comprises the objective lens 2-50 for controlling the loci of 16 groups of secondary electron beams emanating from the sample 2-53 corresponding to the number of 16 of the primary electron beams to thereby reduce the aberration, magnifying lenses 2-55 and 2-56 for focusing the secondary electron beam into a magnified image on the detection surface 2-61, correction deflectors 2-79 and 2-80 disposed downstream to the magnifying lenses 2-55 and 2-56, respectively, an NA aperture 2-74 disposed between the magnifying lens 2-56 and the deflector 2-80 and a multi-aperture 2-58 disposed in front of the secondary electron detecting unit 2-59.

The objective lens 2-50 is serving both for focusing the primary electron beam on the surface of the sample 2-53 and for converging the secondary electron beam emanating from the sample 2-53 to be narrow toward the E×B separator 2-49, and the structure of the objective lens 2-50 is similar to the objective lens 2-3 in the first embodiment as shown in FIG. 5. The objective lens 2-50 allows for the common passage of the primary and the secondary electron beams.

The function of the magnifying lens 2-55, 2-56 is similar to that in the first embodiment.

The NA aperture 2-74 eliminates any electron beams that have been emitted at a large angle relative to the normal line of the sample 2-53. This can control the aberration to meet a desired size. The NA aperture 2-47 may be omitted, if it is not required to reduce the aberration further.

The correction deflector 2-79 is under the control of the controller 2-100, wherein in response to an instruction from the controller 2-100, the correction deflector 2-79 deflects the locus of the secondary electron beam so that the crossover image produced by the secondary electron beam can be formed over the NA aperture 2-74 at any time. More specifically, the correction deflector 2-79 is actuated in synchronism with the operations of the scanning deflectors 2-77 and 2-78, which drive the primary electron beam to scan the sample 2-53, in response to the instruction from the controller 2-100 so that the locus of the secondary electron beam may be corrected in synchronism with the scanning operation of the primary electron beam, and thereby the crossover image produced by the secondary electron beam can be formed over the NA aperture 2-74 at any time.

The correction deflector 2-80 is also controlled by the controller 2-100, wherein in response to an instruction from the controller 2-100, the correction deflector 2-80 deflects the locus of the secondary electron beam so that the image of the secondary electron beam having passed through the NA aperture 2-74 may be formed over the multi-aperture 2-58 in front of the corresponding detector 2-60 at any time. More specifically, the correction deflector 2-80 is also actuated in synchronism with the operations of the scanning deflectors 2-77 and 2-78, which drive the primary electron beam to scan the sample 2-53, in response to the instruction from the controller 2-100 so that the locus of the secondary electron beam may be corrected in synchronism with the scanning operation of the primary electron beam and thereby the image of the secondary electron beam having passed through the NA aperture 2-74 can be formed over the corresponding multi-aperture 2-58 in front of the detector 2-60 at any time.

The multi-aperture 2-58 in front of the detector 2-60 allows only such a secondary electron beam to pass therethrough that has emanated from a specified area of the sample 2-53 corresponding to the pixel size on the detection surface 2-61 among the secondary electron beams that have emitted from the sample 2-53 and passed through the magnifying lenses 2-50, 2-55 and 2-56. Each of the apertures of the multi-aperture 2-58 in front of the detector 2-60 has a size substantially equal to a product of the pixel size of the detector 60 on the corresponding sample surface and the magnification factor of the magnifying lenses 2-50, 2-55 and 2-56.

The multi-aperture 2-58 includes a plurality of apertures corresponding to a plurality of primary electron beams. In the illustrated embodiment, since 16 pieces of the primary electron beams have been formed by the multi-aperture 2-45 disposed downstream to the electron gun 2-41, correspondingly the multi-aperture 2-58, as shown in FIG. 7(c), is composed of 16 apertures, 2-58a, 2-58b, 2-58c . . . . Similarly to the multi-aperture 2-45, the multi-aperture 2-58 is shifted in the rotational direction by an angle of θ. The multi-aperture 2-58 is arranged in a position so that the 16 pieces of secondary electron beams emanating from the irradiation points on the sample 2-53 by the primary electron beams can be focused into 16 pieces of enlarged images through the magnifying lenses 2-50, 2-55 and 2-56 over respectively associated apertures of the multi-aperture 2-58.

The secondary electron detecting unit 2-59 includes a plurality of secondary electron detectors 2-60. More specifically, the secondary electron detecting unit 2-59 comprises 16 pieces of secondary electron detectors, 2-60a, 2-60b, 2-60c . . . , corresponding to the 16 pieces of primary electron beams. The secondary electron detectors 2-60a, 2-60b, 2-60c . . . are arranged in association with the 16 apertures of the multi-aperture 2-58, 2-58a, 2-58b, 2-58c . . . , respectively. The secondary electron detectors are all independent from one another and individually have the detection surfaces, 2-61a, 2-61b, 2-61c . . . . Each of the detection surface 2-61a, 2-61b, 2-61c . . . is positioned correspondingly to each associated aperture 2-58a, 2-58b, 2-58c . . . . Each of the 16 groups of secondary electron beams emanating from the sample 2-53 passes through its associated aperture of the multi-aperture 2-58 and detected by its associated secondary electron beam detector 2-60. Although FIG. 7 shows as if only a single secondary electron beam passes through the aperture 2-58c, this is intended to illustrate the embodiment clearly in a simplified manner, and the other 15 secondary electron beams are hereby omitted. This implies that the image of the sample surface is formed on a surface of the multi-aperture 2-58. Accordingly, the image of the secondary electrons from the incident point of the beam which has passed through the aperture 2-45a is formed over the aperture 2-58a, and similarly the images of the secondary electrons from the incident points of the beams which have passed through the apertures 2-45b, 2-45c, 2-45d . . . can be formed over respective associated apertures 2-58b, 2-58c, 2-58d . . . , respectively.

The controller 2-100 is similar to that in the first embodiment.

A general operation of the electron beam apparatus according to the above-illustrated embodiment will now be described.

Figure 8:
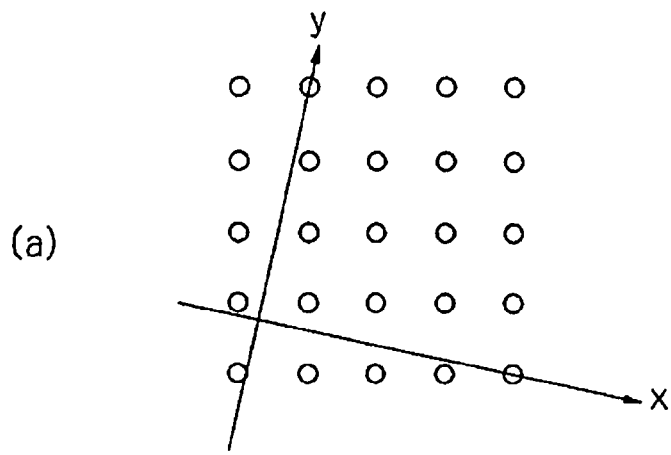
Figure 8:
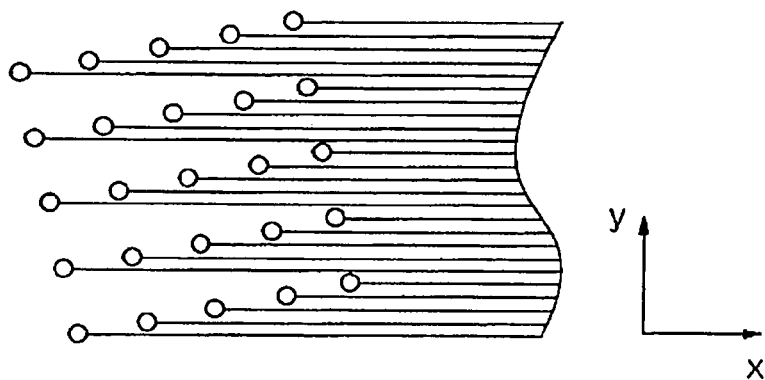

The primary electron beam is emitted from the electron gun 2-41 in the direction angled by 3α relative to the normal line of the sample surface and magnified by the condenser lenses 2-43 and 2-44 in two steps so that the primary electron beam may be irradiated onto the multi-aperture 2-45 appropriately. Then, the primary electron beam passes through the multi-aperture 2-45 including a plurality of apertures to be formed into a plurality of primary electron beams, which in turn forms a crossover image in the NA aperture 2-47, converged by the condenser lens 2-46 and deflected by the E×B separator 2-48, 2-49 toward the sample 2-53. Each of the plurality of primary electron beams is further converged by the objective lens 2-50 to be two to three times as large as the pixel size on the sample surface and projected onto the sample 2-53. The primary electron beams is driven by the scanning deflectors 2-77 and 2-78 so as to perform the raster scanning in the x-axial direction. In the case where the multi-aperture 2-45 defines the array as shown in FIG. 8(a), the raster scanning is performed as shown in FIG. 8(b), thus achieving a highly efficient scanning encompassing 16 pixels×scanning width per one scanning operation.

The secondary electron beam emitting from the sample 2-53 in the wide range of direction within +90° is converged into a narrow beam and passes through the objective lens 2-49, as is the case in the first embodiment. This helps reduce the aberration of the objective lens 2-50. The secondary electron beam having passed through the objective lens 2-50 is deflected by the E×B separator 2-48, 2-49 in the direction defined by an angle α relative to the normal line 2-A of the sample surface. The secondary electron beam is magnified by the magnifying lens 2-55, 2-56 and deflected in its locus by the correction deflector 2-79 to form a crossover image on the NA aperture 2-74. The secondary electron beam having passed through the NA aperture 2-74 is deflected in its locus by the deflector 2-80 to produce a magnified image over the multi-aperture 2-58 in front of the detector 2-60, wherein only some of those secondary electron beams that have been emitted from the specified region of the sample corresponding to the pixel size on the detection surface 2-61 of the secondary electron detecting unit 2-59 are allowed to pass through the multi-aperture 2-58 in front of the detector 2-60. This can eliminate the aberration. The 16 pieces of secondary electron beams are deflected by the correction deflectors 2-79 and 2-80, concurrently pass through respective associated apertures of the multi-aperture 2-58 in front of the deflectors 2-60 and then are detected by the associated detectors 2-60. An output signal from each detector 2-60 is sent to the controller 2-100, where the SEM image is formed based on the output signal from each detector 2-60. At this time, the positional correction is applied according to the beam position of the multi-beam, and a single SEM image is formed by using the 16 detector units. If the NA aperture of the secondary optical system is omitted, the lens of the structure shown in FIG. 9, which comprises a gap defined in the sample side, may be used as the objective lens. In that case, since the axial magnetic field is not zero on the sample, the principal ray of the secondary electrons never intersects with the optical axis, and so the aperture cannot be placed. This circumstance requires that the size of the aperture in front of the detector is made smaller to thereby reduce the aberration.

Figure 9:
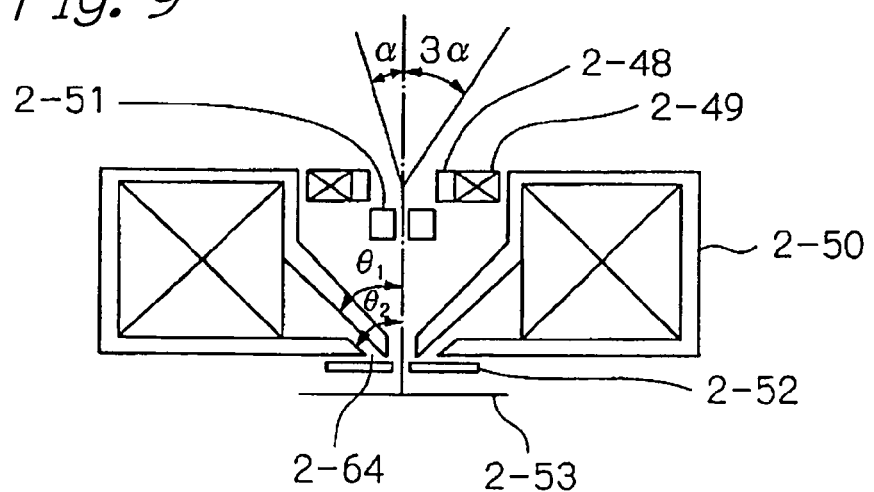
FIG. 9 is a schematic diagram showing a structure of an objective lens 2-50.

The objective lens 2-50 may employ the structure shown in FIG. 5, or alternatively may take the structure of FIG. 9. The primary electron beam is entered at an angle of 3α relative to the optical axis of the objective lens 2-50, deflected by the E×B separator 2-48, 2-49 to be in alignment with the optical axis, and formed into a plurality of beams by the objective lens 2-50 on the sample 2-53, and then the secondary electrons emanating from the sample 2-53 are converged to be narrow and focused into a plurality of secondary electron images in the vicinity of the principal plane of deflection of the E×B separator 2-48, 2-49. The beam is deflected to the −α direction by the electrostatic deflector 2-48 of the E×B separator and deflected to the +2α direction by the electrostatic deflector 2-49 of the E×B separator, resulting in the total deflection in the α direction. Accordingly, the secondary optical system 2-54 is disposed in the α direction. Actually, from the fact that the primary beam incident from the 3α direction has a slightly higher energy than the secondary electrons leaving in the α direction, it is considered that the deflection angle of the primary beam is around 2.7α not 3α. The deflector 2-78 serving as the second step deflector for the primary electrons may be arranged at the location 2-51 of FIG. 9. Preferably, the element 2-51 may employ an electrostatic deflector. The element 2-52 is an axisymmetric circular disk to be applied with a positive voltage. A lens gap 2-64 is open in the sample side and preferably the angles formed by the gap surfaces and the optical axis, $\theta_1$, $\theta_2$, may be equal to or greater than 45°.

FOURTH EXAMPLE

An overview of an electron beam apparatus according to an embodiment of the third invention will now be presented.

Figure 10:
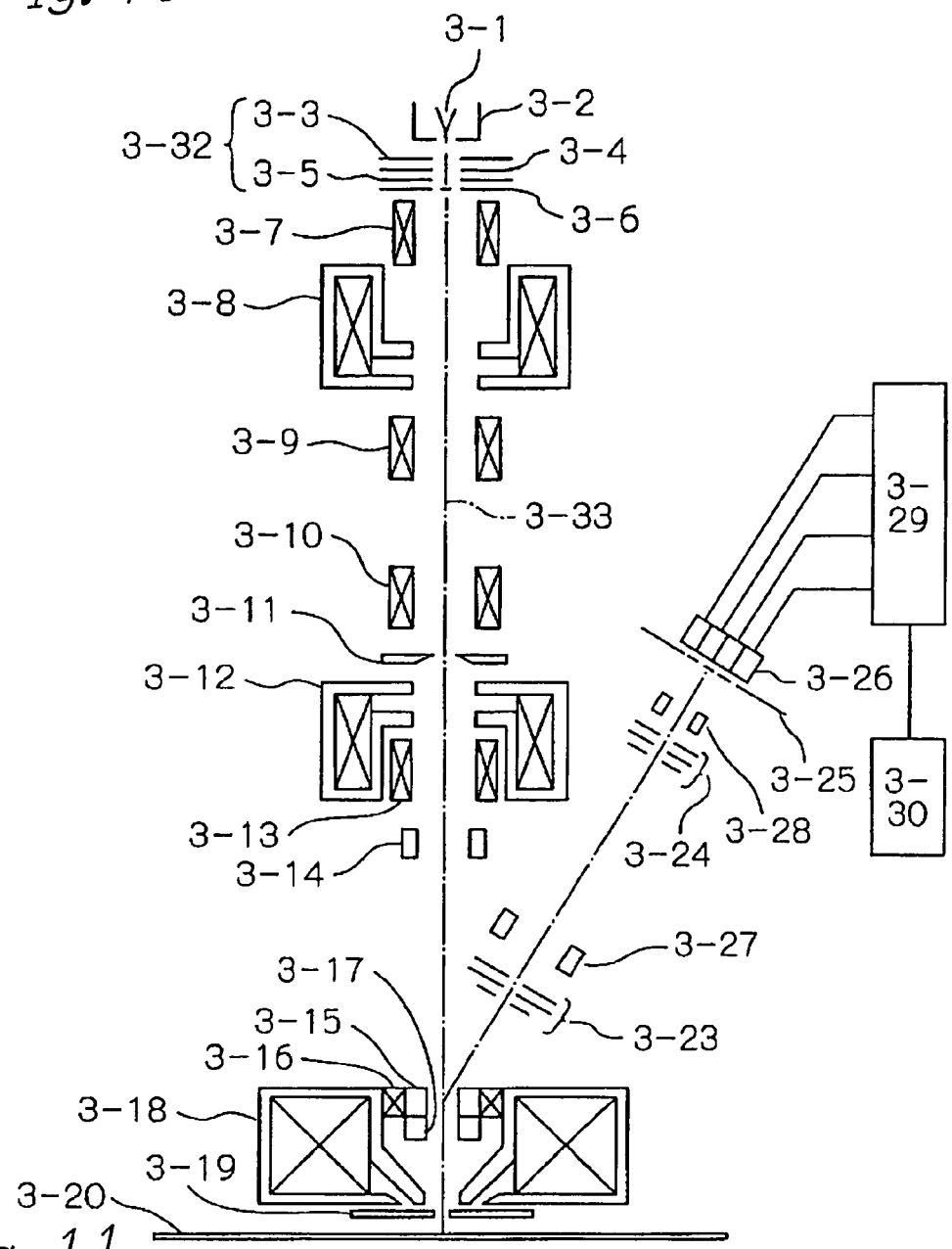
FIG. 10 is a schematic diagram of an electron beam apparatus according to an embodiment of a third invention.

FIG. 10 is a schematic diagram of an electron beam apparatus according to an embodiment of the present invention. The electron beam apparatus of the illustrated embodiment comprises a primary optical system for guiding the primary electron beam onto a sample so as to scan the sample with the primary electron beam and a secondary optical system for detecting secondary electrons emitting from the sample.

The primary optical system comprises an electron gun 3-32 for emitting a primary electron beam, a plurality of apertures 3-21 for defect detecting for forming the primary electron beam emitted from the electron gun 3-32 into a plurality of defect detecting primary electron beams to perform defect detection, at least one aperture 3-22 for defect reviewing for forming the primary electron beam emitted from the electron gun 3-32 into at least one primary electron beam for defect reviewing to perform defect reviewing, axial aligning deflectors 3-7, 3-9, 3-10 and 3-13, a condenser lens 3-8, an NA aperture 3-11, a reduction lens 3-12, scanning deflectors 3-14 and 3-17 for driving the primary electron beam to scan a sample 3-20 and an objective lens 3-18 for reducing the primary electron beam to be focused on the sample 3-20.

The electron gun 3-32 comprises a W filament for heating a ZrO/W cathode, a Schottky shield 3-2 and a first, a second and a third anodes 3-3, 3-4, 3-5. The cathode may be made of one selected from a group consisting of ZrO/W, LaB$_6$, carbide of transition metal, and Schottky cathode, and in the illustrated embodiment, the cathode is made of ZrO/W. For the cathode, if made of carbide of transition metal, such as TaC, the electron beams are emitted in four or eight different directions along the periphery around an optical axis 3-33. For the cathode made of LaB$_6$, owing to its intensive emittance, a number of multi-beams may be formed in the vicinity of the optical axis.

Figure 11:
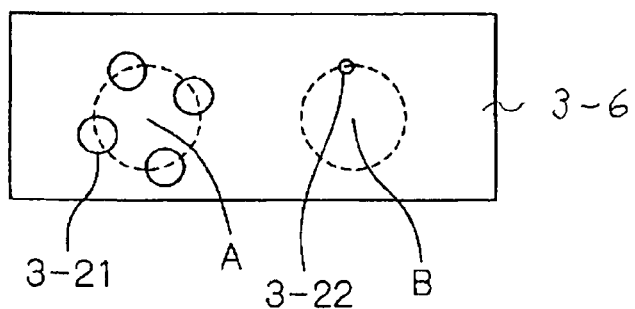
FIG. 11 is a plan view of an aperture plate.

A plurality of apertures 3-21 for defect detecting and at least one aperture 3-22 for defect reviewing are disposed behind or downstream to the third anode. In the illustrated embodiment, the apertures 3-21 for defect detecting are arranged at four locations out of the optical axis 3-33 symmetrically along the circumferential direction, and the aperture 3-22 for defect reviewing is arranged at one location out of the optical axis 3-33. Further, both of the apertures 3-21 for defect detecting and the aperture 3-22 for defect reviewing are formed in a single aperture plate 3-6 as shown in FIG. 11. However, only the apertures 3-21 for defect detecting may be disposed in the aperture plate 3-6 but the aperture 3-22 for defect reviewing may be disposed in a separate aperture plate, though not shown. The aperture 3-22 for defect reviewing is smaller in size than the aperture 3-21 for defect detecting, and this may help converge the primary electron beam for defect reviewing to be narrower than the defect detecting primary electron beam. Further regarding the size, the primary electron beam for defect reviewing may be sized one-half of or smaller than said defect detecting primary electron beam. In the illustrated embodiment, the aperture 3-21 for defect detecting has a size of 30 μmϕ, which makes it difficult for the gas to be relieved and thus reduces vacuum conductance, and accordingly it also serves to maintain an electron gun chamber in a high vacuum condition.

Figure 13:
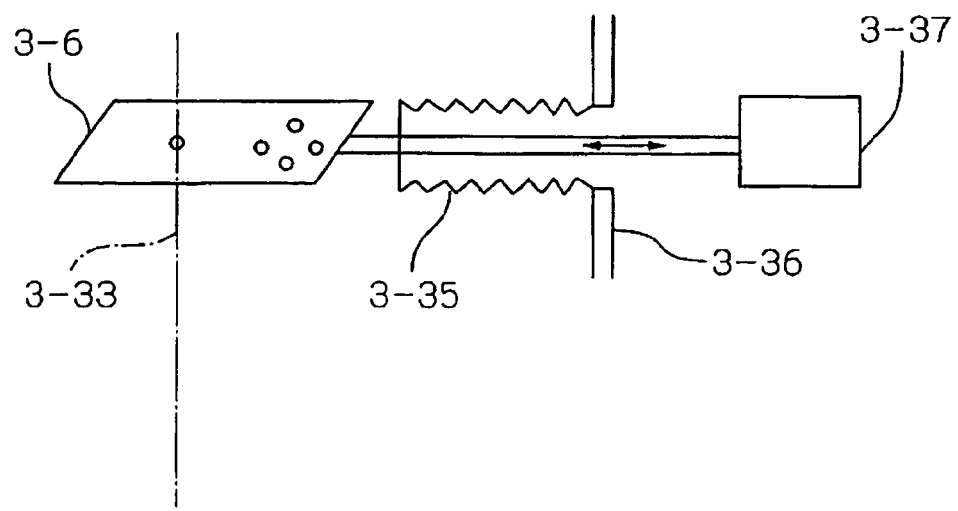
FIG. 13 is a schematic diagram showing a coupling between an aperture plate and an actuator.
Figure 14:
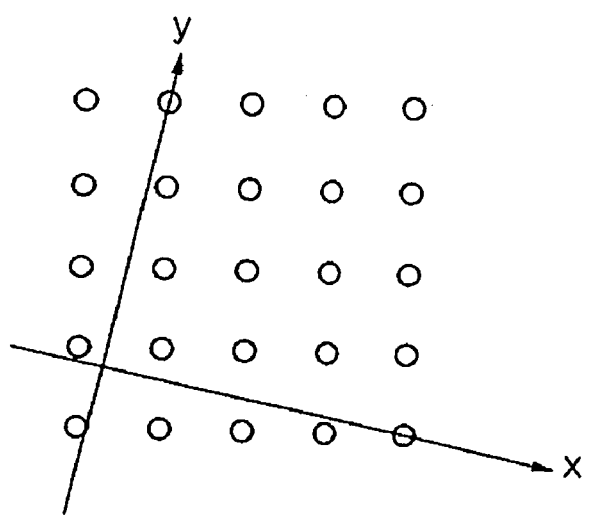
FIG. 14 is a schematic diagram showing how to scan with electron beams along with apertures.
Figure 14:
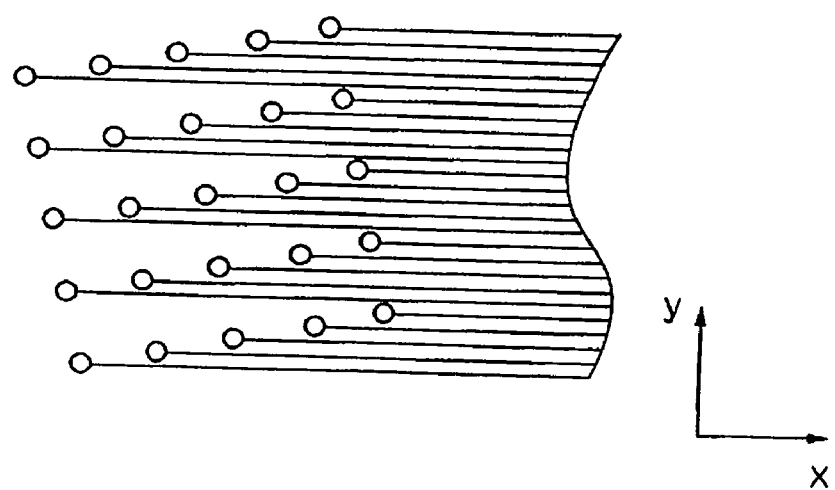

The aperture plate 3-6 is attached to a housing (not shown) of the electron beam apparatus so that it can move in the direction crossing the optical axis 3-33. That is, as shown in FIG. 13, the aperture plate 3-6 is fixed to one end of a bellows 3-35 in vacuum, and the bellows 3-35 in the other end thereof is fixed to a vacuum wall 3-36 via a fitting for mounting the bellows 3-35. The bellows 3-35 in the one end thereof is attached to an actuator 3-37 for making it movable in one axial direction. Accordingly, by moving the aperture plate 3-6 to make the point A of the aperture plate 3-6 in alignment with the optical axis 3-33, the primary electron beam from the electron gun 3-32 can be irradiated exclusively over the aperture 3-21 for defect detecting. By moving the aperture plate 3-6 to make the point B of the aperture plate 3-6 in alignment with the optical axis 3-33, the primary electron beam from the electron gun 3-32 can be irradiated exclusively over the aperture 3-22 for defect reviewing. For performing the defect detection of the sample 3-20, the aperture plate 3-6 is moved so that the point A of the aperture plate 3-6 is aligned with the optical axis 3-33, while for performing the defect reviewing of any defects, if detected, the aperture plate 3-6 is moved so that the point B of the aperture plate 3-6 is aligned with the optical axis 3-33. The housing of the electron beam apparatus is provided with a monitor which allows to monitor a condition in the electron beam apparatus from outside thereof. This allows for an operator to choose whether the primary electron beam from the electron gun 3-32 should be irradiated exclusively over the aperture 3-21 for defect detecting or exclusively over the aperture 3-22 for defect reviewing, while viewing the primary electron beam from the outside of the vacuum via the monitor. That is, if the aperture 3-21 for defect detecting is selected, the primary electron beam for defect detection may be used to perform the defect detection, or if the aperture 3-22 for defect reviewing is selected, the primary electron beam for defect reviewing may be used to perform the defect reviewing. Although in the illustrated embodiment, the operator can manually move the aperture plate, the aperture plate may be moved by means of the actuator 3-37. If the aperture 3-21 for defect detecting and the aperture 3-22 for defect reviewing are arranged in two separate aperture plates, respectively, the aperture plates may be exchanged with each other so as to place the desired aperture(s) in the electron beam apparatus.

Figure 12:
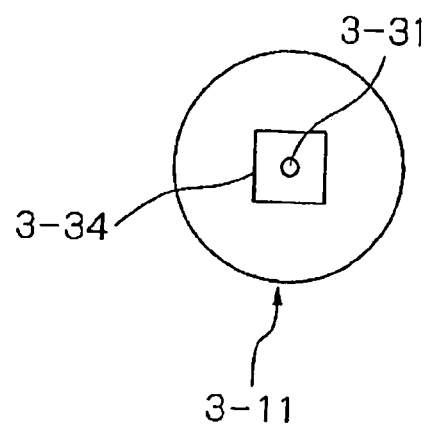
FIG. 12 is a plan view of an NA aperture.

The condenser lens 3-8 is disposed at a location defined in the sample 3-20 side or downstream with respect to the aperture plate 3-6, and the NA aperture 3-11 is disposed downstream to the condenser lens 3-8. The primary electron beam having passed through the aperture 3-21 for defect detecting or the aperture 3-22 for defect reviewing forms a crossover in the NA aperture 3-11 by the condenser lens 3-8. The NA aperture, if configured in a square having a sufficiently larger area than the crossover size 3-31 as shown in FIG. 12, can facilitate the measurement of the crossover size and also prevent the occurrence of intensity fluctuation of the primary electron beam even in the vibration or drifting of the crossover position. Since the aperture angle is determined by the crossover diameter, the control of the beam current and the resolution can be carried out without exchanging the NA apertures.

The reduction lens 3-12 is disposed downstream to the NA aperture 3-11 and operable to magnify the crossover having passed through the NA aperture 3-11 into a focused image on the principal plane of the objective lens 3-18. An exciting condition of the reduction lens 3-12 has been designed so that the aberration in the focusing of the four primary electron beams for defect detection on the sample 3-20 can be reduced.

The scanning deflectors 3-14 and 3-17 are disposed downstream to the reduction lens 3-12 and are operable to deflect the primary electron beam for scanning the sample 3-20.

The objective lens 3-18 is disposed downstream to the deflector 3-17 and operable to reduce the primary electron beam to be focused on the sample 3-20.

The axial aligning deflector 3-7 is interposed between the aperture plate 3-6 and the condenser lens 3-8, the axial aligning deflectors 3-9 and 3-10 are interposed between the condenser lens 3-8 and the NA aperture 3-11, and the axial aligning deflector 3-13 is interposed between the reduction lens 3-12 and the scanning deflector 3-14, and they are operable to provide the axial alignment with respect to the condenser lens 3-8, the NA aperture 3-11 and the objective lens 3-18, respectively.

The secondary optical system comprises an axisymmetric electrode 3-19 for accelerating the secondary electron beam, the objective lens 3-18 for converging the accelerated secondary electron beam, an E×B separator 3-15, 3-16 for deflecting the secondary electron beam emitted from the sample 3-20, magnifying lenses 3-23 and 3-24, axial aligning deflectors 3-27 and 3-28, an aperture 3-25 and a secondary electron detector 3-26.

The axisymmetric electrode 3-19 is disposed in a location defined in the secondary electron detector 3-26 side a bit away from the sample 3-20, wherein the secondary electron beam emitting from the sample 3-20 is accelerated by the electric field produced by the negative voltage applied to the sample 3-20 and the axisymmetric electrode 3-19.

The E×B separator 3-15, 3-16 is, along with the objective lens 3-18, disposed between the axisymmetric electrode 3-19 and the magnifying lens 3-23. The E×B separator 3-15, 3-16 forms the electric field and the magnetic field in orthogonal directions from each other and thus provides a unit of deflection optical system with the electric field and the magnetic field crossed at a right angle. Selective application of the electromagnetic field can control the electron beam entering the field from one direction to be deflected at a specified angle and the electron beam entering the field from the opposite direction to be deflected at a specified angle different from said angle for the former in the effect from a force applied by the electric field and a force applied by the magnetic field. The E×B separator 3-15, 3-16 deflects the secondary electron beam emanating from the sample 3-20 to be directed toward the secondary electron detector 3-26.

The magnifying lenses 3-23 and 3-24 are disposed between the E×B separator 3-15, 3-16 and the aperture 3-25, respectively, and are operable to magnify the image of the secondary electron beam to form an enlarged image over the aperture 3-25 in front of the secondary electron detector 3-26. Since the aberration of the secondary optical system is determined by the objective lens 3-18, the magnifying lenses 3-23 and 3-24 are composed of the electrostatic lens.

The aperture 3-25 is disposed in front of the secondary electron detector 3-26. The aperture 3-25 includes four apertures corresponding to the apertures 3-21 for defect detecting, over which the enlarged images of the secondary electron beams are formed.

The axial aligning deflectors 3-27 and 3-28 are disposed in the secondary electron detector side with respect to the magnifying lenses 3-23 and 3-24, respectively, and are operable to provide the axial alignment of the secondary electron beam with the magnifying lens 3-24 and the aperture 3-25, respectively.

The secondary electron detector 3-26 is composed of a scintillator, a photomultiplier (photoelectron multiplier) and the like, and is operable to detect the four pieces of secondary electron beams having passed through the apertures 3-25 and convert thus detected secondary electron beams into corresponding four analog signals.

The secondary electron detector 3-26 is connected to the image forming circuit 3-30 via an A/D converter 3-29. The four analog signals output from the secondary electron detector 3-26 are converted into digital signals by the A/D converter 3-29, with which the SEM image by four-channel is formed in the image forming circuit 3-30. The image forming circuit 3-30 is configured similarly to the controller 3-100 as discussed above, in which said SEM image by four-channel is compared to the previously stored reference image data on the sample containing no defects to thereby detect any defects in the sample, and if the defect exists in the sample, the coordinate of the defect is stored. The comparison may employ the cell-to-cell detection method, in which the images are compared between the cell portions of the same type on the same die or the die-to-die detection method, in which the comparison is made between the same pattern regions in different dies.

The general operation of the electron beam apparatus according to the illustrated embodiment will now be described.

In the defect detection, the primary electron beam emitted from the electron gun 3-32 is irradiated to the aperture 3-21 for defect detecting to be formed into four primary electron beams for defect detection. The electron gun 3-32 emits a primary electron beam in the optical axis direction, while at the same time, it also emits a plurality of primary electron beams around the optical axis angled thereto. The primary electron beam emitted along the optical axis is blocked by the aperture plate 3-6 but only the plurality of primary electron beams emitted out of the optical axis is permitted to pass through the apertures 3-21 for defect detecting so as to be formed into the above-discussed four primary electron beams for defect detection. Each of the apertures 3-21 for defect detecting is sized to 30 µmφ, wherein the primary electron beams for defect detection having passed through the apertures are reduced by the condenser lens 3-8, the reduction lens 3-12 and the objective lens 3-18 so that the resultant four small-sized primary electron beams for defect detection can be formed on the sample 3-20. Those four primary electron beams for defect detection are deflected in two steps by the scanning deflectors 3-14 and 3-17 to thereby perform the raster scanning on the sample for carrying out the defect inspection of the sample 30. Based on the fact that the primary electron beams emitted in four different directions from the electron gun 3-32 are associated with much higher current level than the primary electron beam emitted in the optical axis direction, the beam current around 400 nA could be obtained with a beam diameter of 50 nm. Owing to this, the primary electron beams for defect detection can perform the scanning operation across the sample 3-20 at the pixel frequency of 400 MHz. With the beam current of 100 nA and the pixel frequency of 100 MHz, the number of electrons per pixel would be 4050, implying that a signal of satisfactory S/N ratio could have been obtained. With the four times high beam current, even if scanning is applied at the four times high frequency, the signal of the same S/N ratio can be obtained. Further, using the four primary electron beams allows the SEM image by four channels to be obtained and thus the defect inspection to be performed at the scanning rate of 1.6 GHz (400 MHz×4) of equivalent frequency. Each of the secondary electron beams emanating from the four scanning points on the sample 3-20 upon scanning with the four primary electron beams for defect detection over the sample 3-20 is accelerated in the electric field produced by the negative voltage applied to the sample and the axisymmetric electrode 3-19 disposed under the electromagnetic lens 3-18, and each of the beams is converged to be narrow to pass through the objective lens 3-18 and then deflected by the E×B separator 3-15, 3-16, to be guided into the secondary optical system. The secondary electron beams are magnified by the two step of magnifying lens 3-23 and 3-24 and formed into enlarged images over the aperture 3-25 comprising the four apertures, and those secondary electron beams that have passed through the apertures 3-25 are detected by the secondary electron detectors 3-26 so as to create the SEM image by four channels in the image forming circuit 3-30. At this stage, the positions of the four primary electron beams for defect detection have been previously measured and the measured values have been previously stored in the image forming circuit 3-30. The image forming circuit 3-30 synthesizes the four pieces of SEM image while at the same time compensating for the misalignment among those primary electron beams for defect detection. In the formation of this image, a scanning signal is input to the image forming circuit 3-30, with which the four pieces of SEM image can be synthesized. The axial alignment of the secondary electron beam to the magnifying lens 3-23 is carried out by the E×B separator 3-15, 3-16, the axial alignment to the lens 3-24 is carried out by the aligning deflector 3-27, and the axial alignment to the aperture 3-25 is carried out by the aligning deflector 3-28. Since the magnifying lenses 3-23 and 3-24 are composed of the electrostatic lenses, the secondary optical system is light in weight and advantageously does not suffer from vibration, though having no vertical arrangement like the primary optical system. The image forming circuit 3-30 compares the SEM image by four channels with the reference image of the sample containing no defect to thereby detect any defects in the sample.

When the defect detection has been completed across the sample 3-20 entirely, then image forming circuit 3-30 stores the coordinate of the detected defect. Based on this information, the operator moves the aperture plate 3-6 so that the point B of the aperture plate 3-6 is in alignment with the optical axis 3-33 and thus makes a control so that the primary electron beam from the electron gun 3-32 can be irradiated exclusively over the aperture 3-22 for defect reviewing.

Then, based on the coordinate information of the defect, the primary electron beam for defect reviewing is aligned with the position of each defect on the sample 3-20 in sequence, where the movement of the stage is suspended and the defect reviewing is performed. The defect reviewing operation is carried out in accordance with the same procedure as the defect detection, with an exception that the different primary electron beam is used in the defect reviewing as discussed above. To perform the defect reviewing, the primary electron beam emitted from the electron gun 3-32 is irradiated over the aperture 3-22 for defect reviewing. In the defect reviewing, since the moving of the stage consumes the majority of time over the image taking, even a single electron beam for defect reviewing can provide the two-dimensional image at a sufficiently high rate. Owing to this, the illustrated embodiment has employed the aperture 3-22 for defect reviewing having a single aperture. However, the aperture 3-22 for defect reviewing may include four apertures and thus four electron beams for defect reviewing can be used, depending on the different conditions. In the defect reviewing, the pixel size on the secondary electron detector 3-26 is required to be equal to or smaller than 25 nm pixel. Accordingly, the beam size of the electron beam for defect reviewing is also required to be equal to or smaller than 25 nm. When a single electron beam for defect reviewing is used, one of the four detectors 3-26 may be used. If the aperture 3-22 for defect reviewing include four apertures, sizing each of four apertures to be equal to or smaller than one-half of the each aperture size of the four apertures for defect detecting 3-22 may advantageously allow to change the beam size without any modifications required in the lens condition.

Assuming that, for example, in the defect reviewing, the SEM image of 10 μm square would be obtained at 100 MHz, the time required, T, is expressed as follows, with the pixel size of 25 nm square:

$$T = \{10 \ \mu m \times 10 \ \mu m / (25 \times 10^{-3})^2\} \times 10^{-8} \ \text{sec}$$
$$= 1.6 \times 10^{-3} \ \text{sec},$$

indicating that the moving of the stage requires a much longer time period (100~500 ms). Therefore, in the above case, it is not necessary to use the four electron beams for defect reviewing but the scanning operation can be still performed only with a single electron beam for defect reviewing as practiced in the illustrated embodiment.

However, if the beam size of 10 nmϕ and the pixel size of 10 nm square are used, the beam current around 400 nA can be obtained with the beam diameter of 50 nm and accordingly the beam current is reduced to 400 nA×(10/50)$^4$=0.64 nA. As a result, a single electron beam for defect reviewing cannot be driven to scan at the pixel frequency of 100 MHz but can be only at the frequency of 0.64 MHz. Under this condition, the time required, T, for obtaining the SEM image of 10 μm square is calculated as follows:

$$T = \{10 \ \mu m \times 10 \ \mu m / (10 \times 10^{-3})^2\} \times \{1/0.64 \times 10^{-6}\} \ \text{sec}$$
$$= 1.56 \ \text{sec},$$

indicating that the time T exceeds the stage moving time. In such a case, the aperture for defect reviewing composed of four apertures, each defining the ¼ diameter, may be used and thus the scanning operation may be performed with the total of four electron beams for defect reviewing. In that case, the time T will be 0.39 sec, which is substantially as long as the stage moving time.

FIFTH EXAMPLE

An overview of an electron beam apparatus according to an embodiment of the fourth invention will now be presented.

Figure 15:
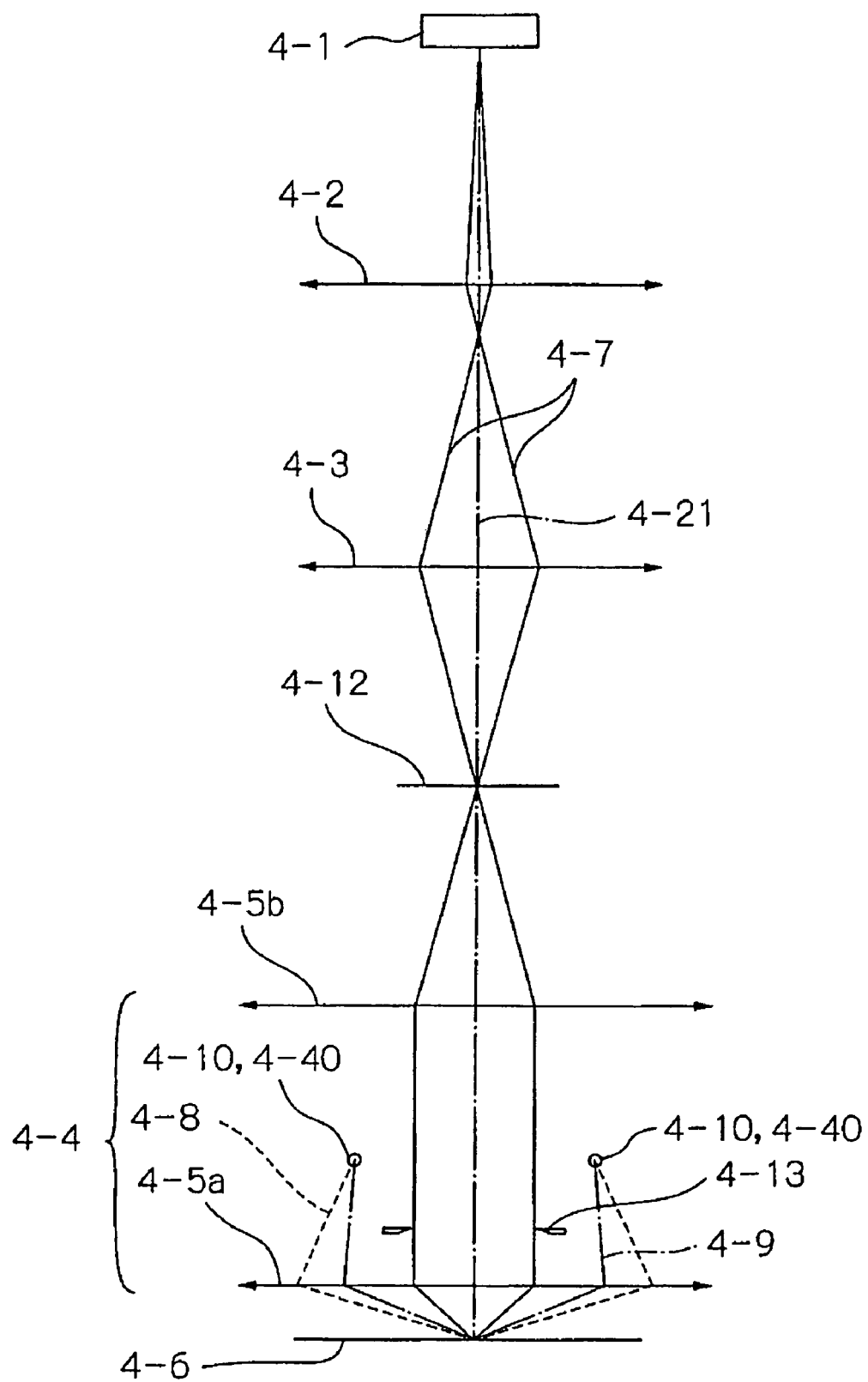
FIG. 15 is a diagram schematically illustrating a formation of an focused image in an electron beam apparatus with a image-projection optical system according to an embodiment of a fourth invention.

FIG. 15 shows a diagram of an electron beam apparatus of image projection optical system focusing a beam into an image according to one embodiment of the present invention.

An electron beam apparatus using an image projection optical system in the illustrated embodiment comprises an electron gun 4-40, a secondary optical system for detecting secondary electron beam or back scattering electrons emitting from a sample, and a detecting unit 4-1 for detecting the secondary electron beam or the back scattering electrons, as shown in FIG. 15. As such, the electron beam apparatus of this embodiment comprises no primary optical system for irradiating the primary electron beam in the oblique direction relative to the normal line of the sample surface and no E×B separator for deflecting the primary electron beam entered from the oblique direction toward the direction along the normal line, but the electron gun 4-40 is arranged in the secondary optical system.

Figure 16:
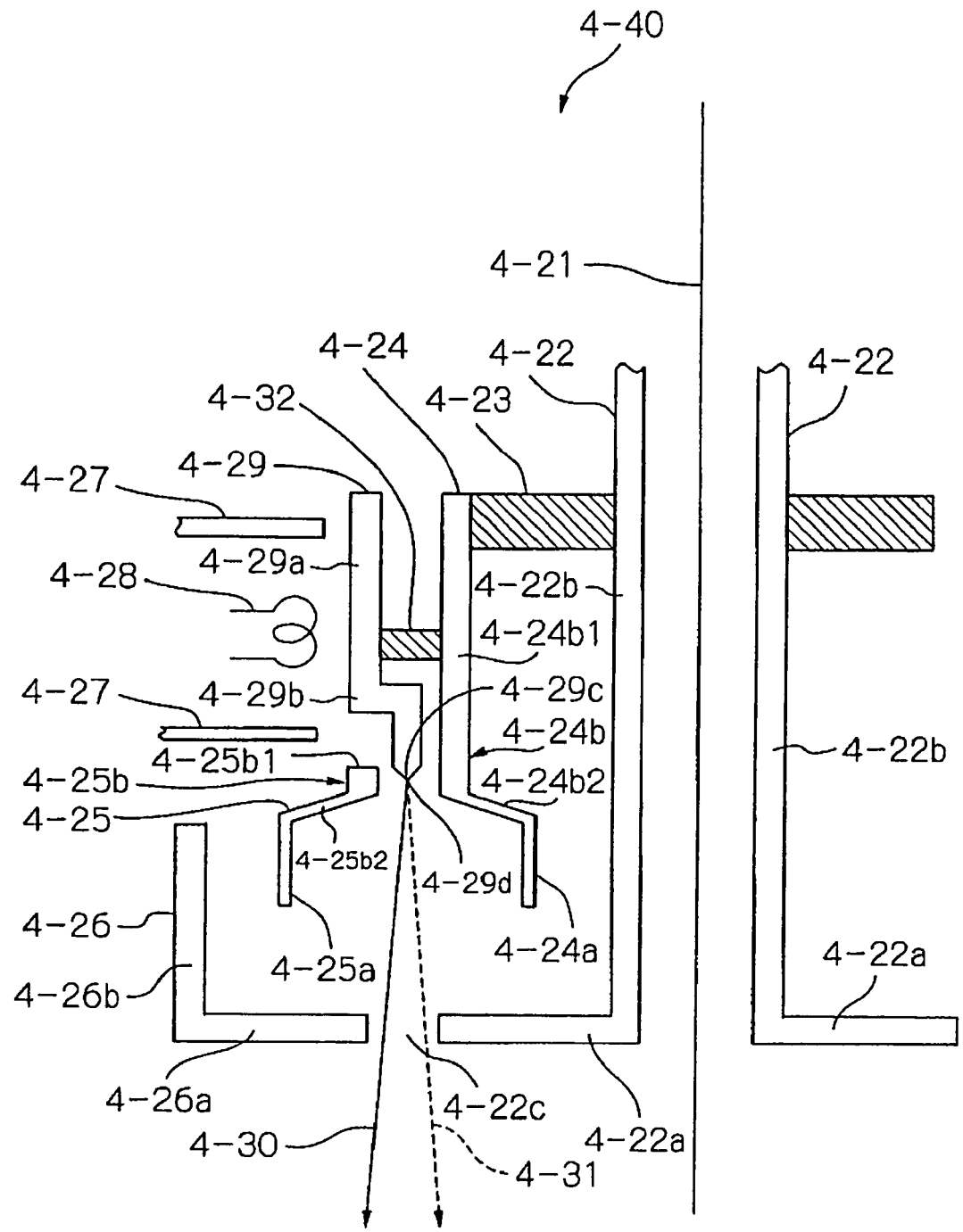
FIG. 16 is a fragmentally sectional view schematically showing an electron gun according to an embodiment of the fourth invention.

The electron gun 4-40 has a ring-shaped cathode 4-29 for emitting a primary electron beam defining a hollow beam from a tip portion thereof, an anode 4-22, 4-26 for controlling the direction of the hollow beam emitted from the cathode 4-29 and a Wehnelt 4-22, 4-25, as shown in FIG. 16. The anode has an inner anode 4-22 that is grounded and an outer cathode 4-26 that is applied with a voltage. In the apparatus according to the prior art, since there is a site where the primary electron beam and the secondary electron beam are sharing a common optical path, the out-of-focus level of the secondary electron beam due to the space charge effect from the primary electron beam may exceed an ignorable value. In the hollow beam of the present case, owing to the configuration allowing the primary electron beam to pass the outer side of the secondary electron beam, there should be induced no out-of-focus of the secondary electron beam even with any increase in the primary electron beams. The irradiation condition of the electron gun 4-40 for determining the emission direction of the primary electron beam can be controlled by adjusting the voltage applied to the outer anode 4-26.

The secondary optical system comprises a doublet lens 404 for focusing the secondary electrons or the back scattering electrons (also referred to as reflected electrons) emanating from the sample 4-6 into an image of the sample 4-6 and magnifying lenses 4-2 and 4-3 for magnifying the focused secondary electron beam and the like.

The doublet lens 4-4 is interposed between the sample 4-6 and the magnifying lenses 4-2 and 4-3, and comprises a pair of electron lenses 4-5a and 4-5b. If the voltage applied to the electron lenses 4-5a and 4-5b is changed, a focal distance of the doublet lens is changed to thereby allow the control of the lens condition. The electron gun 4-40 is interposed between the electron lenses 4-5a and 4-5b and designed to provide an irradiation onto the sample 4-6 if there is a lens effect from the electron lens 4-5a.

The NA aperture 4-13 is interposed between the pair of electron lenses 4-5a and 4-5b and is operable to eliminate the electron beam emanating from the sample 4-6 at a large angle relative to the normal line of the sample 4-6.

The magnifying lenses 4-2 and 4-3 are disposed between the doublet lens 4-4 and the detecting unit 4-1 or downstream to the doublet lens 4-4 and are operable to magnify in two steps the sample image focused by the doublet lens 4-4.

The detecting unit 4-1 is disposed downstream to the magnifying lens 4-2, and comprises a scintillator and a CCD for detecting the secondary electron beams or the like to form an enlarged image of the sample.

The electron gun 4-40 must be able to provide an irradiation in the vicinity of the optical axis 4-21 under both lens conditions for the secondary electrons and the back scattering electrons. Further, the electron gun 4-40 must be placed in a specified location where the secondary electrons and the back scattering electrons from the sample 4-6 would not interfere with the components of the electron gun. To address this, the electron gun 4-40 is placed in the location where the loci of the primary electrons under said two lens conditions intersect with each other on the assumption that the primary electrons have been emitted at a sufficiently large angle from the optical axis 4-21. At this specified location, both of the primary electron beam 4-9 for the secondary electrons and the primary electron beam 4-8 for the back scattering electrons can be used. Such a location 4-10 where the trajectories of the primary electron beams intersect under both lens conditions, one for the secondary electrons and the other for the back scattering electrons, can be determined through a simulation. Although in the illustrated embodiment, the placement of the electron gun 4-40 has been selected to be a location 4-10 where the loci of the primary electron beams under the lens condition for the secondary electrons and the lens condition for the back scattering electrons intersect, the electron gun 4-40 may not be used in common to satisfy both conditions but separate electron guns may be placed, one for the secondary electrons and the other for the back scattering electrons.

It is to be noted that the primary electron beam 4-9 for the secondary electrons and the primary electron beam 4-8 for the back scattering electrons are associated with different angles relative to the optical axis 4-21, as shown in FIG. 15.

A general operation of the electron beam apparatus according to the illustrated embodiment will now be described.

The hollow beam defining the primary electron beam emitted from the electron gun 4-40 placed in the location 4-10 in the direction along the trajectory shown by 4-9 or 4-8 is focused by one lens element 4-5a of the doublet lens onto the optical axis 4-21 of the sample 4-6. At that time, the primary electron beam for the secondary electrons follows the trajectory 4-9, and the primary electron beam for the back scattering electrons follows the trajectory 4-8. The secondary electrons or the back scattering electrons emitting from the sample 4-6 follow the locus indicated by 4-7 and are formed into a parallel beam by the one lens element 4-5a of the doublet lens, which is in turn focused by the other lens element 4-5b of the doublet lens into an image on an image plane 4-12 of the doublet lens. The image of the sample is further magnified by the magnifying lenses 4-3 and 4-2 to form a two-dimensional image on the detecting unit 4-1.

The structure of the electron gun 4-40 will now be described with reference to FIG. 16.

FIG. 16 schematically shows a partial sectional view of the electron gun 4-40 according to one embodiment of the present invention. In FIG. 16, the electron gun 4-40 is illustrated as cut away along the optical axis 4-21.

The electron gun 4-40 of the illustrated embodiment has a structure of rotation symmetry around the optical axis 4-21 and comprises the ring-shaped cathode 4-29 for emitting the primary electron beam defining the hollow beam from the tip portion thereof, the anode 4-22, 4-26 for controlling the direction of the hollow beam emitted from the cathode 4-29 and the Wehnelt 4-22, 4-25 for controlling the beam current value and the convergence condition of the beam, as already described.

The cathode 4-29 is centered around the optical axis 4-21 and extends circumferentially around the optical axis 4-21. The cathode 4-29 comprises an annular support section 4-29a extending in parallel with the optical axis 4-21 in the up-and-down direction in the drawing, an annular step section 4-29b extending inward in the radial direction from the bottom end of the support section 4-29a and an annular emitter section 4-29c extending in parallel with the optical axis 4-21 from the inner end of the step section 4-29b, wherein said support section 4-29a, step section 4-29b and emission section 4-29c are together formed as an integral element. The support section 4-29a is carried by the Wehnelt 4-24 via an annular insulating spacer 4-32 and the support section 4-29a supports the emitter section 4-29c via the step section 4-29c. The emitter section 4-29c defines a tapered tip portion 4-29d in its bottom end and is adapted to emit a hollow beam in a circular ring configuration from this tip portion 4-29d.

The cathode 4-29 is made of hafnium (Hf) assuming a ring-shape whose end surface has been sharpened so that the emission of electrons takes effect exclusively from the tip portion 4-29d. The cathode 4-29 may be made of sintered compact of $LaB_6$, Ta or the like.

The anode 4-22, 4-26 is centered around the optical axis 4-21 and comprises an inner anode 4-22 and an outer anode 4-26. The inner anode 4-22 is disposed in the inside with respect to the cathode 4-29, while the outer anode 4-26 is disposed in the outside with respect to the cathode 4-29.

The inner anode 4-22 is grounded and thus has a potential of zero, defining a ground electrode. On the other hand, the outer anode 4-26 is adapted to be applied with a voltage of any desired value, wherein a potential difference produced between the inner anode 4-22 and the outer anode 4-26 can control the direction of the hollow beam emitted from the cathode 4-29.

The inner anode 4-22 comprises a zero potential electrode section 4-22a for controlling the direction of the hollow beam and a support section 4-22b for producing the zero potential over the optical axis, said zero potential electrode section 4-22a and said support section 4-22b together defining an integral element. The support section 4-22b is formed into a circular cylindrical configuration extending in one direction in parallel with the optical axis 4-21 and fixed to the housing of the electron beam apparatus by using a member that is not shown in the drawing. The zero potential electrode 4-22a is formed into an annular and flat plate extending from the bottom end of the support section 4-22b in the direction orthogonal to the optical axis 4-21 and outwardly in the radial direction.

The outer anode 4-26 is disposed on the radially outside with respect to the inner anode 4-22 and extends circumferentially around the optical axis 4-21, thus defining an annular structure. Further, the outer anode 4-26 is disposed on the radially outside with respect to the inner anode 4-22 with a space placed therebetween, which defines an annular path 4-22 allowing the hollow beam to pass therethrough.

The outer anode 4-26 comprises an electrode section 4-26a for controlling the direction of the hollow beam and a support section 4-26b for supporting the electrode section 4-26a, said zero potential electrode section 4-22a and said support section 4-26b together defining an integral element as insulated from each other.

The support section 4-26b is formed into a circular cylinder extending in parallel with the optical axis 4-21 and fixed to the housing of the electron beam apparatus as insulated therefrom by using a member that is not shown in the drawing. The support section 4-26b of the outer anode 4-26 extends along and in parallel with the support section 4-22b of the inner anode 4-22. Further, the support section 4-26b is disposed radially outside of the support section 4-22b with a space placed therebetween, in which the cathode 4-29, the Wehnelt 4-24, 4-25 and other elements are arranged.

The electrode section 4-26a is formed into an annular and flat plate extending from the bottom end of the support section 4-26b in the direction orthogonal to the optical axis 4-21 and inward in the radial direction. Further, the electrode section 4-26a is opposite to the flat-plate section 4-22a of the inner anode 4-22 to be flush therewith via the annular path 4-22c interposed therebetween.

The inner anode 4-22 is grounded or earthed as explained previously, and this arrangement prevents the potential of the electron gun 4-40 from affecting the locus of the secondary electrons on the optical axis. The outer anode 4-26 is insulated from the inner anode 4-22, and so the application of the voltage different from the ground to the outer anode 4-26 can control the hollow beam defining the primary electron beam appropriately such that the emission of the beam can be directed to the inward 4-31 direction or the outward 4-30 direction and/or the beam can be formed into a convergent beam or a divergent beam. In this connection, if the beam is to be guided in the direction of 4-31, a negative voltage should be applied to the outer anode 4-26, or if the beam is to be guided in the direction of 4-30, a positive voltage should be applied to the outer anode 4-26. In this way, the annular path 4-22c has a certain width in the radial direction so as to permit the control for changing the direction of the hollow beam to be carried out with some allowable angle range. The cathode 4-29 is positioned such that the tip portion thereof 4-29d is in the same radial position as the annular path 4-22 so that the angle range determining the direction of the hollow beam can be changed as much as possible.

The Wehnelt 4-24, 4-25 is formed into an annular configuration centered around the optical axis 4-21, extending in parallel with the optical axis 4-21 with its width expanded toward the bottom in the drawing.

The Wehnelt 4-24, 4-25 comprises an inner Wehnelt 4-24 and an outer Wehnelt 4-25. The inner Wehnelt 4-24 is disposed in the inside with respect to the cathode 4-29, and the outer Wehnelt 4-25 is disposed on the outside with respect to the cathode 4-29.

The inner Wehnelt 4-24 comprises an electrode section 4-24a for controlling the emission of the primary electron beam and a support section 4-24b for supporting the electrode section 4-24a, said electrode section 4-24a and said support section 4-24b together defining an integral element. The support section 4-24b comprises a circular cylindrical section 4-24b1 extending in parallel with the optical axis 4-21 and a truncated cone section 4-24b2 extending from the bottom end of the circular cylindrical section at an angle toward the radially inward direction. The electrode section 4-24a defines a circular cylindrical configuration extending from the bottom end of the truncated cone section 4-24b2 in parallel with the optical axis 4-21.

The outer Wehnelt 4-25 has an electrode section 4-25a for controlling the emission of the primary electron beam and a support section 4-25b for supporting the electrode section 4-25a, said electrode section 4-25a and said support section 4-25b together defining an integral element. The electrode section 4-25a is supported by the inner Wehnelt 4-24 via an insulation spacer that is not shown in the drawing. The support section 4-25b is disposed on the radially outside with respect to the support section 4-24b of the inner Wehnelt 4-24 and defines a space therebetween, in which the tip portion 4-29d of the cathode is arranged. The support section 4-25b comprises a circular cylindrical section 4-25b1 extending in parallel with the optical axis 4-21 and a truncated cone section 4-25b2 extending from the bottom end of the circular cylindrical section at an angle toward the radially outward direction. Thus, the truncated cone section 4-25b2 of the outer Wehnelt 4-25 and the truncated cone section 4-24b2 of the inner Wehnelt 4-24 together secure a space expanding toward downstream side of the tip portion 4-29d of the cathode so as to prevent the divergence of the hollow beam emitted from the tip portion 4-29d of the cathode.

The configuration of the Wehnelt 4-24, 4-25 may be determined through the simulation. The Wehnelt 4-24, 4-25 can be used to control the primary electron beam in a similar manner to the anode 4-22, 4-26 by insulating the inner Wehnelt 4-24 from the outer Wehnelt 4-25 and applying a voltage different from the ground to the outer Wehnelt 4-25 so that the emission of the primary electron beam can be guided in the inward direction 4-31 or outward direction 4-30. The control of the emission direction of the primary electron beam is carried out only by the anode 4-22, 4-26. The Wehnelt 4-24, 4-25 has a function for controlling the beam amount and preventing the divergence of the beam.

The electron gun 4-40 may further comprise a sub-cathode 4-28 and a shield 4-27 for the sub-cathode 4-28. The sub-cathode 4-28 has an annular configuration centered around the optical axis 4-21 and is disposed on the radially outside with respect to the cathode 4-29. The sub-cathode 4-28 is made of tungsten filament and is disposed on the outside with respect to the cathode 4-29 with a certain distance placed therebetween in the circumferential direction centered on the optical axis 4-21. The shield 4-27 for the sub-cathode 4-28 is a shield serving for directing all of the electrons from the sub-cathode 4-28 into the cathode 4-29 and may be applied with a voltage of 20.1 kV, for example.

The insulation spacer 4-23 couples the inner Wehnelt 4-24 with the inner anode 4-22 and the insulation spacer 4-32 couples the cathode 4-29 with the inner Wehnelt 4-24. The reason they have different diameters resides in that the longer insulation length should be secured so as to avoid discharging.

A general operation of the electron gun 4-40 according to the illustrated embodiment will now be described.

A voltage around −20 kV is applied to the cathode 4-28 to cause an electro-bombardment toward the cathode 4-29 (the electro-bombardment method is one of the known methods for degassing the components such as an electrode in an ion source for an ionization vacuum gauge or a mass spectrometer with a hot-cathode. A detailed description can be found in the Japanese Patent Laid-open Publication No. Hei 06-150875, for example.) so as to induce a current flow of about 1 mA to thereby heat the cathode 4-29 with the power of $(20-4.5) \times 10^3 \times 1 \times 10^{-3}$ W. In this stage, the cathode 4-29 is applied with the voltage of −4.5 kV. Through this procedure, the primary electron beam is emitted from the cathode. The emission direction of the primary electron beam can be controlled by applying the voltage different from the ground to the outer anode 4-26.

Since such an electron gun 4-40 as described above has a large cathode 4-29 area on the order of $10 \,\mu m \times 2 \,\pi \times 3 \,mm \approx 2 \times 10^{-1} \,mm^2$ and advantageously the tip portion of the cathode 4-29 can be applied with an intensive electric field, the primary electron beam of high intensity can be extracted. Therefore, with such an electron gun, it becomes possible to irradiate the beam having the beam current of some mA onto an area having a diameter as large as 200 μm without any problem, which allows the image projection optical system to be actuated in the very bright environment and thus helps increase the number of electrons per pixel, resulting in an image of good S/N ratio to be obtained. Furthermore, since this irradiation method can eliminate the use of the E×B separator, there would be induced no chromatic aberration from deflection in the image of secondary electron beam which otherwise could have caused by the E×B separator. Since this arrangement further eliminates the use of the obliquely installed primary optical system, the mechanical resonance frequency can be increased to make the apparatus more robust to the vibrations. Further, as clearly seen from FIG. 15, the primary electron beam has its passage in the outside to the locus 7 of the secondary electron beam, and so there would be no chance that the space charge from the primary electron beam stimulates the out-of-focus of the secondary electron beam. The omission of the primary optical system can reduce costs by just that much.

SIXTH EXAMPLE

Figure 17:
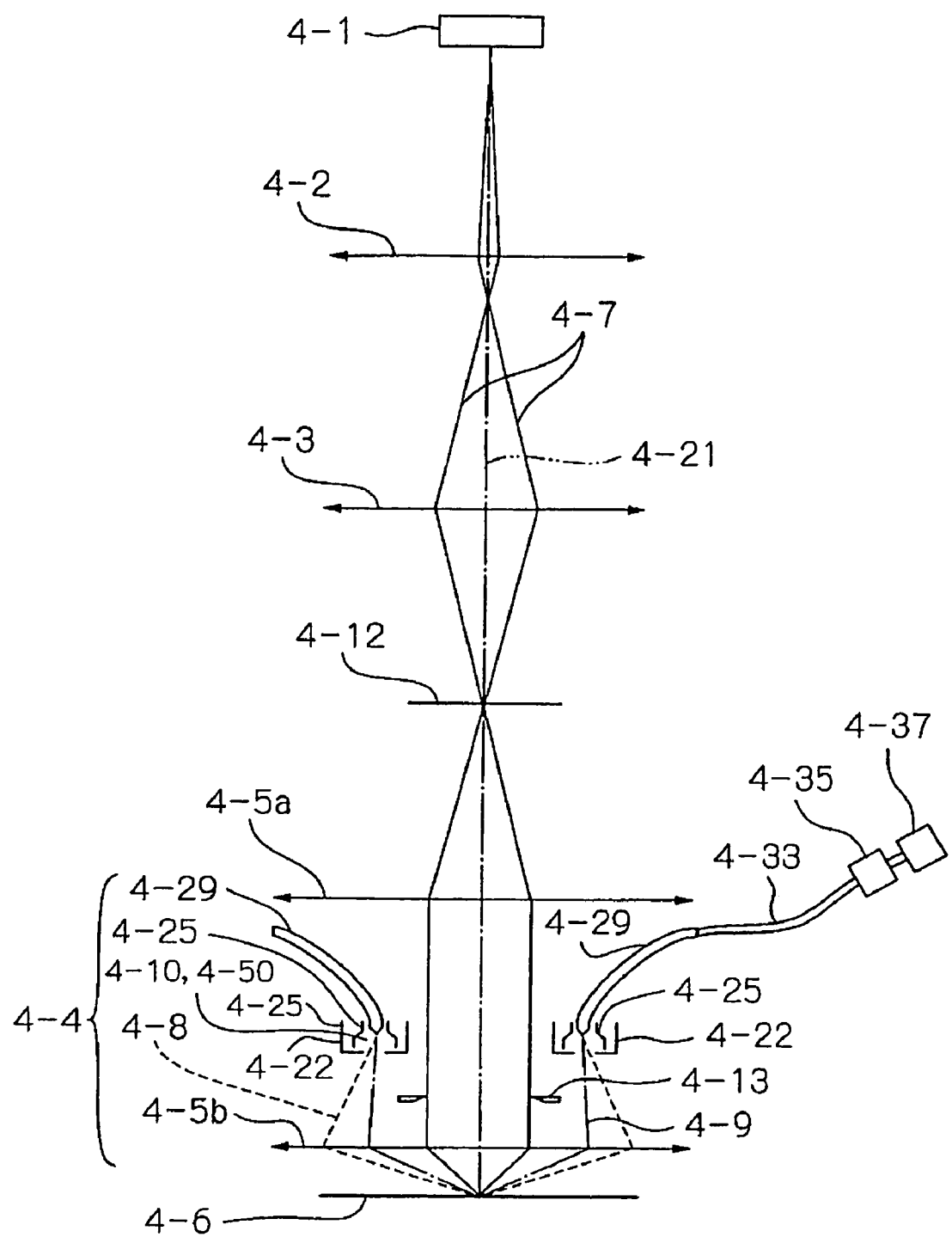
FIG. 17 is a diagram schematically illustrating a formation of an focused image in an electron beam apparatus with a image-projection optical system according to another embodiment of the fourth invention.
Figure 18:
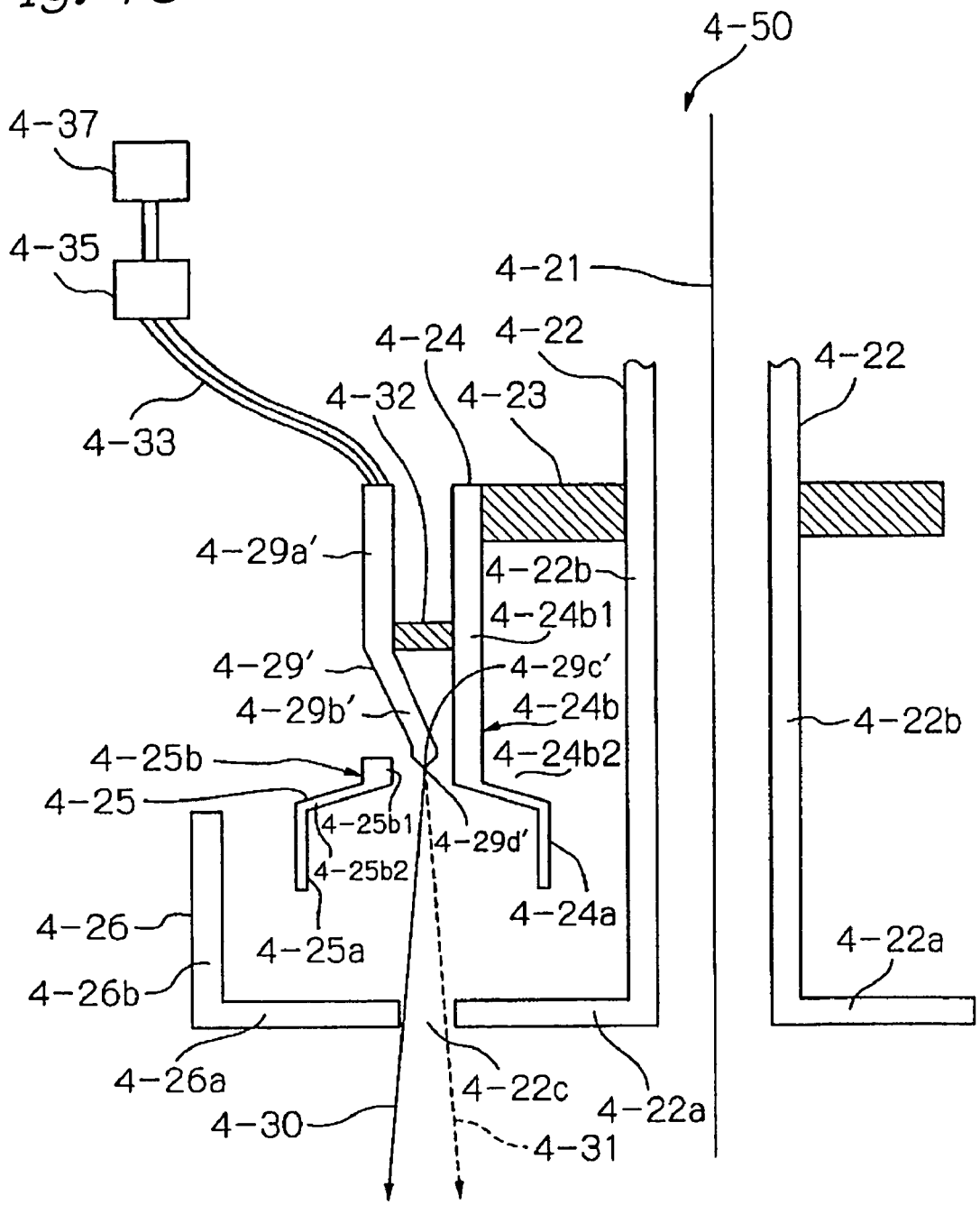
FIG. 18 is a fragmentally sectional view schematically showing an electron gun according to another embodiment of the fourth invention.

FIG. 17 shows an electron beam apparatus of image projection optical system focusing a beam into an image according to another embodiment of the fourth invention. Elements similar to those in the first embodiment are designated by the same reference numerals and the detailed explanation thereof is hereby omitted but the description is only given of different points. The electron beam apparatus according to the second embodiment is different in comparison with the first embodiment in that a different type of electron gun is used. As it is, the electron gun according to the illustrated embodiment will now be described with reference to FIG. 18.

Although the electron gun 4-40 of the first embodiment has employed the configuration in which the cathode 4-29 is heated by the sub-cathode 4-28 so as to emit the primary electron beam, the present embodiment has employed a photo-cathode 4-29 taking advantage of photoelectric effect to emit the primary electron beam. Owing to this, an electron gun 4-50 according to the present embodiment is different from the electron gun 4-40 according to the first embodiment in the configuration and material of the cathode 4-29. Further, instead of the sub-cathode 4-28 and the shield 4-27, the electron gun 4-50 comprises an optical fiber 4-33, a longer-wave cut filter 4-35 and a high pressure mercury lamp 4-37.

A cathode 4-29' of the electron gun 4-50 according to the second embodiment is centered on the optical axis 4-21 and extends circumferentially around the optical axis 4-21. The cathode 4-29' comprises an annular support section 4-29a' extending in parallel with the optical axis 4-21 in the up-and-down direction in the drawing, a truncated cone section 4-29b' extending at an angle toward the radially inward direction from the bottom end of the support section 4-29a', and an annular emitter section 4-29c' extending in parallel with the optical axis 4-21 from the inner end of the truncated cone section 4-29b', said support section 4-29a', truncated cone section 4-29*b*' and emitter section 4-29*c*' defining an integral element. The support section 4-29*a*' is supported by the Wehnelt 4-24 via the annular insulation spacer 4-32 and it supports the emitter section 4-29*c*' via the truncated cone section 4-29*b*'. The emitter section 4-29*c*' defines a tapered tip portion 4-29*d*' in the bottom end thereof, from which a hollow beam in a circular ring configuration is emitted. The cathode 4-29' is made of silica glass with its tip portion coated with platinum in the ring-shape and with its inner and outer sides vapor-deposited with aluminum.

The optical fiber 4-33 is connected at its one end to the top end of the support section 4-29*a*' of the cathode 4-29' while the other end thereof is connected to the long-wave cut filter 4-35. Further, the high pressure mercury lamp 4-37 is coupled to the long waver cut filter 4-35.

The light emitted from the high pressure mercury lamp 4-37 has its long-wave components filtered out by the long-wave cut filter 4-35 and then guided through the optical fiber 4-33 into the cathode 4-29'. When the light enters the cathode 4-29' and thus the photoelectric material, platinum, the photoelectric effect is developed and thereby the primary electron beam is emitted from the tip portion 4-29*d*'.

The use of the photo-cathode can solve the problem of temperature rise resultant from the heating of the cathode 4-29 to induce the emission of the primary electron beam.

SEVENTH EXAMPLE

An overview of an electron beam apparatus according to an embodiment of the fifth invention will now be presented.

Figure 19:
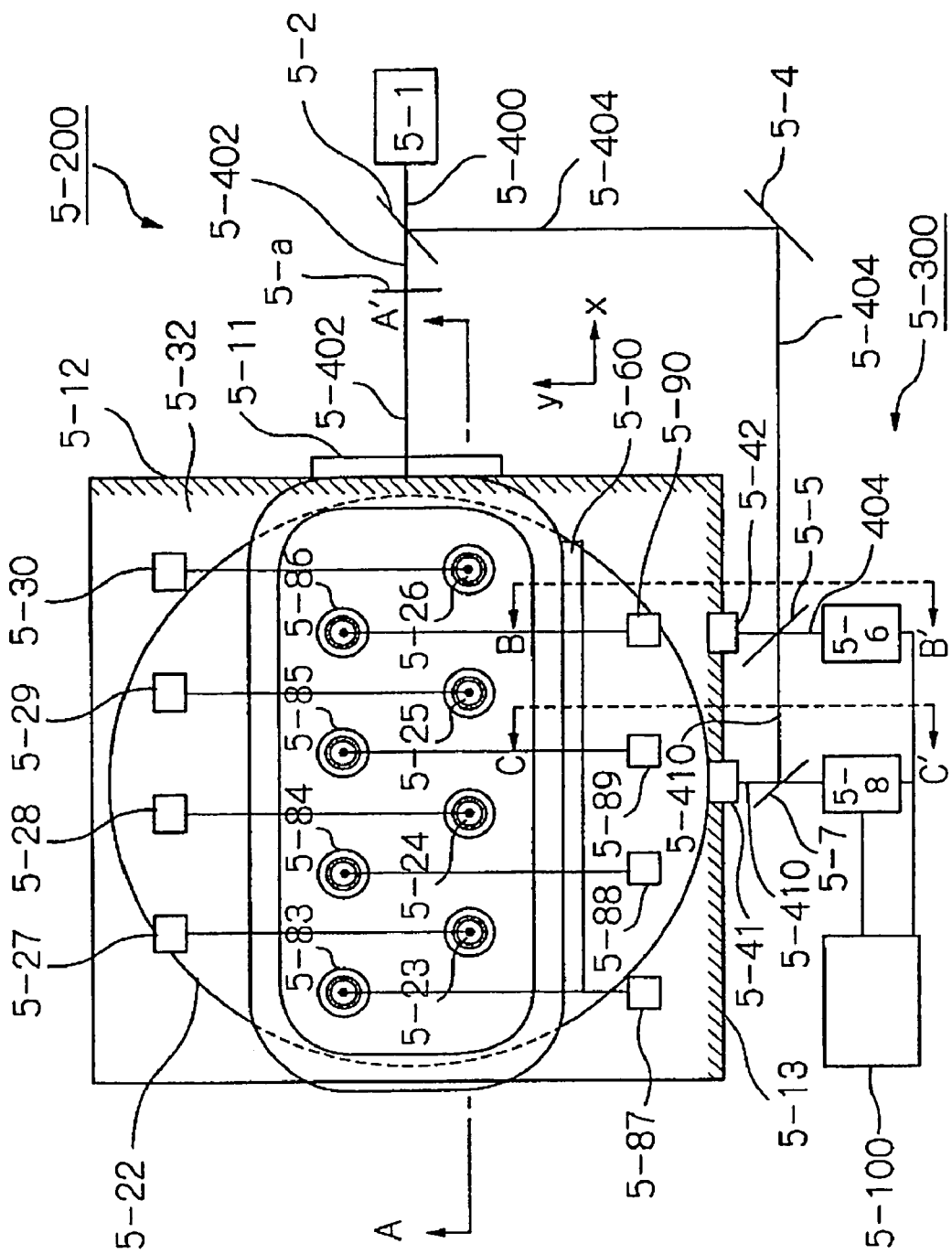
FIG. 19 is a schematic plan view of a position measuring device for a sample table in an electron beam apparatus according to an embodiment of a fifth invention.
Figure 20:
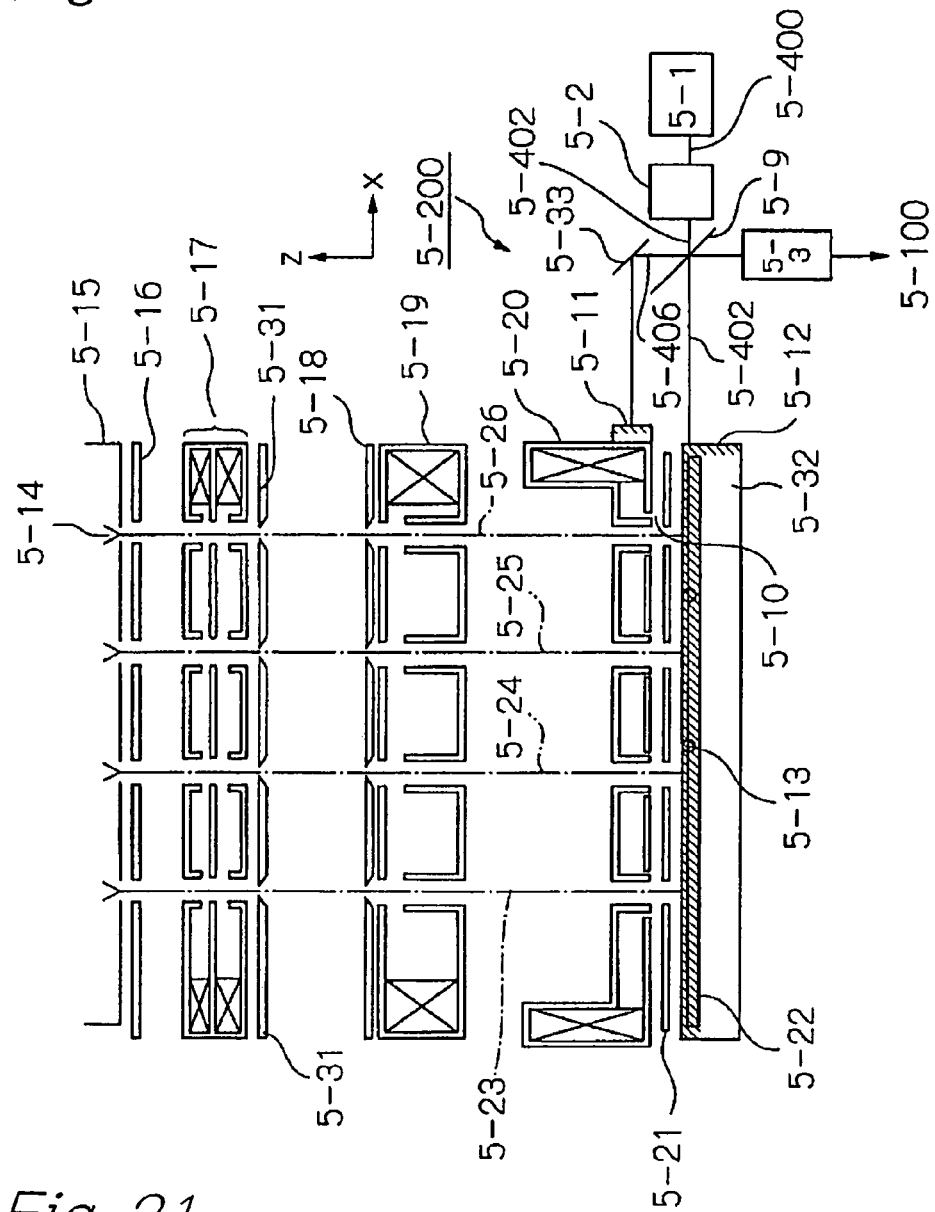
FIG. 20 is a schematic sectional view taken along the A-A' line of FIG. 19.

FIGS. 19 and 20 show a position measuring device for a sample table of an electron beam apparatus according to an embodiment of the present invention. FIG. 19 is a plan view and FIG. 20 is a schematic sectional view taken along the A-A' line of FIG. 19.

The position measuring device of the illustrated embodiment is provided to measure a position of the sample table of the electron beam apparatus.

The electron beam apparatus irradiates a plurality of primary electron beams having a plurality of optical axes over a sample 5-22 loaded on a sample table 5-32 adapted to be movable along the x-y plane having the x-axial direction and the y-axial direction.

The position measuring device of the illustrated embodiment comprises a laser source 5-1 for emitting a laser beam 5-400, a first splitting device 5-2 for splitting the laser beam 5-400 emitted from the laser source 5-1 into two separate laser beams 5-402 and 5-404, a first measuring device 5-200 for measuring the position of the sample table 5-32 along the x-axial direction by using one of the two separate laser beams or a first laser beam 5-402, a second measuring device 5-300 for measuring two positions of the sample table 5-32 along the y-axial direction by using the other 5-404 of the two separate beams, and a controller 5-100 for detecting a rotational amount of the sample table 5-32 in the x-y plane based on the measurement from the second measuring device 5-300.

The first splitting device 5-2 comprises a beam splitter 5-2 in the present embodiment. The beam splitter 5-2 is operable to split the laser beam emitted from the laser source 5-1 into the first laser beam 5-402 and the second laser beam 5-404.

The first measuring device 5-200 comprises a x-movable laser mirror 5-12 serving as a first reflecting mirror disposed along the y-axial direction in the sample table 5-32, a first guiding device 5-9 for guiding the first laser beam 5-402, that has been split in the beam splitter 5-2, toward the x-movable laser mirror 5-12, a laser receiver 5-3 serving as a first receiver for receiving the first laser beam reflected by the first reflecting mirror 5-12, and a x-directional stationary laser mirror 5-11 serving as a first stationary mirror installed on a sidewall of an objective lens 5-20 of the electron beam apparatus disposed above the sample table 5-32, at a location on said sidewall defined in the x-movable laser mirror 5-12 side thereof.

The first guiding device 5-9 comprises the first beam splitter 5-9 in the illustrated embodiment. The beam splitter 5-9 is operable to guide the first laser beam 5-402 split in the beam splitter 5-2 toward the first reflecting mirror 5-12, while splitting a fourth laser beam 5-406 from the first laser beam 5-402.

The first measuring device further comprises a laser mirror 5-33 serving as a first laser mirror for reflecting the fourth laser beam 5-406 to be irradiated toward the x-directional stationary laser mirror 5-11.

The position measuring device of the present embodiment further comprises a laser reflector 5-4 for reflecting the second laser beam 5-404 split in the beam splitter 5-2, toward the second measuring device 5-300. The laser reflector 5-4 guides the other laser beam 5-404 split in the beam splitter 5-2 and directed along the y-axial direction, into the second measuring device 5-300. The position measuring device of the illustrated embodiment includes the laser reflector 5-4 for the reason that it has only one laser source.

A second measuring device 5-300 comprises a beam splitter 5-5 for splitting a third laser beam 5-410 from the second laser beam 5-404 reflected by the laser reflector 5-4, a y-moving laser mirror 5-13 serving as a second reflecting mirror disposed along the x-axial direction in the sample table 5-32, a laser mirror 5-7 serving as a third guiding device for guiding the third laser beam 5-410 split in the beam splitter 5-5, toward the y-movable laser mirror 5-13, a laser receiver 5-6 serving as a second receiver for receiving the second laser beam 5-404 reflected by the y-movable laser mirror 5-13, and a laser receiver 5-8 serving as a third receiver for receiving the third laser beam 5-410 reflected by the y-moving laser mirror 5-13. The beam splitter 5-5 is also serving as a second guiding device for guiding the second laser beam 5-404 toward the y-moving laser mirror 5-13.

The second measuring device 5-300 comprises a y-directional stationary laser mirror 5-60 serving as a second stationary mirror installed on a sidewall of the objective lens 5-20 of the electron beam apparatus, at a location on said sidewall defined in the y-moving laser mirror 5-13 side thereof, a beam splitter 5-42 for guiding the second laser beam 5-404 from the beam splitter 5-5 toward the y-moving laser mirror 5-13, while splitting a fifth laser beam 5-412 from the second laser beam 5-404, a second laser mirror 5-62 for reflecting the fifth laser beam 5-412 to be irradiated toward the y-directional stationary laser mirror 5-60, a beam splitter 5-41 serving as a third beam splitter for guiding the third laser beam 5-410 reflected by the laser mirror 5-7, toward the y-moving laser mirror 5-13, while splitting a sixth laser beam 5-414 from the third laser beam 5-410, and a third laser mirror 5-63 for reflecting the sixth laser beam 5-414 to be irradiated onto the y-directional stationary laser mirror 5-60.

The electron beam apparatus for evaluating the sample 5-22 comprises eight optical axes indicated by 5-23, 5-24, 5-25, 5-26, 5-83, 5-84, 5-85 and 5-86 above the sample 5-22 fixedly loaded on the sample table 5-32. A set of elements including an electron gun consisting of a ZrO/W cathode 5-14, a Schottky shield 5-15 and an anode 5-16, a condenser lens 5-17 capable of controlling a rotation of a primary electron beam emitted from the electron gun, a multi-aperture 5-31, an NA aperture 5-18, a reduction lens 5-19 and an objective lens 5-20 is arranged along each of the eight optical axes on a single sample 5-22. In the evaluation of the sample 5-22, the eight primary electron beams are driven concurrently in the x-direction to perform the scanning motion, while driving an actuator, though not shown, so as to move the sample table 5-32 continuously in the y-direction, and secondary electron beams emanating from the scanning points are accelerated by an axisymmetric electrode 5-21. The axisymmetric electrode 5-21 is disposed below the objective lens 5-20 and formed to be axisymmetric in the vicinity of each optical axis. The secondary electron beams accelerated by the axisymmetric electrode 5-21 are converged by the objective lens 5-20 having a gap defined in the sample 5-22 side thereof and deflected by an E×B separator, though not shown, in the direction deviating from the optical axis into corresponding detectors, 5-27, 5-28, 5-29, 5-30, 5-87, 5-88, 5-89, 5-90, where they are detected. Four secondary electron beams which are equally spaced from any adjacent beams when projected on the y-axis are produced for each optical axis, and each of those four secondary electron beams is detected independently by each associated detector. The SEM image by 32 channels is generated from secondary electron signal by 8×4=32 channels from those detectors, so that the evaluation of the sample with high throughput can be carried out, while at the same time, movement of the sample table can be reduced because the sample table is only required to move in the x-direction by a distance equivalent to an interval between the adjacent optical axes.

In the position measuring device according to the present embodiment, the x-movable laser mirror 5-12 is formed by a surface of the sample table oriented in parallel with the y-axis, which has been mirror polished, and the y-movable laser mirror 5-13 is formed by a surface of the sample table oriented in parallel with the x-axis, which has been mirror polished. When the sample table is made of silicon carbide ceramics, which include many voids, such a material having substantially no void, including ZrO, highly purified alumina and silica, may be first attached onto the side surface of the sample table and then the resultant surface may be mirror polished.

The laser beam 5-400 emitted from the laser oscillator 5-1 is split by the beam splitter 5-2 into the first laser beam 5-402 that is advanced straight for the x-measurement and the second laser beam 5-404 that is reflected in the y-axial direction for the y-measurement. The first laser beam 5-402 is split by the beam splitter 5-9 into two beams, the first laser beam 5-402 and the fourth laser beam 5-406. The fourth laser beam 5-406 is reflected at a right angle by the laser mirror 5-33 and irradiated on the stationary laser mirror 5-11 installed on the outside of the objective lens 5-20. The fourth laser beam 5-406 reflected by the stationary laser mirror 5-11 is further reflected by the laser mirror 5-33 to be advanced straight through the beam splitter 5-9 into the laser receiver 5-3. On the other hand, the first laser beam 5-402 transmitted through the beam splitter 5-9 is reflected by the x-moving laser mirror 5-12 installed in the sample table 5-32 and then reflected by the beam splitter 5-9 to enter the laser receiver 5-3. The speed of the moving mirror can be measured by the interference of the fourth laser beam 5-406 from the stationary laser mirror 5-11 with the first laser beam 5-402 from the x-moving laser mirror 5-12. This speed may be integrated by a counter installed in the laser receiver 5-3. More specifically, a fluctuation of the signal resultant from the interference of the first laser beam 5-402 from the x-moving laser mirror 5-12 with the fourth laser beam 5-406 reflected by the stationary laser mirror 5-11 is converted into a pulse form, from which the speed of the moving mirror is calculated and the calculated speed is further integrated so as to determine a travel distance of the sample table in the x-axial direction.

On the other hand, the second laser beam 5-404 split by the beam splitter 5-2 is reflected at a right angle by the laser reflector 5-4 and split by the beam splitter 5-5 into two beams, the second laser beam 5-404 and the third laser beam 5-410.

Figure 21:
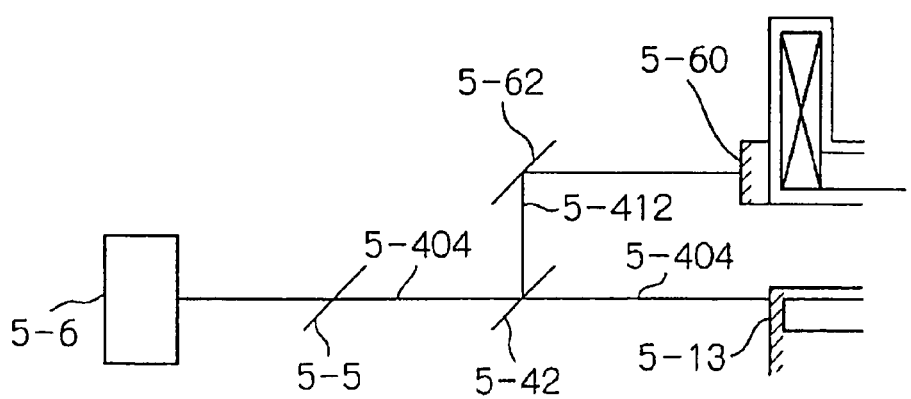
FIG. 21 is a schematic sectional view taken along the B-B' line of FIG. 19.

The second laser beam 5-404 is split by the beam splitter 5-42 into the second laser beam 5-404 and the fifth laser beam 5-412 as shown in FIG. 21. The fifth laser beam 5-412 is reflected at a right angle by the second laser mirror 5-62 and irradiated on the y-directional stationary laser mirror 5-60 installed on the outside of the objective lens 5-20. The fifth laser beam 5-412 reflected by the stationary laser mirror 5-60 is further reflected by the second laser mirror 5-62 and the beam splitter 5-42 and advanced straight through the beam splitter 5-5 into the laser receiver 5-6. On the other hand, the second laser beam 5-404 transmitted through the beam splitter 5-42 is irradiated onto and thus reflected by the y-moving laser mirror 5-13 installed on the sample table 5-32 and advanced straight through the beam splitters 5-42 and 5-5 into the laser receiver 5-6. A fluctuating signal is produced from the interference of the laser beam from the y-directional stationary laser mirror 5-60 with the laser beam from the y-moving laser mirror 5-13, and this signal is shaped into the pulse form, which is in turn counted to determine the speed of the movable mirror. This speed is integrated by the counter installed in the laser receiver 5-6 and similarly the travel distance of the sample table in the y-axial direction is calculated.

Figure 22:
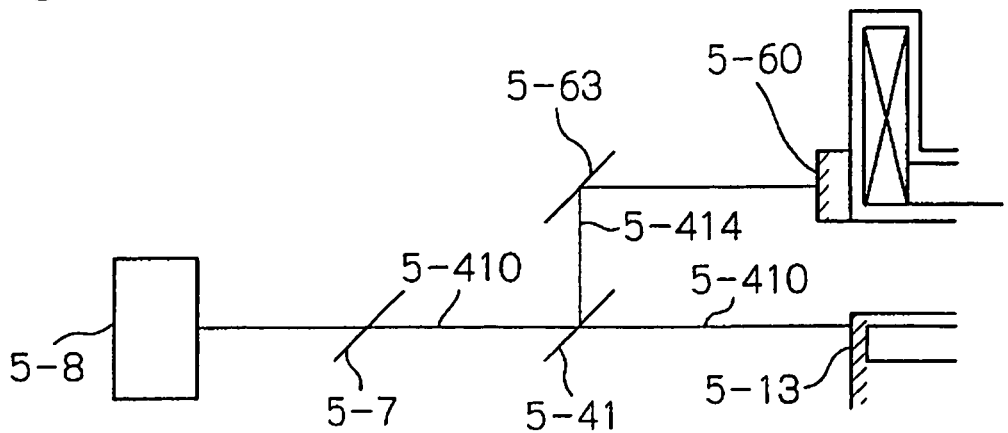
FIG. 22 is a schematic sectional view taken along the C-C' line of FIG. 19.

Further, although FIG. 21 only shows an optical path of the second laser beam, behind that of the second laser beam, the third laser beam 5-410 follows a similar optical path as shown in FIG. 22. The third laser beam 5-410 is reflected at a right angle by the beam splitter 5-7 and then split by the beam splitter 5-41 into the third laser beam 5-410 and the sixth laser beam 5-414. The sixth laser beam 5-414 is reflected at a right angle by the third laser mirror 5-63 and then reflected by the y-directional stationary laser mirror 5-60 installed on the outside of the objective lens 5-20, and the beam is further reflected by the third laser mirror 5-63 and the beam splitter 5-41 and then advanced straight through the beam splitter 5-7 into the laser receiver 5-8. On the other hand, the third laser beam 5-410 transmitted through the beam splitter 5-41 is reflected by the y-moving laser mirror 5-13 installed on the sample table 5-32 and advanced straight through the beam splitter 5-41 and 5-7 into the laser receiver 5-8. The fluctuating signal is obtained by the interference of the laser beam from the y-directional stationary laser mirror 5-60 with the laser beam from the y-moving laser mirror 5-13, and the obtained signal is shaped into the pulse form, which is in turn counted to thus measure the speed of the moving mirror. This speed is integrated by the counter installed in the laser receiver 5-8 and similarly the travel distance of the sample table in the y-axial direction can be calculated.

The values calculated in the laser receivers 5-3, 5-6, 5-8 are sent to the controller 5-100, which determines the rotational amount of the sample table 5-32 within the x-y plane based on the calculated values of the positions of the sample table 5-32 measured at the two locations by the y-axis directional laser beam.

Figure 23:
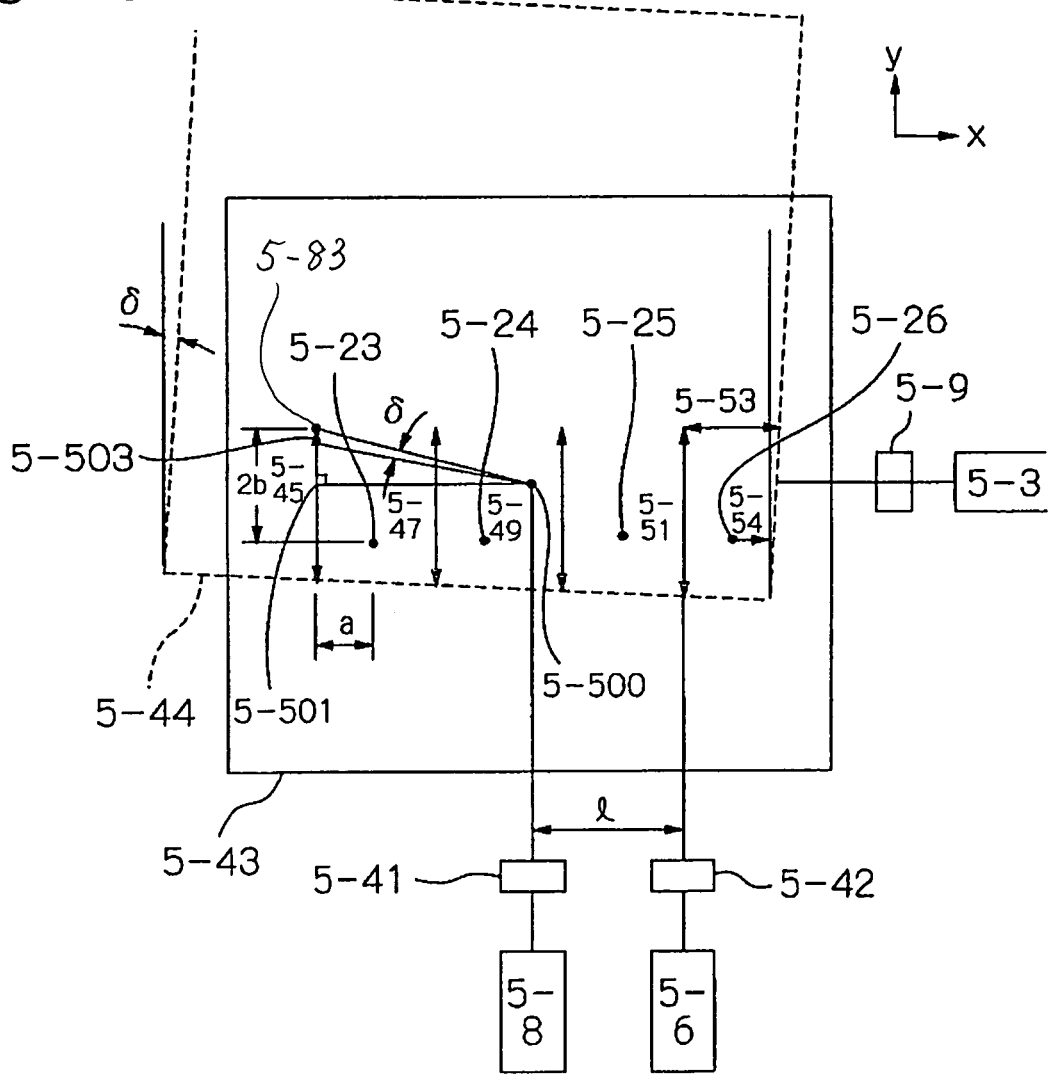
FIG. 23 is a diagram illustrating how to compensate for the Yaw motion according to the present invention.

The correction method for Abbe's error according to the present invention will now be described. Reference numerals 5-41, 5-42 found in FIG. 23 designate the beam splitter 5-41, 5-42 shown in FIG. 19, each of which is composed of a translucent mirror for splitting the laser beam into two beams, one directed to the y-directional stationary laser mirror 5-60 installed on the outside of the objective lens 5-20 and the other directed to the y-moving laser mirror 5-13 on the sample table 5-32. Reference numeral 5-43 presents an ideal orientation of the sample table 5-32, and reference numeral 5-44 presents the orientation of the sample table 5-32 at the moment when the Yaw motion of the sample table has been triggered from the tolerance in moving the sample. The difference in readings of the y-coordinate of the sample table 5-32 measured by the laser receivers 5-8 and 5-6 is divided by the value of spacing, 1, between the beam splitters 5-41 and 5-42, and the rotational amount δ(radian) for the sample table 5-32 can be calculated.

Assuming that a distance in the y-axial direction between adjacent optical axes (e.g., the optical axis 5-83 and the optical axis 5-23) is denoted as "2b" and a distance in the x-axial direction between said adjacent optical axes is denoted as "a". It is also assumed that the rotational amount δ of the sample table 5-32 is measured in a clockwise rotation. A difference in the readings of the coordinate by the x-directional laser measuring device 5-3 and the y-directional laser measuring device 5-8 can be determined in the following manner. Although the sample table is rotated by δ in the clockwise direction in FIG. 23, there is no error produced from the rotation at the intersection 5-500 of the x-laser axis 5-3 with the y-laser axis 5-8. The error induced by the rotation at a certain point increases as it goes farther from the intersection 5-500.

The sample table coordinate subject to the irradiation of the optical axis 5-83 is represented by the coordinate 5-503 that has been rotated in the counter-clockwise direction by δ around the intersection 5-500 from the readings of the laser measuring devices 5-3 and 5-8. If the value of δ is small, the triangle (5-83, 5-503, 5-502) is analogous to the triangle (5-500, 5-501, 5-502), and the angle (5-503, 5-83, 5-502) is represented by Δ. The distance between the point 5-83 and the point 5-503 is:

$$\sqrt{(2.5a)_2 + b^2} \cdot \delta \qquad \text{(Equation 1)}$$

Figure 24:
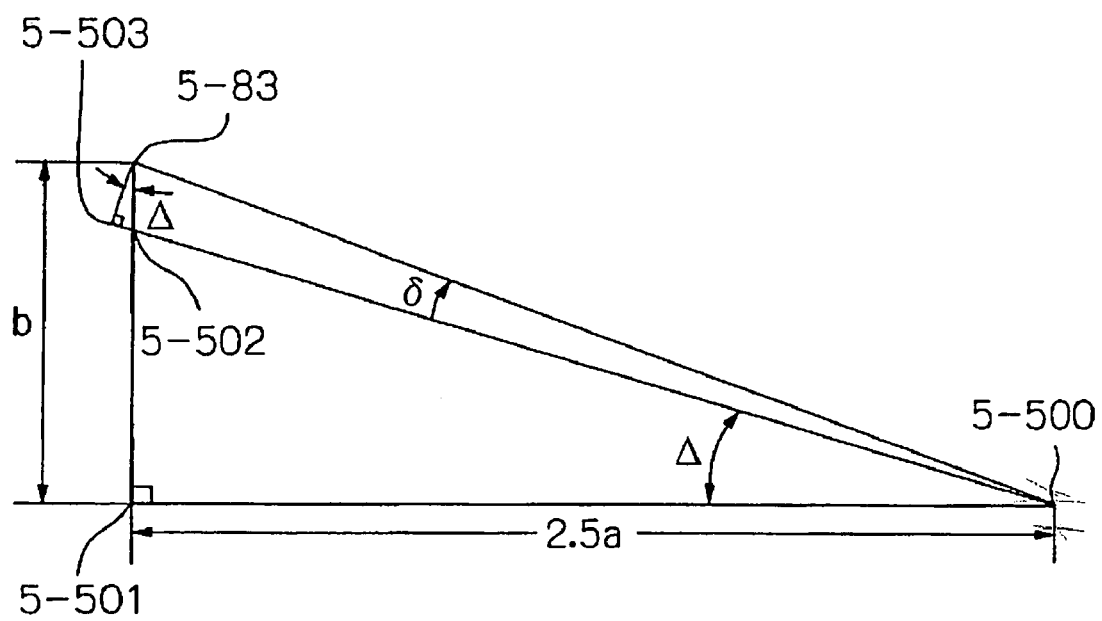
FIG. 24 is a partial enlarged view of FIG. 23.

The quantity of correction for the y-coordinate of the optical axis 5-83 is determined from FIG. 24 in the following equation:

$$b - \sqrt{(3.5a)^2 + b^2} \cdot \delta \cdot \cos\Delta = \qquad \text{(Equation 2)}$$
$$b - \sqrt{(3.5a)^2 + b^2} \cdot \delta \cdot \frac{3.5a}{b - \sqrt{(3.5a)^2 + b^2}} = b - 3.5a\delta$$

On the other hand, the quantity of correction for the x-coordinate is determined from FIG. 24 in the following equation:

$$\sqrt{(3.5a)^2 + b^2} \cdot \delta \cdot \sin\Delta = \qquad \text{(Equation 3)}$$
$$\sqrt{(3.5a)^2 + b^2} \cdot \delta \cdot \frac{b}{\sqrt{(3.5a)^2 + b^2}} = b\delta$$

The quantity of correction for the y-coordinate of the optical axis 5-23 is similarly determined to be
−b−2.5aδ,
and the quantity of correction for the x-coordinate turns to be
+bδ.

The correction amount to the y-coordinate for the optical axis 5-84 is determined to be
b−1.5aδ,
and the correction amount to the x-coordinate turns to be
−bδ.

The quantity of correction for the y-coordinate of the optical axis 5-24 is determined to be
−b−0.5aδ,
and the quantity of correction for the x-coordinate turns to be
bδ.

The quantity of correction for the y-coordinate of the optical axis 5-85 is determined to be
b−0.5aδ,
and the quantity of correction for the x-coordinate turns to be
−bδ.

The quantity of correction for the y-coordinate of the optical axis 5-25 is determined to be
−b+1.5aδ,
and the quantity of correction for the x-coordinate turns to be
bδ.

The quantity of correction for the y-coordinate of the optical axis 5-86 is determined to be
b+2.5aδ,
and the quantity of correction for the x-coordinate turns to be
−bδ.

The quantity of correction for the y-coordinate of the optical axis 5-26 is determined to be
b+3.5aδ,
and the quantity of correction for the x-coordinate turns to be
bδ.

EIGHTH EXAMPLE

Figure 25:
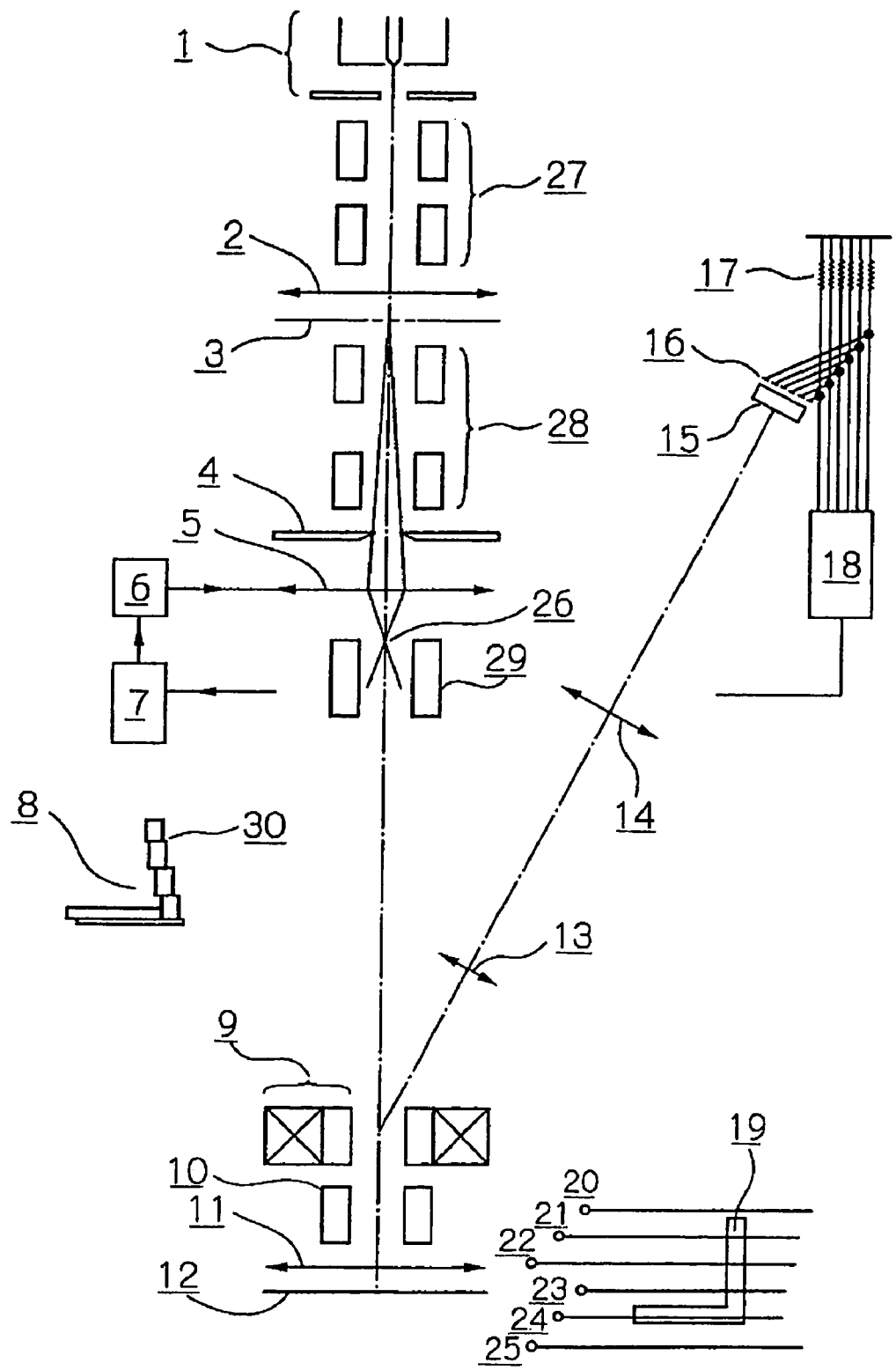
FIG. 25 is a diagram schematically showing an electron optical column used in a pattern evaluation method of a sixth invention.

FIG. 25 is a schematic diagram illustrating an electron optical system used in a pattern evaluation method in a first embodiment of the sixth invention. An electron beam emitted from an electron gun 1 is axially aligned by an axial-aligning deflector 27 with a condenser lens 2 and a multi-aperture 3. A beam having passed through the multi-aperture is axially aligned by an axial-aligning deflector 28 with an NA aperture 4 and a reduction lens 5. The multi-aperture forms the beam into a reduced image at the point of 26 and the beam is further focused by an objective lens 11 into an image of a multi-beam consisting of 6 to 20 beam elements on a sample 12. The multi-beam is driven by a two-stage of deflectors 29 and 10 to scan the sample 12 in on-axial direction across a range equivalent to the width of a stripe, while the scanning operation by the deflector and the moving of the sample table are carried out in the other-axial direction, to thereby obtain a two-dimensional image. Secondary electrons emanating from the sample 12 are accelerated and converged by the objective lens 11, and separated from the primary optical system by an E×B separator 9 into the secondary optical system, where an electron image is magnified by magnifying lenses 13 and 14, multiplied by a MCP detector 15, absorbed by a multi-anode 16, and converted into an electric signal by a resistor 17, with which a two-dimensional image is formed by an amplifier·A/D converter and image forming circuit 18 and then stored in a memory of a CPU 7. In this regard, the stripe designates an area available for the evaluation provided by one time of continuous movement of the stage (sample carrier) and defines an area equivalent to a product of the scanning width by the deflector and the size of the sample in the other-axial direction, which contains a pattern subject to the evaluation on the inside and the interface thereof.

Before starting the evaluation of the sample, the scanning with the multi-beam 20-25 is applied to a L-shaped marker 19 (shown in the lower right section of FIG. 25) prepared always on the stage, and the secondary electrons emanating from each beam are detected by each detector, with which each small-sized two-dimensional image is produced. The resultant images are joined together based on the design values for respective positions of the multi-beam.

Assuming that such a pattern as represented by 8 (shown in the left-hand side of FIG. 25) was obtained as a result of the joining operation of the images, a joint site indicated by 30 is found between adjacent small-sized two-dimensional images. It can be determined from an amount of discontinuity in the joint site how much is the actual deviation in the x-direction from an original design value. If the actual deviation from the design value in the x-coordinate indicative of the position of each beam of the multi-beam can be successfully corrected, the deviation in 30 will be eliminated. For example, in the case indicated by 30, where the pattern produced by the lower beam is offset in the right-hand direction with respect to the upper pattern, the x-coordinate of the lower beam should be offset in the left-hand direction over the design value. The correction to the actual deviation can be performed while viewing the image.

Figure 26:
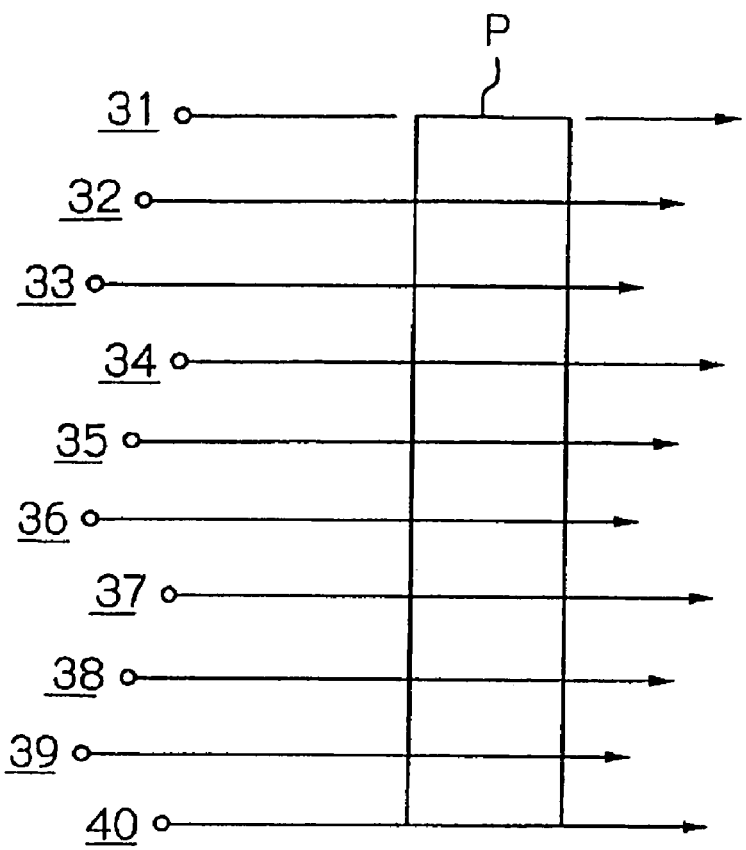
FIG. 26 is a diagram schematically showing an inter-beam adjusting method in a pattern evaluation method according to a first embodiment of the sixth invention.
Figure 26:
Figure 26:
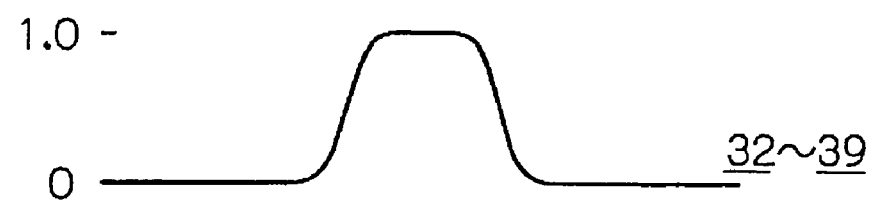
Figure 26:

A y-directional spacing between beams in the multi-beam will now be described. Assuming in this system that the pixel size is 100 nm, the beam spacing is 1 μm and the number of beams is 10, an exemplary signal waveform obtained by scanning the pattern, P, having the y-directional dimension of 9 μm is shown in the lower section of FIG. 26. The entire position of the multi-beam 31-40 is fine-tuned in the y-direction so that the amplitude of the waveform of the signal from the top beam 31 may be equivalent to 50% of the amplitude of the waveform from the intermediate beams 32-39, as shown in FIG. 26. That is, if the amplitude of the signal waveform from the top beam 31 is smaller than the 50% amplitude, this indicates that the beam 31 is scanning the region above (out of) the pattern, and so tuning should be performed to move the entire beam downward. Through this operation, the beam position is tuned such that the signal waveform from the top beam 31 defines the amplitude of 50% (i.e. such that a half of the top beam 31 covers the edge of the pattern), and then the waveform from the bottom beam 40 is examined. At this time, it may be found that if the amplitude of the waveform from the beam 40 exceeds 50% of the amplitude of the waveform from the intermediate beams 32-39 as indicated by the solid line, then the spacing between beams in the y-direction is too small, while on the contrary, if the amplitude of the waveform from the beam 40 is below 50% as indicated by the dotted line, the spacing is too large. That is, the spacing in the y-direction between the beams in a plurality of beams has been accurately measured. If the spacing is too narrow, the exciting voltage of the reduction lens should be increased so as to shorten the focal distance of this lens and make the reduction ratio approaching to zero, or if the spacing is too wide, the control should be provided to make the reduction ratio approaching to 1. Since this measuring method employs the measurement multiplied by 10 to evaluate the spacing between adjacent beams, the adjustment of high precision can be provided. In this way, the present invention has successfully achieved the accurate matching of the beam spacing 1 μm with the pixel size 100 nm multiplied by 10 (integer multiple).

In this way, the distance between the beams is adjusted, and in the condition that the adjusted beam distance has been stored, the small-sized two-dimensional images are obtained and joined in accordance with the distance between the beams that has been already stored as described above to thereby successfully form a large-sized two-dimensional image of high precision.

NINTH EXAMPLE

Figure 27:
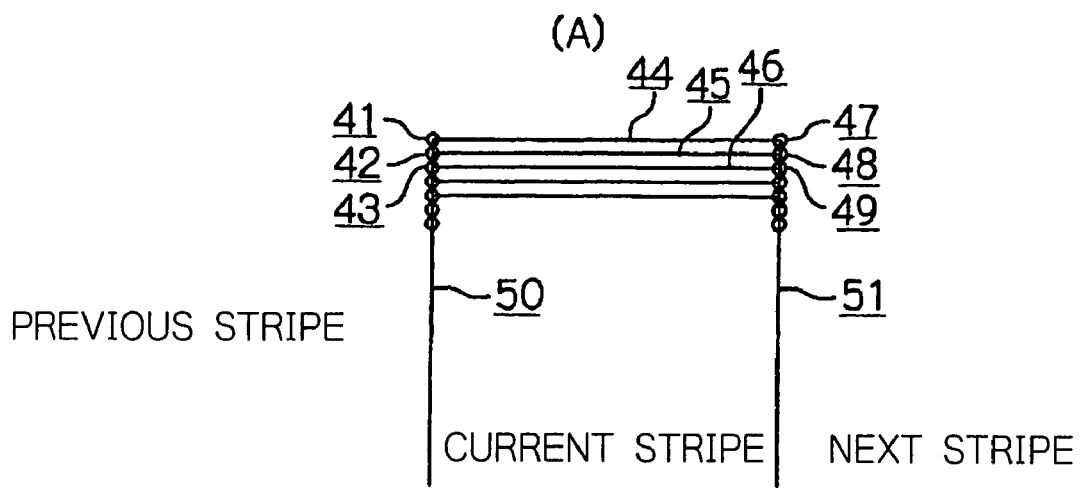
FIG. 27 is a diagram showing a feature in an interface between stripes in a pattern evaluation method according to a second embodiment of the sixth invention.
Figure 27:
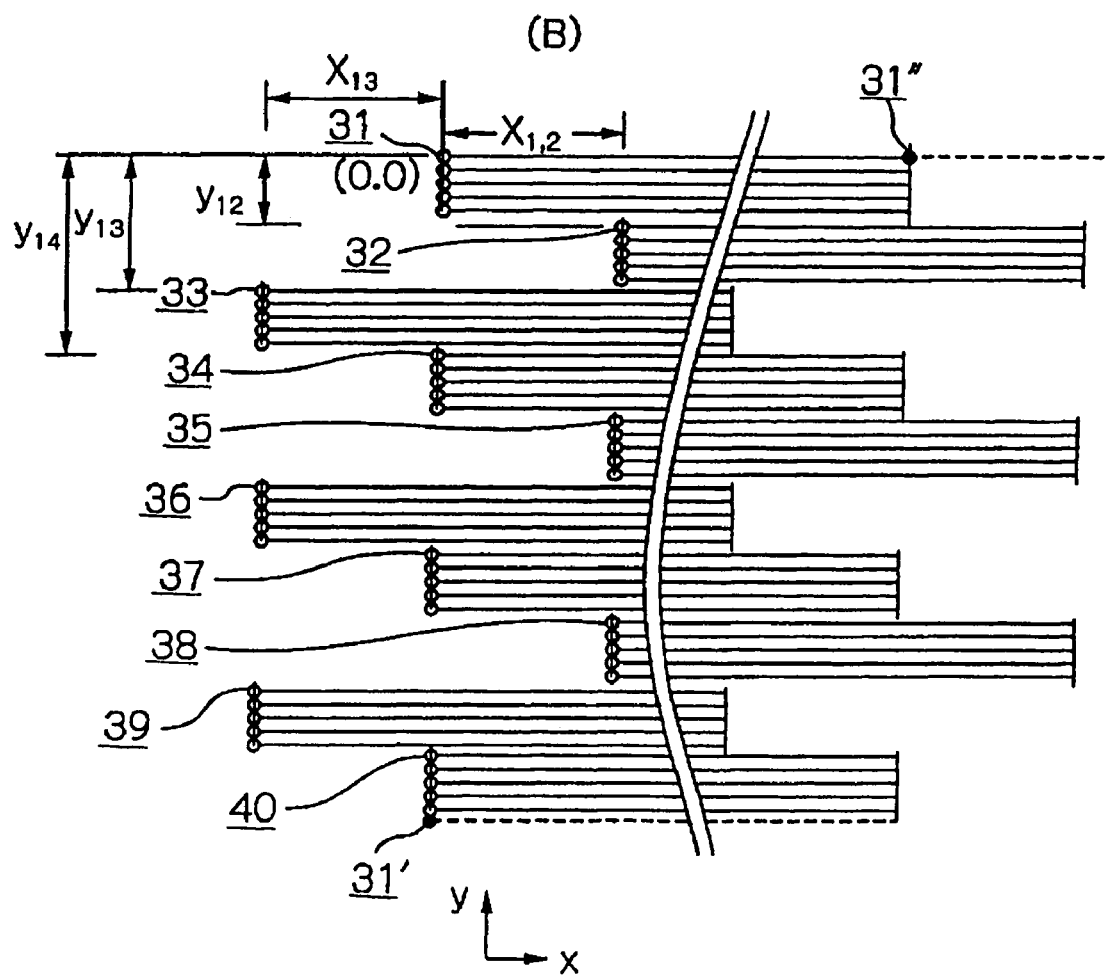

FIG. 27 shows a second example of the sixth invention.

If a single beam is used for the scanning as practiced in the prior art, from the fact that the x-coordinates of the starting points of the scanning, 41, 42, 43 and the x-coordinates of the end points of the scanning, 47, 48, 49, are respectively the same for the first scanning operation (starting point 41, scanning 44, end point 47) and the second and the third scanning operations as shown in FIG. 27(A), the interfaces 50, 51 may be straight lines parallel with the y-axis. However, in use of the multi-beam, where the respective beams have the different x-directional coordinates as indicated by 20-25 in FIG. 25, the x-coordinates of the starting points 31-40 of those beams are different. It is a matter of course from the same scanning time period that the x-coordinates of their end points of scanning are also all different. Taking this into account, it is suggested that the interface between the stripe in the left-hand side (white) and the stripe in the right-hand side (with scanning lines) should be in a concavo-convex configuration corresponding to the beam positions in the x-direction, as shown in FIG. 27(B). As a result, there would be no more chance of any overlapped scanning and thus any excessive irradiation, and any regions to be left not-evaluated due to insufficient scanning. To obtain the two-dimensional image in the scanning method of FIG. 27, assuming that the position of the image obtained by the signal from the beam of 31 is (0, 0), the images may be joined in such a manner that the position of the small-sized image obtained by the signal from the beam of 32 is shifted by $(x_{1,2}, y_{1,2})$ and the position of the small-sized image obtained by the signal from the beam of 33 is shifted by $(x_{1,3}, y_{1,3})$, generally by $(x_{1,i}, y_{1,i})$.

TENTH EXAMPLE

Figure 28:
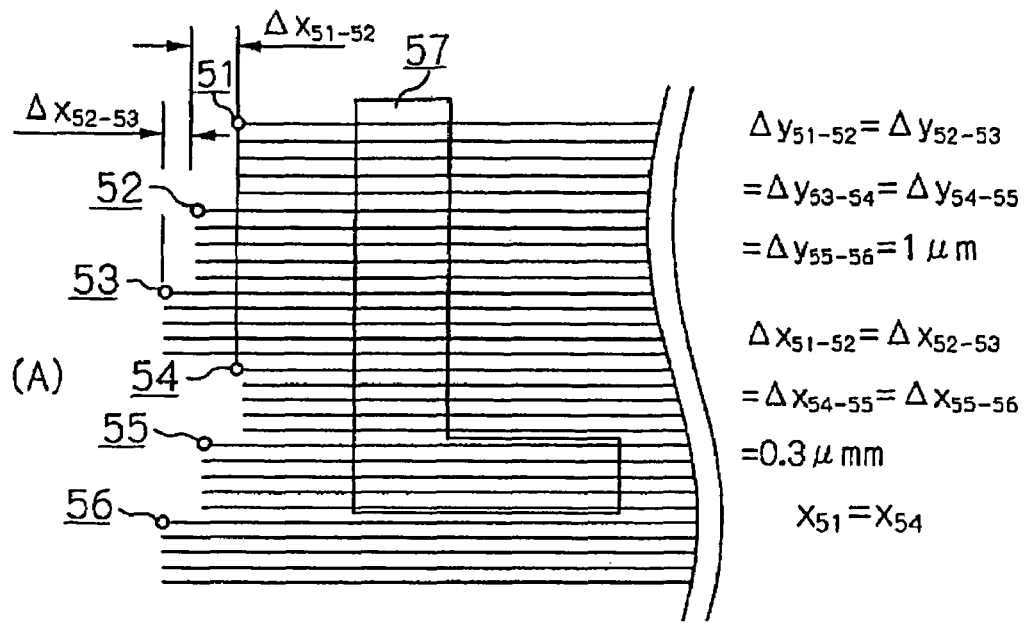
FIG. 28 is a diagram schematically illustrating an outline of joining operation of small-sized images in a pattern evaluation method according to a third embodiment of the sixth invention.
Figure 28:
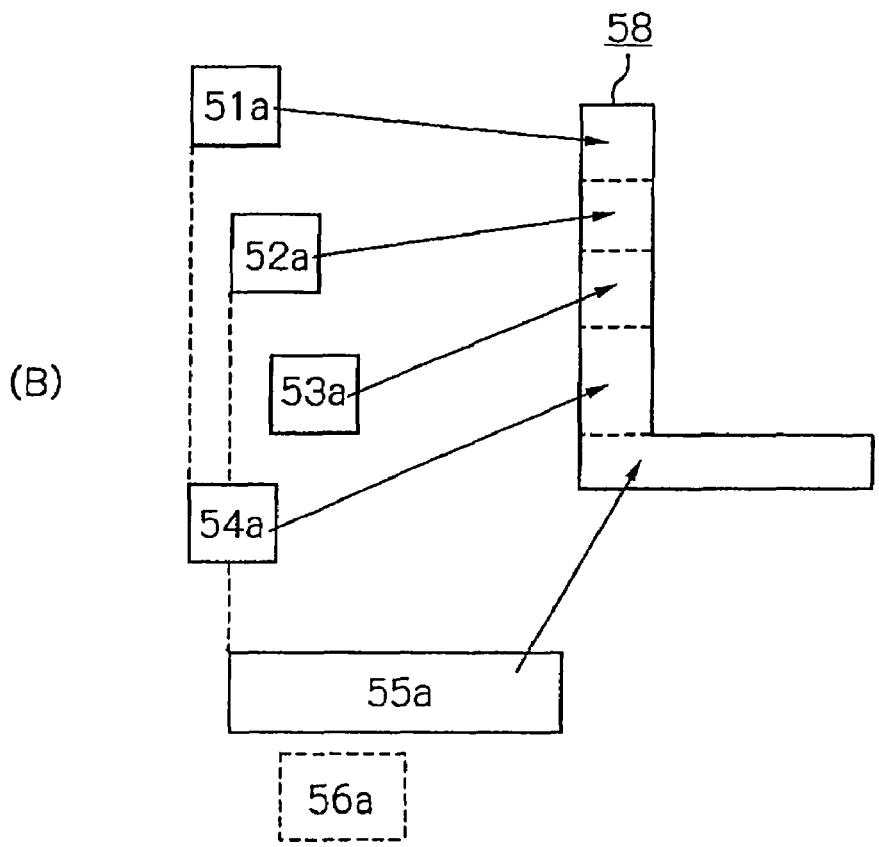

FIG. 28 shows a third example of the sixth invention.

This example illustrates a method for forming the large-sized two-dimensional image from small-sized two-dimensional images when the pattern 57 is to be evaluated by a plurality of beams 51 to 56.

The y-directional distance between any adjacent beams of the respective beams 51-56 is equal $(\Delta y_{51-52}=\Delta y_{52-53}=\Delta y_{53-54}=\Delta y_{54-55}=\Delta y_{55-56})$, for example, 1 μm, and the x-directional distance between the adjacent beams is also equal $(\Delta x_{51-52}=\Delta x_{52-53}=\Delta x_{54-55}=\Delta x_{55-56})$, for example, 0.3 μm, wherein the x-coordinates of the beams 51 and 54 are equal $(x_{51}=x_{54})$.

As shown in FIG. 28(A), each of the beams 51-56 is driven to make a scanning operation by the width of the stripe in the x-direction, while moving the pixel by the distance between the beams in the y-direction, and thereby the small-sized two-dimensional images 51a-56a can be obtained from the signals corresponding to respective beams. It is to be noted that the beam 56 resides out of the pattern and accordingly no corresponding image exists. The large-sized two-dimensional image can be obtained by making a correction to the distance between the beam positions for the small-sized two-dimensional images. Taking the above example of the beam positions by way of illustration, the two-dimensional image 58 having a continuous pattern can be obtained through the correction applied in such a way that, taking the image obtained from the beam 51 as a reference, the image 52*a* obtained from the beam 52 is shifted by 1 μm in the y-direction and by −0.3 μm in the x-direction, the image 53*a* obtained from the beam 53 is shifted by 2 μm in the y-direction and by −0.6 μm in the x-direction, the image 54*a* obtained from the beam 54 is shifted by 3 μm in the y-direction and by 0 μm in the x-direction, and the image 55*a* obtained from the beam 55 is shifted by 4 μm in the y-direction and by −0.3 μm in the x-direction. It is a matter of course that also in this example, preferably the spacing between respective beams 51-56 in the y-direction should be adjusted to be an integer multiple of the pixel size, as described previously.

Since the spacing between the beams of the multi-beam in the direction of the continuous movement of the sample table is defined by the integer multiple of the pixel size in this illustrated embodiment, a small-sized two-dimensional image obtained from the scanning with one beam and another small-sized two-dimensional image obtained from the scanning with an adjacent beam can be joined precisely in an accurate manner so as to create a large-sized two-dimensional image.

ELEVENTH EXAMPLE

Figure 29:
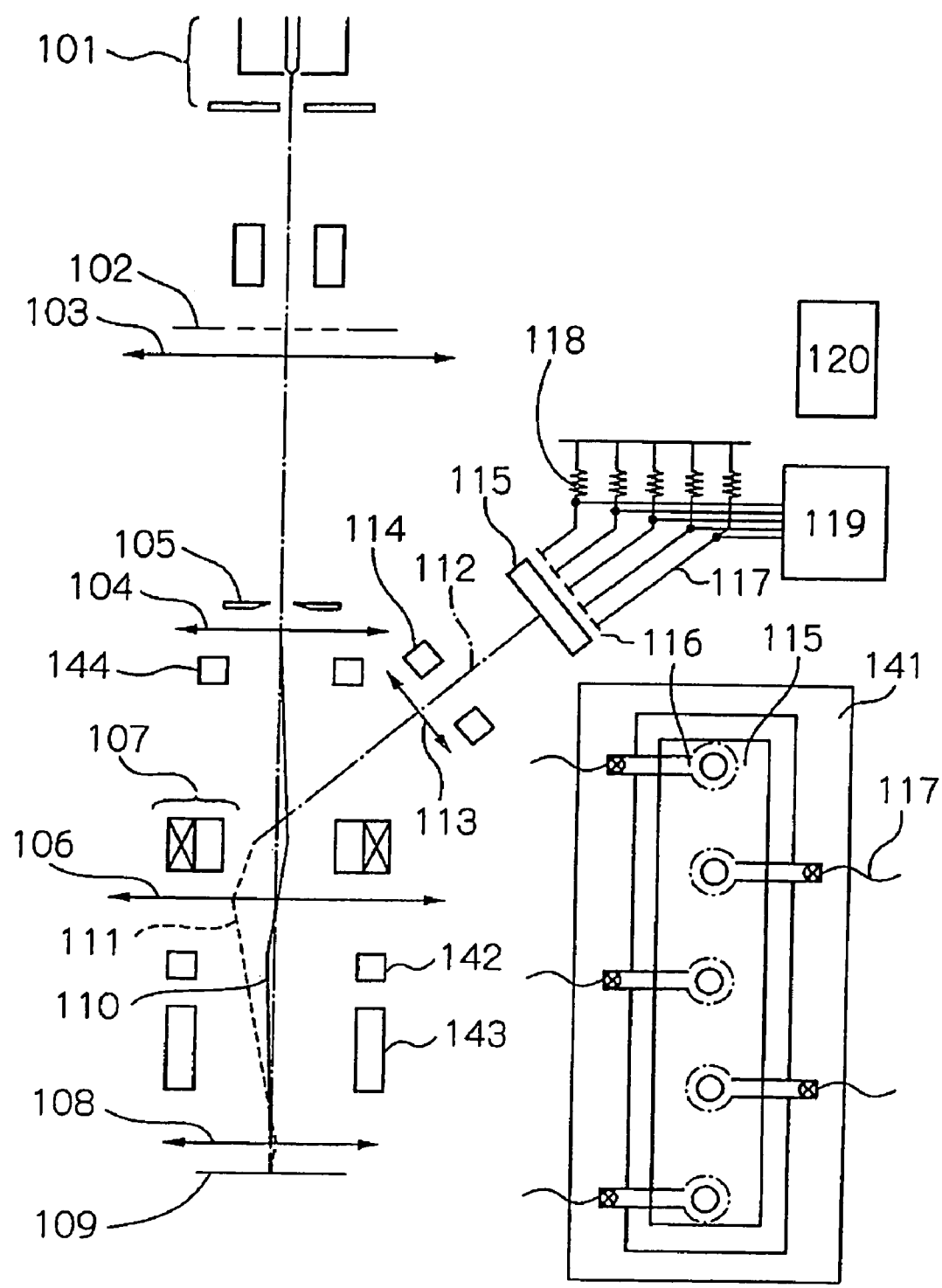
FIG. 29 is a diagram schematically showing an electron optical system used in a pattern evaluation method of a seventh invention.

FIG. 29 shows an electron optical system used in an embodiment of the seventh invention. An electron gun 101 has a single crystal $LaB_6$ cathode having a radius of curvature of 30 μm in the tip portion, from which an electron beam is emitted to irradiate over a multi-aperture 102 disposed in the vicinity of the optical axis to be formed into a multi-beam. The multi-beam from the multi-aperture is converged by a condenser lens 103 to form a crossover in an NA aperture 105, and then the multi-beam is converged by a reduction lens 104, and further reduced by a first objective lens 106 and a second objective lens 108 to be formed into an image on a sample surface 109 while being driven by electrostatic deflectors 142 and 143 to scan the sample surface. Since an E×B separator 107 is disposed at a location different from the point of image formation of the primary beam, the chromatic aberration from the deflection is induced in the primary beam. To avoid this, the present invention has set the deflection amount by the electromagnetic deflector of the E×B separator 107 as two times as large as the deflection amount by the electrostatic deflector thereof to thereby prevent the deflection chromatic aberration of the primary beam from being induced. In this condition, to allow the beam to pass through the center of the first objective lens 106, the pre-deflection is carried out by a deflector 144. Further, assuming the trajectory of the principal ray of the primary electron beam follows 110, it may pass through the center of the second objective lens 108 but enter a location a bit away from the optical axis on the sample 109. The secondary electrons emitting from this site follow the trajectory indicted by the dotted line 111 and are further deflected by the E×B separator 107 into a secondary optical system 112. The spacing between the beams is extended by a magnifying lens 113, and each beam of the multi-beam is multiplied by a MCP 115, absorbed by a multi-anode 116 and converted into a voltage signal by a resistor 118, which is in turn multiplied by 119 and A/D-converted into a two-dimensional signal, which is stored in a memory 120. It is to be noted that reference numeral 114 designates a deflector, 117 a lead wire, 141 a detector fixing plate in FIG. 29. In addition, FIG. 29 shows a plan view of the detector in the lower right section thereof.

In this connection, in order to form a magnified image on an incident plane of the MCP 115 by the magnifying lens 113, it is necessary for the secondary electrons emitting from the sample 109 to form the magnified image at a position proximal to the principal plane of the magnifying lens 113 with the aide of the lenses 108 and 106, and further it is necessary to form the magnified image of the secondary electrons in the position proximal to the principal plane of the magnifying lens 113 as described above specifically under the lens condition for focusing the primary beam on the sample 109 by the lenses 106, 108. This condition is referred to as "the concurrent focusing condition of the primary and the secondary beams".

Figure 30:
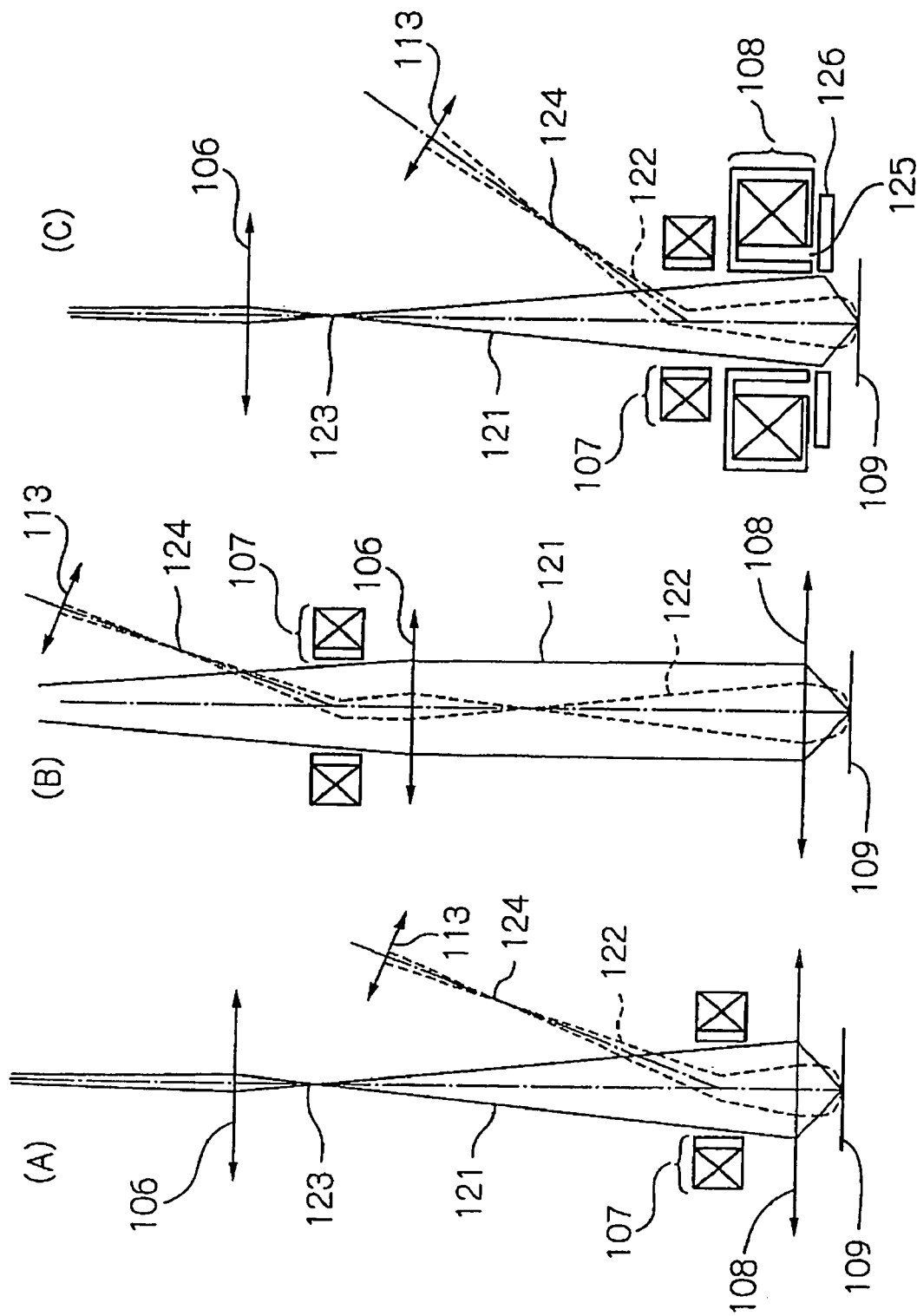
FIG. 30 illustrates three different cases for determining a concurrent focal condition for a primary and a secondary beam in the seventh invention.

The concurrent focusing condition of the primary and the secondary beams will be determined by using FIG. 30.

FIG. 30 illustrates three different types of optical system defining the common passage of the primary and the secondary beams, wherein FIG. 30(A) shows a system including one-stage of objective lens, FIG. 30(B) shows the same system as FIG. 29 and FIG. 30(C) shows the system in which the objective lens includes an electromagnetic lens. FIG. 30(B) corresponds to the system of FIG. 29, and FIGS. 30(A) and (C) show variations of the system of FIG. 25.

FIG. 30(A) illustrates a case allowing for the common passage of the primary and the secondary beams only through one-stage of lens. Assuming that the typical primary beam used in the prior art is of 0.3 kV or higher, the secondary electrons accomplish its focal condition at a point immediately above the objective lens 108 and before the E×B separator 107, implying that the object point distance of the magnifying lens 113 is too long, and so if the lens 113 is used as a magnifying lens, the secondary optical system becomes too long. To place an image point of the secondary beam near to 124 under the lens condition satisfying the focal condition of the primary beam, it has been found from a simple simulation that the landing energy of the primary beam should be controlled to 300 V or lower. It is to be noted that in the drawing, reference numeral 121 is a diagram of the primary beam image formation, 122 is a diagram of the secondary beam image formation and 123 is a first reduction image of the multi-beam.

If the primary and the secondary beams have a common passage through the lenses 106 and 108 as shown in FIG. 30(B), the requirement of the landing energy to meet the concurrent focusing condition of the primary and the secondary beams can be relaxed, so that the landing energy of 600 V or lower for the primary electron beam has still allowed the image point of the secondary electrons to be focused at the location 124 before the magnifying lens 113. If this landing energy is set at 600 V or higher, the locus 121 of the primary beam exhibits divergence toward the top in the drawing, resulting in a large diameter at the position of the lens 106, which leads to an increase in aberration of the primary beam.

The description will now be directed to FIG. 30(C). In the illustrated embodiment, the objective lens 108 has employed a synthetic lens composed of an electromagnetic lens and an electrostatic lens. The portion containing no ferromagnetic material in the magnetic circuit, or the lens gap 125, is defined in the sample side, and the z position producing a maximum on-axis magnetic field of the lens is defined in the sample side with respect to the gap. At the z position associated with the maximum on-axis magnetic field, the beam is most intensively subject to the focusing effect. An electrode 126 for applying a positive high voltage is disposed in the vicinity of said z position so as to reduce the (energy range/beam energy at the lens position) ratio to thereby reduce the axial chromatic aberration. That is, said ratio has been reduced by increasing the denominator. Since the lens effect of the electromagnetic lens is in inverse proportion to the square root of the beam energy and the lens effect of the electrostatic lens is in inverse proportion to the beam energy, therefore in this case, essentially the landing voltage of the primary beam can be made considerably high as compared to the 300 V of the case of (A) including only one-step of electrostatic lens. It has been found as a result of the simulation that the landing voltage of 500 V or lower can provide a practical position acceptable for both of the object point 123 of the primary beam and the image point 124 of the secondary beam.

TWELFTH EXAMPLE

Figure 31:
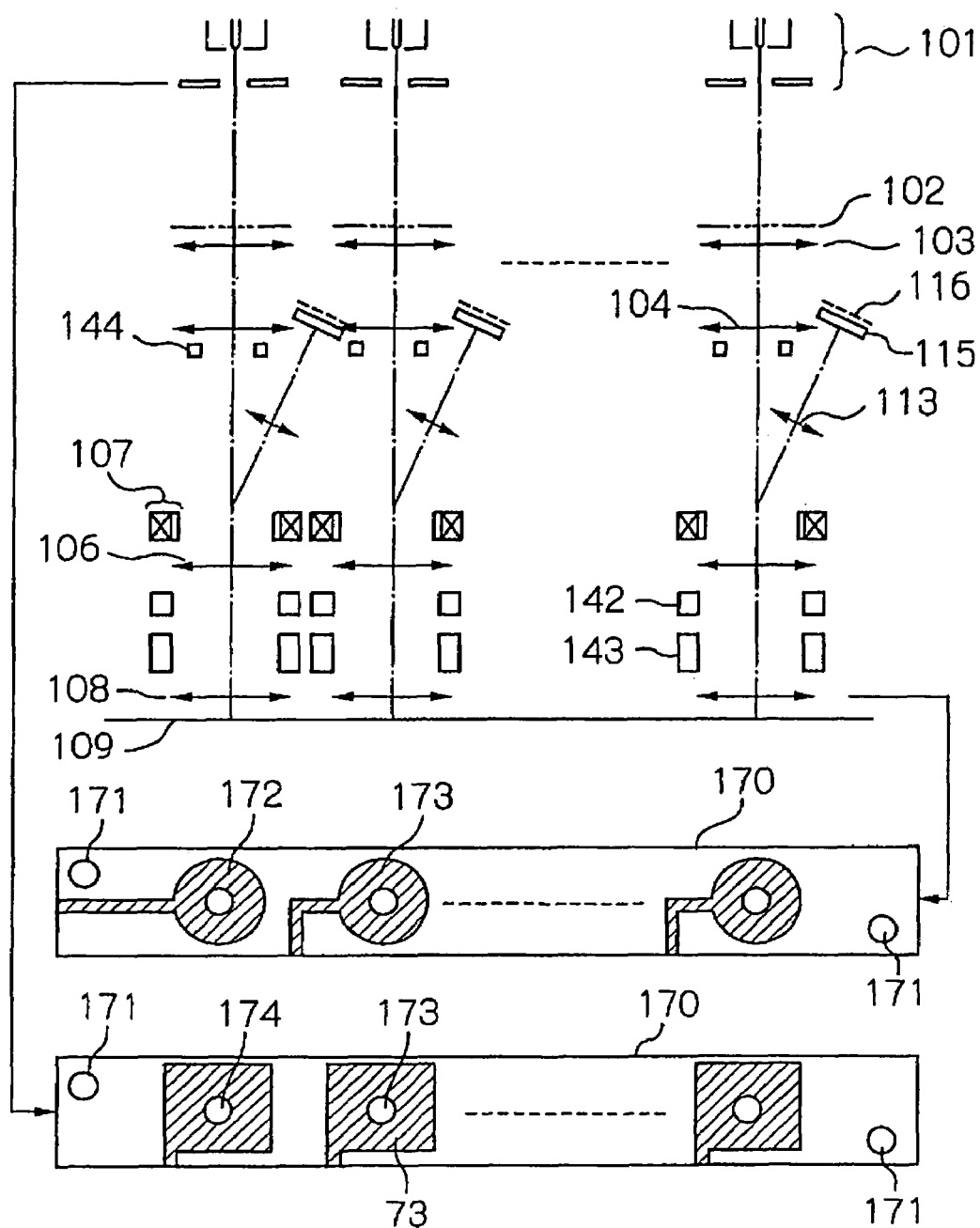
FIG. 31 is a diagram showing a second embodiment of the seventh invention, schematically illustrating an apparatus including a plurality of optical systems, each with a multi-beam formed around a single optical axis.
Figure 32:
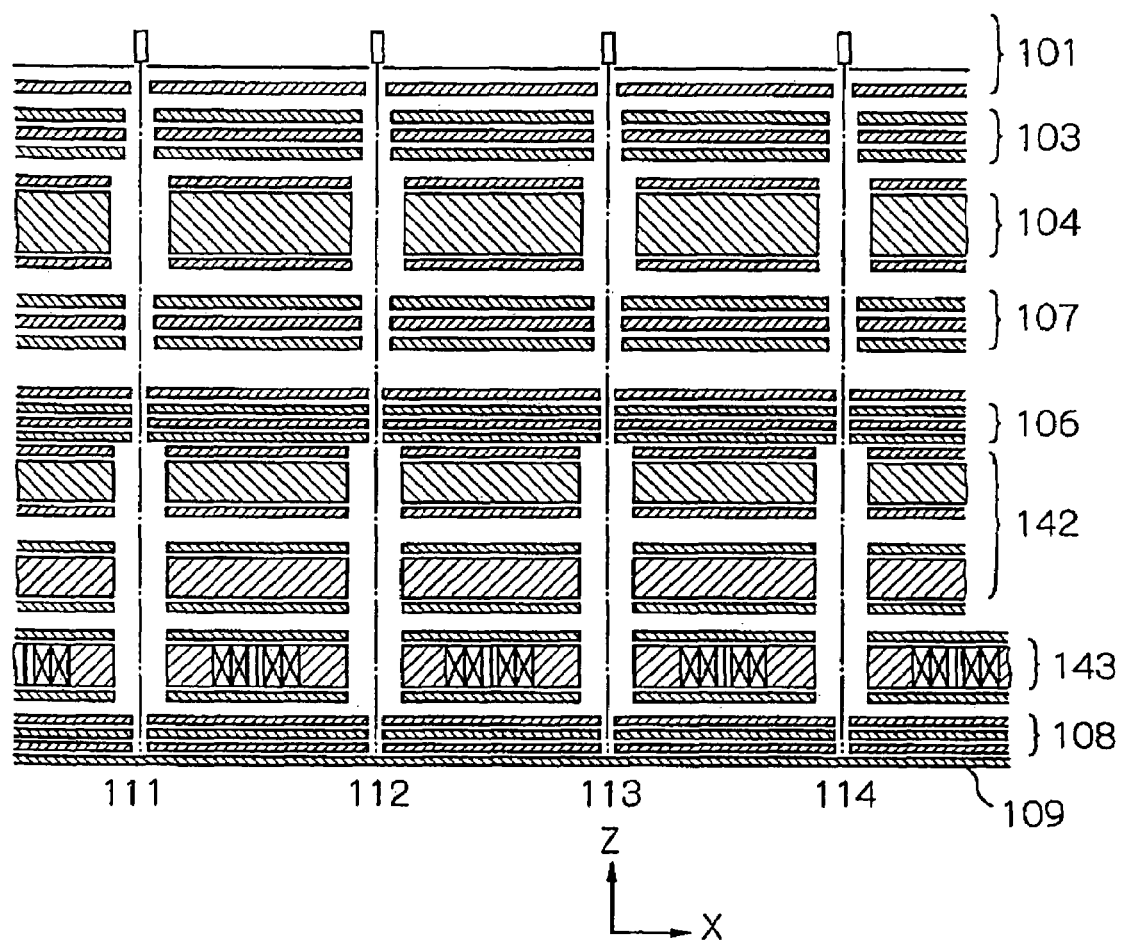
FIG. 32 is a sectional view showing the apparatus of the second embodiment of the seventh invention, illustrating one case, by way of example, where a plurality of optical elements is made of ceramic plates stacked in the z-axial direction.

FIG. 31 shows an electron optical system according to a second embodiment of the seventh invention. FIG. 31 includes a plurality of optical systems shown in FIG. 29 arranged along a straight line. In this embodiment, a plurality of apertures 172, 174 corresponding to respective optical axes is formed in a ceramic substrate 170 with metal coating 173 applied in the periphery of the apertures and thus configured plates are fabricated by a desired number and further assembled by using knock pins 171 to provide a primary optical system defined from an electron gun 101 to the lower pole of the objective lens 108. FIG. 32 shows reference numerals corresponding to the above-described optical elements in its right-hand side. In the drawing, reference numeral 101 designates an electron gun, 102 a multi-aperture plate, 103 a condenser lens, 104 a condenser lens, 106 a reduction lens, 107 an E×B separator, 108 an objective lens, 109 a sample, 113 a magnifying lens of a secondary optical system, 115 an MCP, 116 a multi-anode, and each of 142, 143 and 144 an electrostatic deflector. Further, as to the secondary optical system, the optical axes extend obliquely in opposite directions for every adjacent optical axis of the primary optical system disposed along the straight line, and so the spacing between adjacent optical axes in the secondary optical system would be expanded by a multiple of two, meaning that there should be no problem, if the secondary optical system is fabricated individually for each one of the optical axes. That is, in FIG. 32, since the secondary optical system is arranged such that the optical axes 111 and 113 are directed to the front surface of the sheet and the optical axes 112 and 114 are directed to the back surface of the sheet, meaning that the spacing between adjacent axes of the secondary optical system refers to the spacing between 111 and 113 or the spacing between 112 and 114, which is equivalent to the double of the spacing between 111 and 112. Therefore, the secondary optical system may be constructed independently for each optical axis as practiced in the prior art.

According to the illustrated embodiment, since the ratio of (the landing energy of the primary electron beam/the energy of secondary electrons) is relatively small, such as (600 eV/2 eV)=300 or lower (the case A of FIG. 30), (300 eV/2 eV)=150 or lower (the case B), and (500 eV/2 eV)=250 or lower (the case C), as compared to the conventional (1000 eV/2 eV)=500, and accordingly the concurrent focusing condition of the primary and the secondary beams could be easily satisfied, therefore it becomes possible to form a multi-beam in the vicinity of the single optical axis in the primary optical system and detect the secondary electrons independently without any cross talk among them.

THIRTEENTH EXAMPLE

Figure 33:
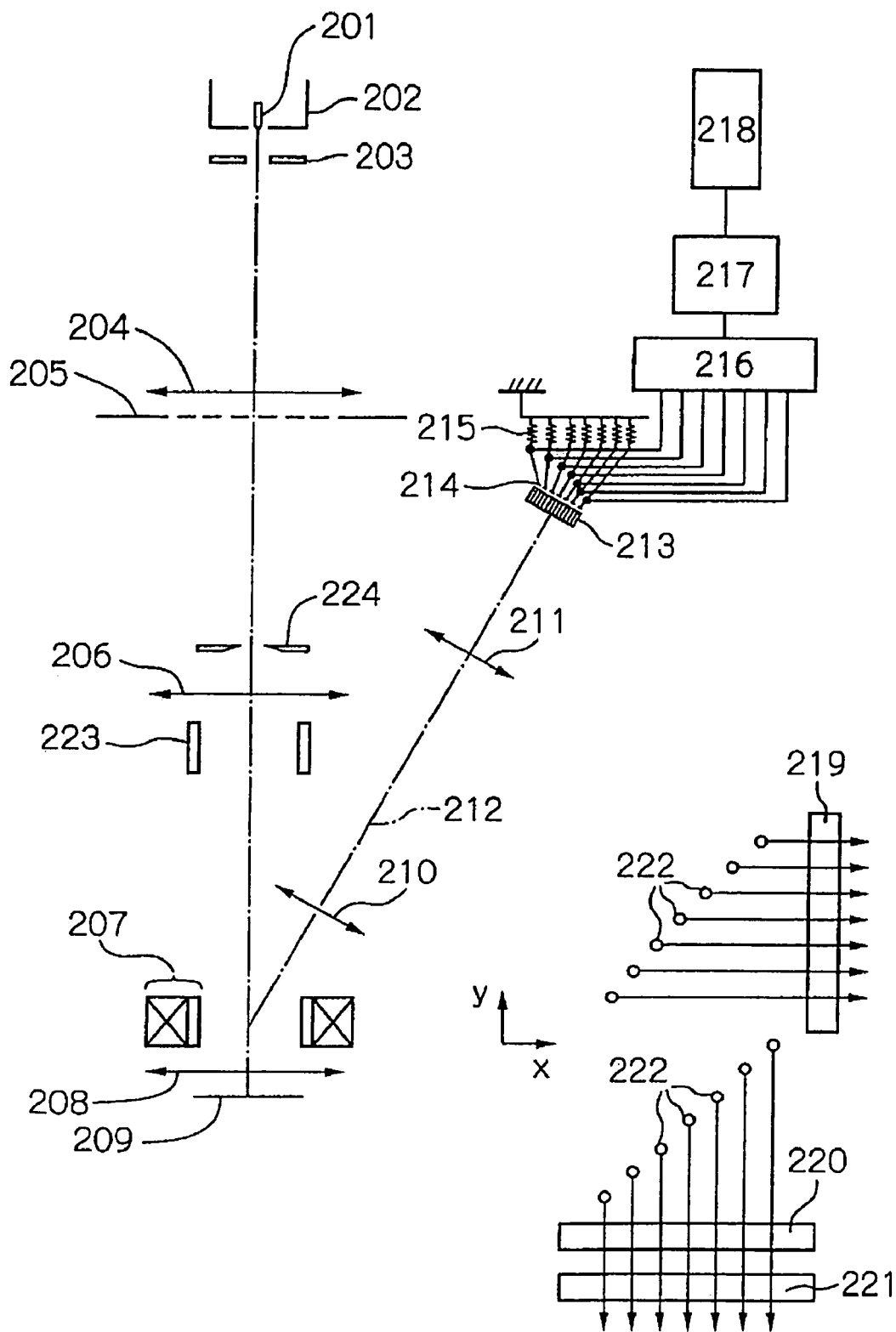
FIG. 33 is a diagram schematically showing an electron optical system used in a pattern evaluation method of an eighth invention.

FIG. 33 shows an overview of an electron optical system used in an embodiment of the eighth invention. The electron gun comprises a $LaB_6$ single crystal cathode 201, a Wehnelt 202 and an anode 203, in which the cathode 201 is actuated under the space charge limited condition to thereby reduce the shot noise effectively to one-quarter of or lower than that obtained by using the Schottky cathode, and a satisfactory S/N ratio can be accomplished with the number of electrons on the order of 250 per pixel. Accordingly, the evaluation of such a resist as ArF resist whose resist feature is more apt to change by the irradiation of the electron beam can be provided without causing any deformation over the resist.

An electron beam emitted from the electron gun is converged by a condenser lens 204 and irradiated over a multi-aperture 205 to be formed into a crossover in an NA aperture 224. The beam that has been formed into a plurality of beams through the multi-aperture 205 is reduced by the reduction lens 206 and the objective lens 208 so as to form a narrowly converged multi-beam on a sample 209. Those beams of the multi-beam are driven by an electrostatic deflector 223 and an electrostatic deflector of an EB separator 207 to scan the sample 209. Since the sample 209 is applied with a voltage of −4 kV, for example, the secondary electrons emitted from the scanning points on the sample are accelerated toward the objective lens 208, converged into a narrow bundle of beams with the spacing between beams extended, and ultimately formed into a secondary electron image in the vicinity of the E×B separator 207. A secondary beam is deflected by the E×B separator 207 at an angle of about 200 relative to the primary beam and adjusted in its magnification by magnifying lenses 210 and 211 of a secondary optical system to be focused into an image on an incident plane of an MCP 213 with an arrangement corresponding to a pitch of a multi-anode 214 disposed behind the MCP 213. The electrons from each beam are multiplied in the MCP 213, and each beam is independently absorbed in the multi-anode 214 and converted into a voltage signal by a resistor 215 and further into a digital signal by a group of preamplifiers and A/D converters 216, to which a variety of processing is applied in a two-dimensional image forming circuit 217 and the processed image data is stored in a memory 218.

The multi-beam is aligned along a line extending to the direction of about 45° as indicated by 222 in the lower right section of the drawing. A signal waveform in the scanning of a y-line 219 in the x-direction is shown in (A) of FIG. 34, and a signal waveform in the scanning of two x-line patterns 220, 221 in the y-direction is shown in (B) of FIG. 34. In addition, the method for measuring edge roughness is illustrated in (C) with respect to the y-line.

During the CD measurement shown in FIG. 34(A), the processing is applied to the signal waveform directly without any pre-processing prior to the formation of the two-dimensional image. That is, a threshold value 231 is applied to each of the seven signal waveforms 232, and a time interval 233 between the times when the waveform traverses the threshold value is determined, which in turn is converted to a dimension by using a scanning rate and finally a CD value may be determined for each beams of the multi-beam and averaged among them, or alternatively the signal waveform 232 may be applied with the positional adjustment by a time period corresponding to a difference in spacing between the beams in the x-direction and the resultant signal waveforms may be added and averaged to determine the time interval 233 with the improved S/N ratio.

Instead of the threshold method, tangential lines 234 and 235 may be applied to the leading edge and the trailing edge of the signal waveform, wherein intersections of the tangential lines with a base line 236 of the signal are determined, and then a time difference 237 therebetween is determined and converted to a dimension. Which of the methods, the threshold method or the method using the tangential line is to be employed may be determined depending on the material of the pattern, the vertical structure and so on.

Figure 34:
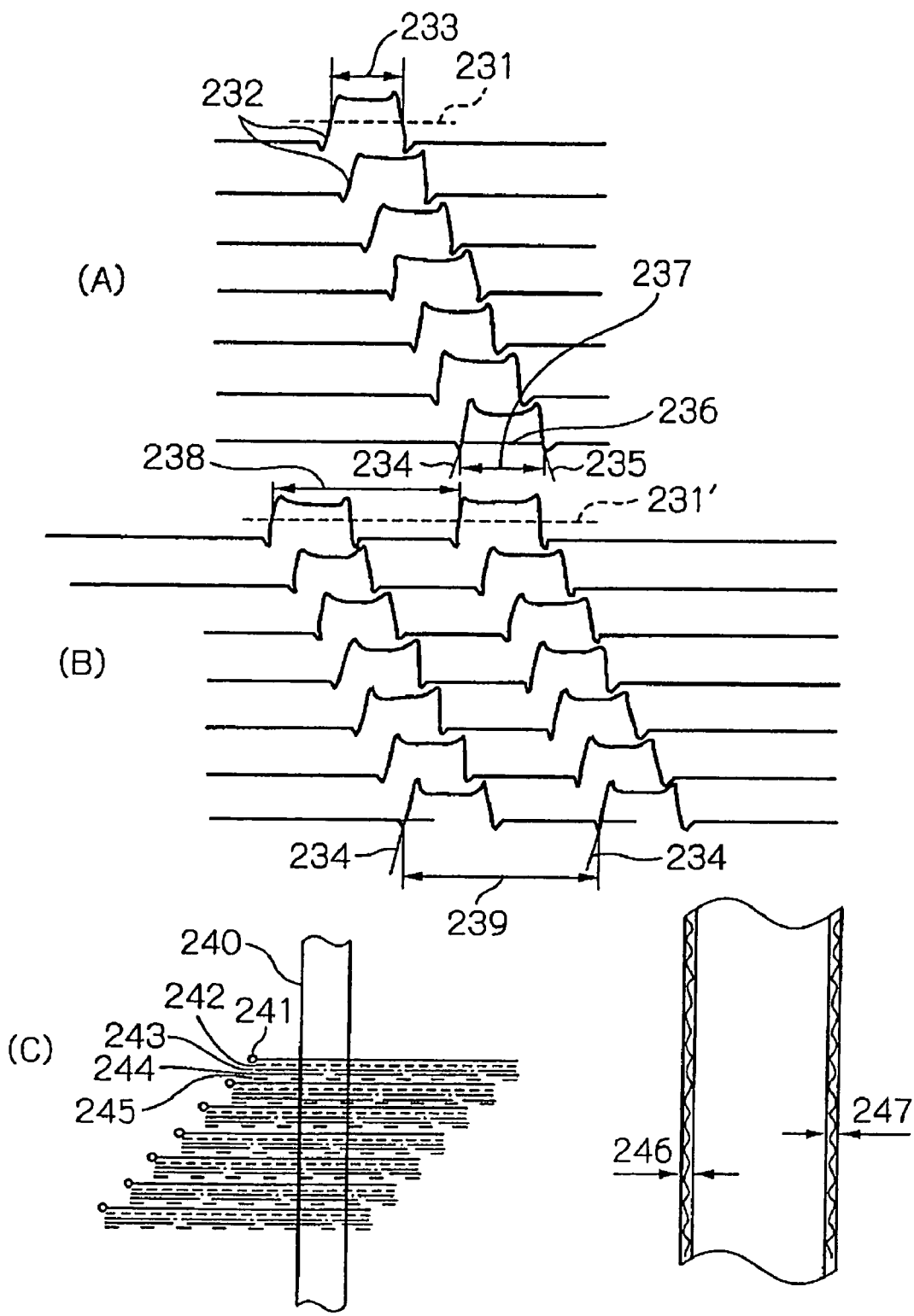
FIG. 34 is a diagram illustrating a pattern evaluation method of the eighth invention, wherein (A) shows an outline of a CD measurement, (B) shows an outline of aligning accuracy measurement and (C) shows an outline of edge roughness measurement, respectively.

An aligning precision measuring method shown in FIG. 34(B) will now be described. For the measurement of the aligning precision in the y-direction, the multi-beam 222 is moved to the vicinity of a pattern 221 formed in the following layer located in the vicinity of the pattern 220 formed in the previous layer, and then the scanning is carried out with the multi-beam all together in the y-direction concurrently. The signal waveform from the detector associated with each beam during this operation is represented in (B) of FIG. 34. The sharper edge in the leading edge and the trailing edge of the waveform is selected, and a time interval or a distance 238 between intersections of the selected edge with the threshold value 231 should be determined. In this case, since, differently from the case of (A) where both of the leading edge and the trailing edge of the signal waveforms are used, either one of the leading edge or the trailing edge of the signal waveform may be used in determining the threshold value, the value representing the most sharp leading edge or trailing edge of the signal waveform, typically the value equivalent to 50% of the amplitude may be selected. It is a matter of course that the aligning precision may be calculated by approximating the leading edges or the trailing edges by the tangential lines 234, wherein the time 239 is determined from the intersections of the tangential lines with the base line, and thus determined time is converted to the distance, which in turn is compared to the design value to thus calculate the aligning precision.

An example of the eighth invention will now be described in connection with the method for measuring the edge roughness. The multi-beam is moved to the vicinity of the y-pattern 240, and then driven to perform the scanning operation in the x-direction. If the interval between respective beams in the y-direction encompasses a few pixels, then the multi-beam performs the scanning operation while each beam is shifted by one pixel in the y-direction, as shown in 241-245, and this operation is repeated until the scanning has been finished entirely for the every inter-beam distance to thereby obtain the two-dimensional image. As it is, the edge roughness can be measured from the measurement of a P-P value or an effective value of the concavo-convex area based on the obtained image as designated by 246, 247. In this regard, it is necessary to slow down the pixel frequency of the signal waveform in each scanning operation so that a good S/N ratio can be obtained.

According to the eighth invention, the evaluation of the pattern requires relatively shorter time corresponding to a number of beams, and thus the time required for the measurement can be shortened.

FOURTEENTH EXAMPLE

Figure 35:
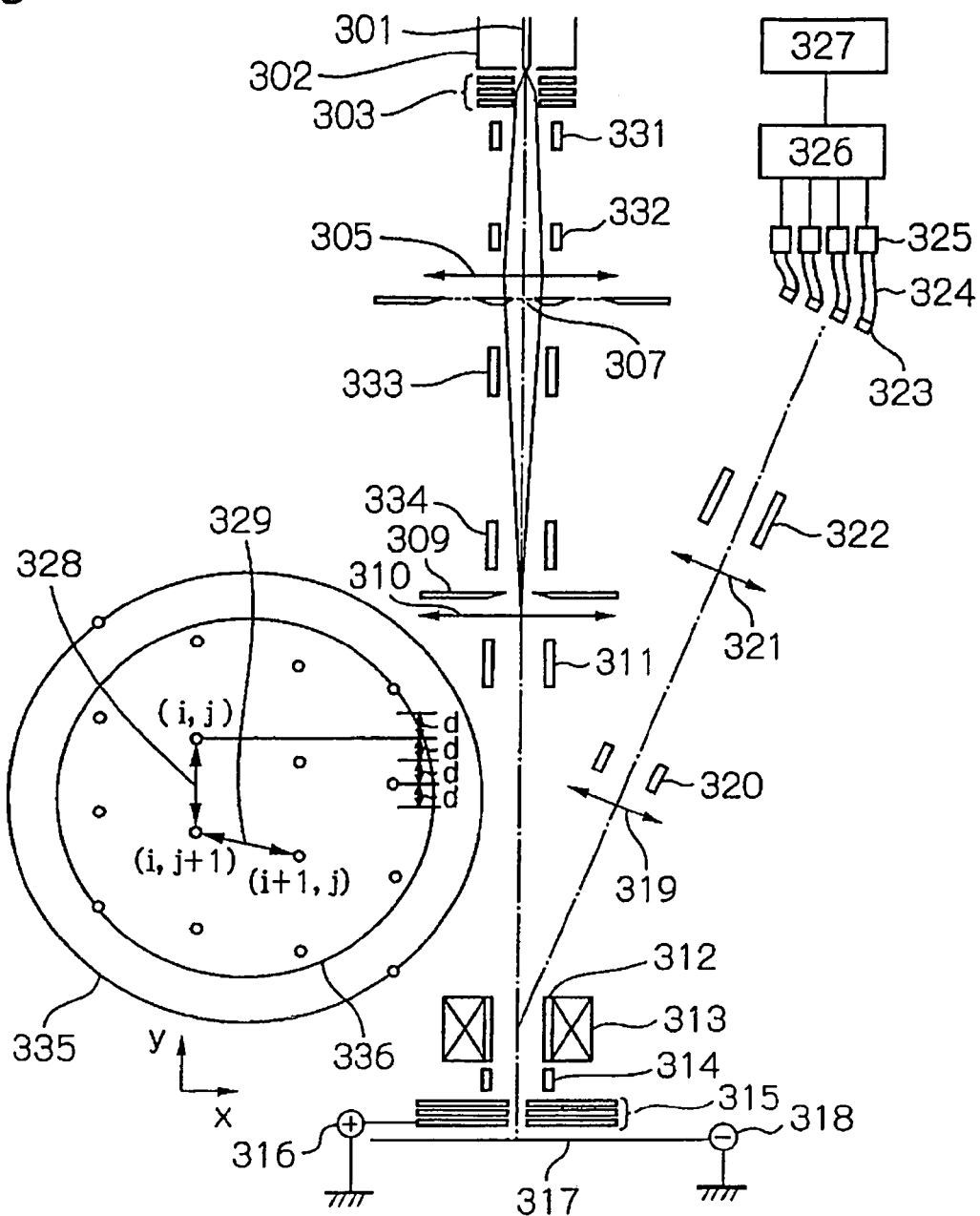
FIG. 35 is a diagram schematically showing an electron optical system used in a pattern evaluation method according to a ninth invention.

FIG. 35 shows a schematic diagram of an electron optical system used in a pattern evaluation method according to an embodiment of the ninth invention.

The electron gun comprises an $LaB_6$ cathode 301, a Wehnelt electrode 302 and a triple-electrode anode 303, in which a positive voltage is applied to a central electrode of the triple-electrode anode 303 to thereby define a convex lens of a small spherical aberration. An appropriate control of the focusing effect of this convex lens can adjust the irradiation area on the multi-aperture 307. Alternatively, an NA value (focusing half angle) of a primary beam on a sample 317 can be controlled by modifying a size of a crossover formed in an NA aperture 309 by changing a focal distance of the lens. In either case, the primary beam emitted from the electron gun 301, 302, 303 is axially aligned by axial aligning deflectors 331 and 332 with a condenser lens 305 and the multi-aperture 307. In the condenser lens 305, an exciting voltage is determined so as to focus the crossover on the NA aperture 309. The electron beam passes through the multi-aperture 307 to be formed into a multi-beam, which is axially aligned by a two-step of axial aligning deflectors 333 and 334 with both of the NA aperture 309 and a reduction lens 310, reduced by a reduction lens 310 and an objective lens 315 to be focused on the surface of the sample 317, and at the same time, driven by deflectors 311 and 314 to perform a raster scanning across the sample 317. During the scanning operation across the sample with the multi-beam, the dynamic focusing is applied to the multi-beam, that is, the converging power of the lens is changed in synchronism with the scanning operation to compensate for the aberration due to the curvature of field, so that the multi-beam may be always focused on the sample surface. Secondary electrons emitting from scanning points of the multi-beam on the sample are accelerated and converged by an accelerating electric field generated by the objective lens 315 and the sample 317 for the secondary electrons in the vicinity of the sample, and after passing through the objective lens 315, the secondary electrons are deflected by an E×B separator 313 so as to be directed to a secondary optical system, where a spacing between the beams of secondary electrons is extended by a two-stage of magnifying lens 319, 321, and also a zooming operation is applied thereto so that the spacing between the images of secondary electrons may be equal to the interval between secondary electron detectors 323. In this connection, the simulation has shown that the higher is the intensity of the electric field in the vicinity of the surface of the sample 317, the smaller is the out-of-focusing of the secondary electron image on the detector 323. However, if the electric field intensity is too high, resultantly the discharge is induced between the lens 315 and the sample 317, possibly leading to a destroyed sample. Accordingly, the voltage to be applied to a lower electrode of the lens 315 is determined so that the critically intensified electric field that would not cause any discharge between the lens 315 and the sample 317 can be produced over the wafer surface. The electric field intensity that triggers the discharge in the sample is not constant but depends on the condition in the surface of the sample, wherein, for example, if such a projection like a via is present in a wafer surface, a locally intensified electric field could be formed even with an average electric field intensity as low as 1.6 kV/mm resulting in the discharge at that point. As for a flat wafer with a film of $SiO_2$ deposited on the surface thereof, the electric field intensity that could induce discharging is as high as 6 kV/mm.

Accordingly, the voltage applied to the lower electrode should be once made variable within a range allowing the average electric field intensity formed between the sample 317 and the lower electrode to fall in a range of 1.5 kV/mm to 5.5 kV/mm, wherein the voltage applied to the lower electrode may be appropriately selected to be 1.5 kV/mm that is a bit lower than 1.6 kV/mm for the evaluation of the sample containing a via or 5.5 kV/mm that is a bit lower than 6 kV/mm for the evaluation of the sample deposited with the $SiO_2$ film. This can eliminate the possibility of discharging to be induced and provides a feature of the secondary optical system that the out-of-focusing of the secondary electron image can be minimized.

The arrangement of the primary electron beams involves a requirement that the distance between adjacent beams of the primary electron beam should be made larger than a resolution of the secondary optical system and also that the beam intervals, d, between any adjacent beams projected on the y-axis are all equal. FIG. 35 shows in its left-hand side by ○ marks an example of the arrangement of the beams that can meet above-discussed two requirements and in which a certain number of beams can be arranged in as small circle as possible. In the illustrated example, the total of 16 beams in an array of 4-row×4-column are successfully positioned within the circle 335. If fourteen beams, they are all positioned within the circle 336. Thus, in order to accommodate a specified number of beams in as small circle as possible, assuming that each beam is designated by i-th in the x-direction and j-th in the y-direction, it is required that the distance 328 between the adjacent beams (i, j)th and (i, j+1)th should be approximately equal to the distance 329 between the adjacent beams (i, j+1)th and (i+1, j)th.

It is to be noted that in FIG. 35, reference numeral 316 designates a positive high-voltage power supply, 318 a negative voltage power supply, 320, 322 an axial aligning deflector, 323 a scintillator, 324 a light guide, 325 a PMT, 326 an A/D converter and 327 an image forming device.

FIFTEENTH EXAMPLE

Figure 36:
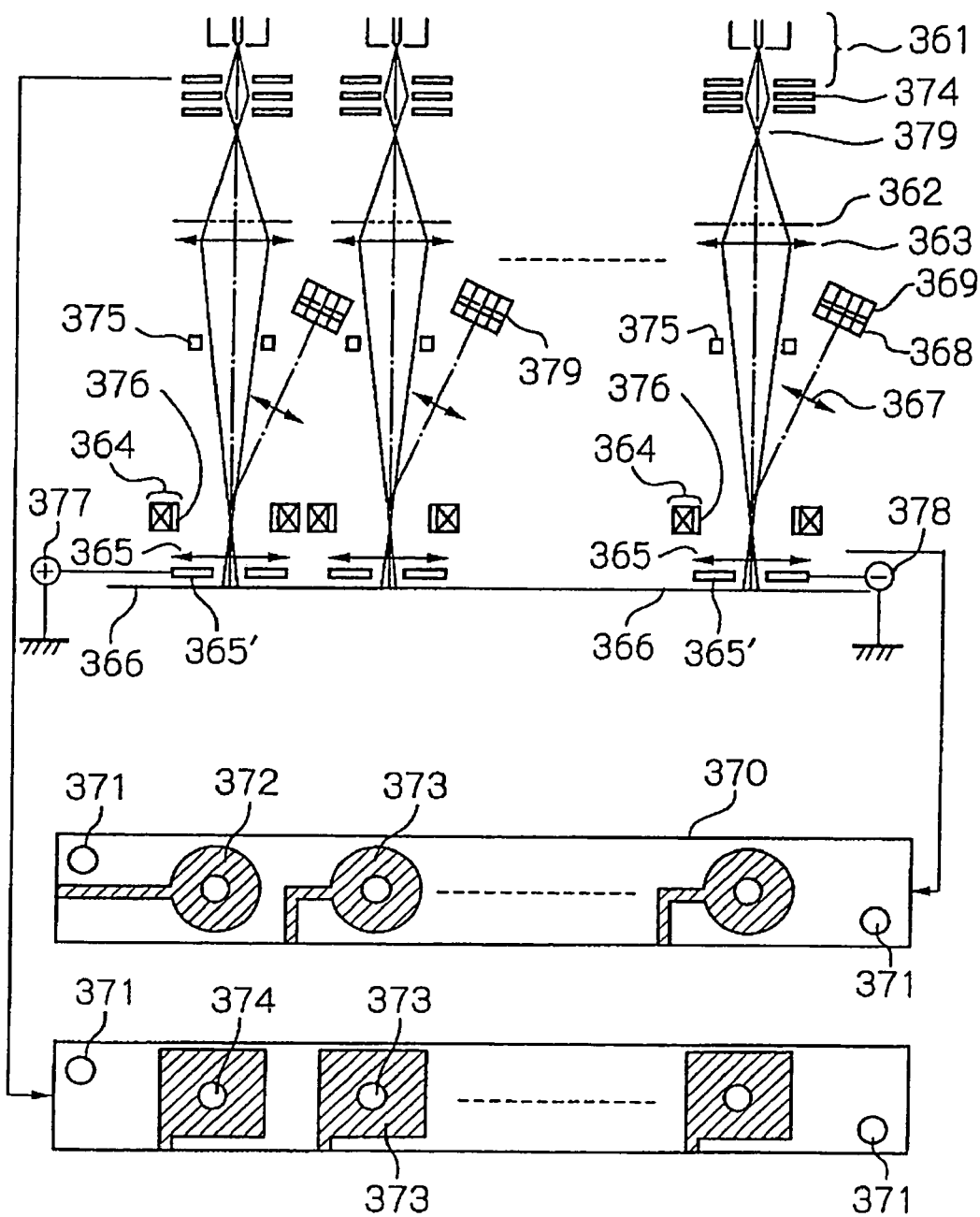
FIG. 36 is a diagram schematically showing a second electronic optical system used in the ninth invention.

FIG. 36 shows an electron optical system used in a pattern evaluation method according to a second example of the ninth invention. An electron beam emitted from an electron gun 361 is subject to the focusing effect of a triple-electrode anode 374 to once form a crossover 379, and the beams divergent therefrom irradiate a multi-aperture 362 to be formed into a multibeam. Those beams are reduced by a condenser lens 363 and an objective lens 365 to be focused on a sample 366. The multi-beam is driven by an electrostatic deflector 375 and an electrostatic deflector 376 of an E×B separator 364 to perform the scanning operation across the sample 366, and secondary electrons emitting from the scanning points are narrowly converged by applying a positive high voltage 377 to an electrode 365' disposed at the lowest position in the objective lens 365, and after passing through the objective lens 365, deflected by the E×B separator 364 toward a secondary optical system, where an interval between groups of secondary electrons in the multi-beam is expanded by a magnifying lens 367, and the secondary electrons are converted into a light by a scintillator 368 and further into an electric signal by a light guide 379 and a photomultiplier 369, which is used subsequently in a plurality of A/D converter, an image forming circuit to form a two-dimensional image. Further, the sample 366 is applied with a negative high voltage 378, and the primary beam is irradiated with a low landing energy on the order of 200 V.

FIG. 36 shows an arrangement of a plurality of the above-discussed optical systems along a straight line as is the case with FIG. 31.

Further, similarly to the example of FIG. 32, as to the E×B separator and/or the electrostatic deflectors, the lenses and the like, a plurality of apertures 372, 374 corresponding to optical axes is formed in a ceramic substrate 370 with metal coating applied in the periphery of the apertures and thus configured plates are fabricated by a desired number and further assembled by using knock pins 371 in the necessary Z-positions to provide a primary optical system defined from the electron gun 361 to the lowest pole of the objective lens 365. Further, as to the secondary optical system, since the optical axis extends obliquely in the opposite direction (in the front surface and the back surface of the paper) for any adjacent optical axes with respect to the optical axes of the primary optical system disposed along the straight line, and so the pitch between adjacent optical axes of the secondary optical system would have a double distance of that of the primary optical system, therefore the secondary optical system can be fabricated in a conventional lens structure.

According to the illustrated embodiment, since the emission angle and/or the crossover size of the beam from the electron gun is controlled by the lens including a plurality of anodes, a necessary lens may be simplified into a single stage lens and its associated aligning device is no more necessary, and accordingly the optical axis length can be also made shorter, thus facilitating the formation of the multi-beam with a simplified optical system.

SIXTEENTH EXAMPLE

Figure 37:
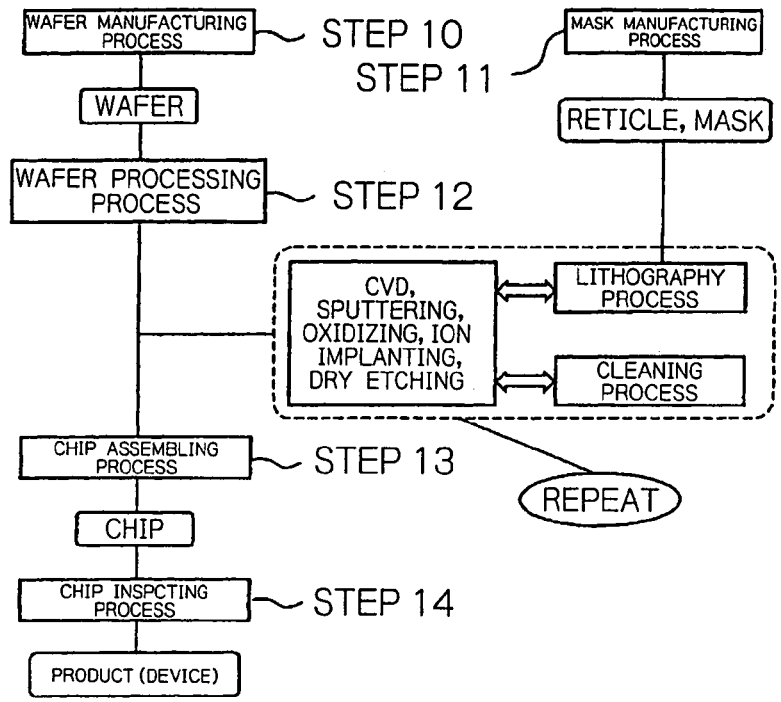
FIG. 37 is a flow chart showing a semiconductor device manufacturing process.

FIG. 37 shows a pattern evaluation method illustrated in the above embodiment applied to a wafer evaluation in a semiconductor device manufacturing process.

An example of a device manufacturing process will be described with reference to a flow chart of FIG. 37.

This manufacturing process includes the following main processes.

(1) A wafer manufacturing process for fabricating a wafer (or wafer preparing process for preparing a wafer) (Step 10)

(2) A mask manufacturing process for fabricating a mask to be used in the exposure (or a mask preparing process for preparing a mask) (Step 11)

(3) A wafer processing process for performing any processing treatments necessary for the wafer (Step 12)

(4) A chip assembling process for cutting out those chips formed on the wafer one by one to make them operative (Step 13)

(5) A chip inspection process for inspecting an assembled chip (Step 14)

It is to be noted that each of these main processes further comprises several sub-processes.

Among the main processes, one that has a critical effect on the performance of the semiconductor device is the wafer processing process. In this wafer processing process, the designed circuit patterns are deposited on the wafer one on another, thus to form many chips, which will function as memories or MPUs. This wafer processing process includes the following sub-processes.

(1) A thin film deposition process for forming a dielectric thin film to be used as an insulation layer, a metallic thin film to be formed into a wiring section or an electrode section, and the like (by using the CVD or the sputtering process)

(2) An oxidizing process for oxidizing thus formed thin film layers and the wafer substrate (3) A lithography process for forming a resist pattern by using a mask (reticle) in order to selectively process the thin film layers and/or the wafer substrate (4) An etching process for processing the thin film layers and/or the wafer substrate in accordance with the resist pattern (by using, for example, the dry etching technology)

(5) An ions/impurities implant and diffusion process (6) A resist stripping process (7) An inspection process for inspecting the processed wafer It is to be noted that the wafer processing process must be performed repeatedly as desired depending on the number of layers contained in the wafer, thus to manufacture a semiconductor device that will be able to operate as designed.

Figure 38:
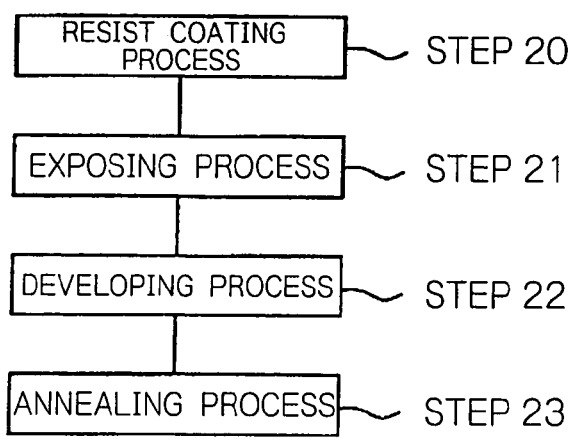
FIG. 38 is a flow chart showing a lithography process in the semiconductor device manufacturing process of FIG. 37.

FIG. 38 shows a flow chart showing the lithography process included as a core process in said wafer processing process. The lithography process comprises the respective processes as described below.

(1) A resist coating process for coating the wafer having a circuit pattern formed thereon in the preceding stage with the resist (Step 20)

(2) An exposing process for exposing the resist (Step 21)

(3) A developing process for developing the exposed resist to obtain the pattern of the resist (Step 22)

(4) An annealing process for stabilizing the developed resist pattern (Step 23)

A known process is applied to each of the semiconductor device manufacturing process, the wafer processing process and the lithography process described above.

When a pattern evaluation method according to the above-defined respective embodiments is used in the above-described inspection process of (7), any defects can be detected with high precision without any image disorders of the secondary electron image even on a semiconductor device having a fine pattern, enabling an improvement in yield of the products as well as the prevention of shipping of any defective products.

It is to be noted that the pattern evaluation according to the present invention is applicable to a broad range of pattern evaluation of a sample, including a defect inspection, a line width measurement, an aligning precision measurement, a potential contrast measurement for a sample such as a photo mask, a reticle, a wafer and so on.

Seventeenth Invention

An embodiment of an evaluation method of a resist pattern or a subsequently processed wafer according to the tenth invention will now be described with reference to FIGS. 39 to 42.

In the tenth invention, in order to evaluate a pattern formed on a wafer by using an electron beam direct writer or a pattern exposure system such as an excimer laser stepper, firstly such a wafer is prepared in which dies in an array defined by rows and columns on the wafer have been finished with the exposing and developing process with the dose and the focal condition modified in a two-dimensional matrix on the wafer by changing the dose in a step-by-step manner in the row direction and changing the focal condition in a step-by-step manner in the column direction.

Figure 39:
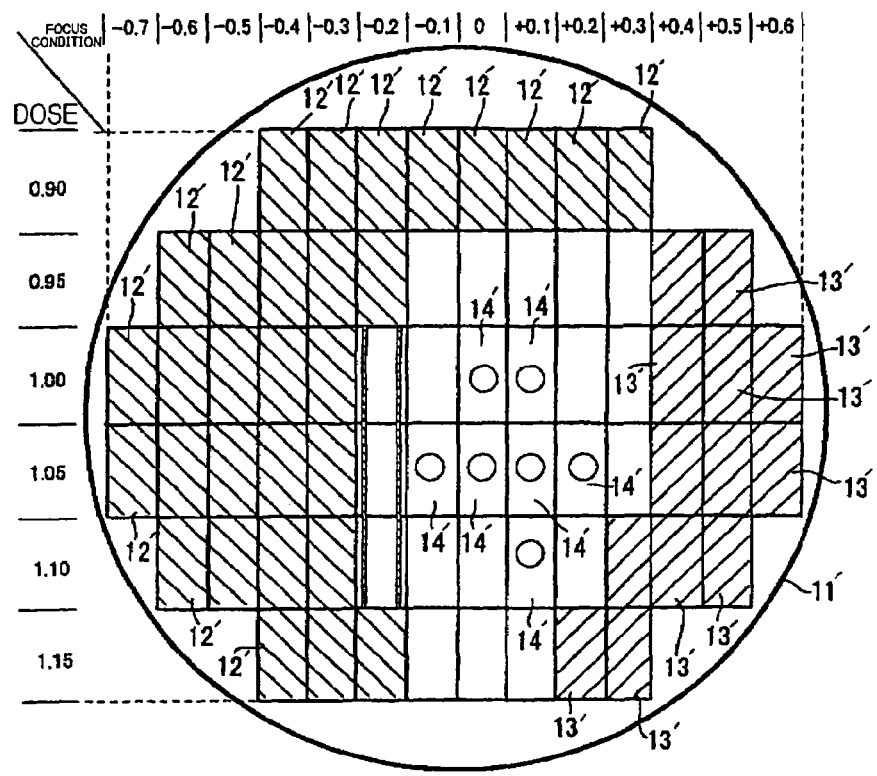
FIG. 39 is a diagram for illustrating an embodiment of an evaluation method of a resist pattern or a processed wafer according to a tenth invention.

That is, FIG. 39 shows an example of a 12-inch wafer created by the electron beam writer (not shown) with the dose and the focal condition that are changed in the two-dimensional matrix as discussed above. For example, the wafer 11' may contain a plurality of dies in a size of 20 mm×40 mm that have been formed by using the electron beam writer with the different dose in the row direction of 0.9, 0.95, 1.00, 1.05, 1.10, 1.15 ($\times 10^{-6}$ coulomb/cm$^2$) and the focal condition in the column direction changing from 0.7 μm over-focusing to 0.6 μm under-focusing by every 0.1 μm.

For example, each of the dies 12' positioned in the top row of the wafer 11' is associated with the dose of 0.90 ($\times 10^{-6}$ coulomb/cm$^2$), and the focal condition has been changed from the left die to the right die sequentially by changing the objective lens current within the range of −0.4 μm to +0.3 μm by every 0.1 μm. Similarly, each of the dies positioned in the second row from the top of the wafer 11' is associated with the dose of 0.95 ($\times 10^{-6}$ coulomb/cm$^2$), and the focal condition has been changed from the left die to the right die sequentially within the range of −0.6 μm to +0.5 μm by every 0.1 μm.

In thus prepared wafer 11', a CD measuring device measures a line width of each die at a predetermined position by a desired number per die. Specifically, after the wafer 11' has been exposed and developed, the measurement of the line width of a predetermined pattern of every die is performed at five positions in each die by the CDSEM. It is assumed that as a result, the hatched die 12' identified with the diagonal lines falling toward the right has the line width (the width of the exposed region) smaller than 90 nm, which should have been 100 nm in design size, and it is determined that the design specification has not been satisfied. It is further assumed that the hatched die 13' identified with the diagonal lines rising toward the right has the line width (the width of the exposed region) of 110 nm or greater, which should have been 100 nm in design size, and it is determined that the design specification has not been satisfied. It can be determined from the result that the not-hatched die is free from any failure measured in line width and worthy of application of the defect inspection. Such a die is then applied with the defect inspection to detect a defect as will be discussed below.

In evaluating a lithography margin, the proximity effect should be most critical in the vicinity of interface between a memory cell 22' and a peripheral pattern area 23'. The inspection of those regions with the electrons is efficient. In the present invention, since each die 21' has a central memory cell 22' and its adjacent peripheral pattern area 23', it is efficient that the interface region associated with the varied pattern density should be examined preferentially by a defect inspection apparatus. An elongated scanning area 24', 25' including said interface region is specified in opposite sides of the memory cell 22'. The scanning area 24', 25' is specified such that one-half of a single stripe is defined in the memory cell area 22' and the other half of the stripe is defined in the peripheral pattern area 23'.

Figure 40:
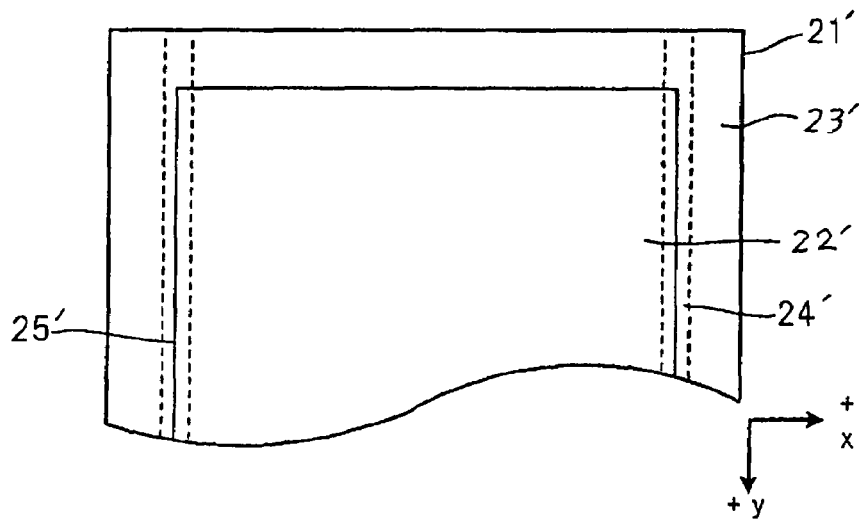
FIG. 40 is a diagram for illustrating a configuration of one die and an area having the priority in the inspection in FIG. 39.

In actual practice, for the defect inspection, each die 21' is divided into a plurality of stripes, which contains the scanning area 24', 25' and each having a width corresponding to the scanning area, and the scanning operation is carried out for each stripe. As shown in FIG. 40, assuming that in the scanning area 24', 25', a longitudinal direction is designated as y-direction and a direction orthogonal to the y-direction is designated as x-direction, in order to perform the defect inspection of the wafer 11', the defect inspection apparatus irradiates in the x-direction by a length corresponding to the width of one stripe with an electron beam of rectangular-shape in its sectional view, while moving the wafer 11' continuously in the y-direction, to thereby complete the scanning over one stripe, and then the apparatus performs the same procedure for the scanning over the adjacent stripe. These steps of procedure are repeated to complete the scanning operation across each scanning area 24', 25' so as to examine to see whether there is a defect.

Figure 41:
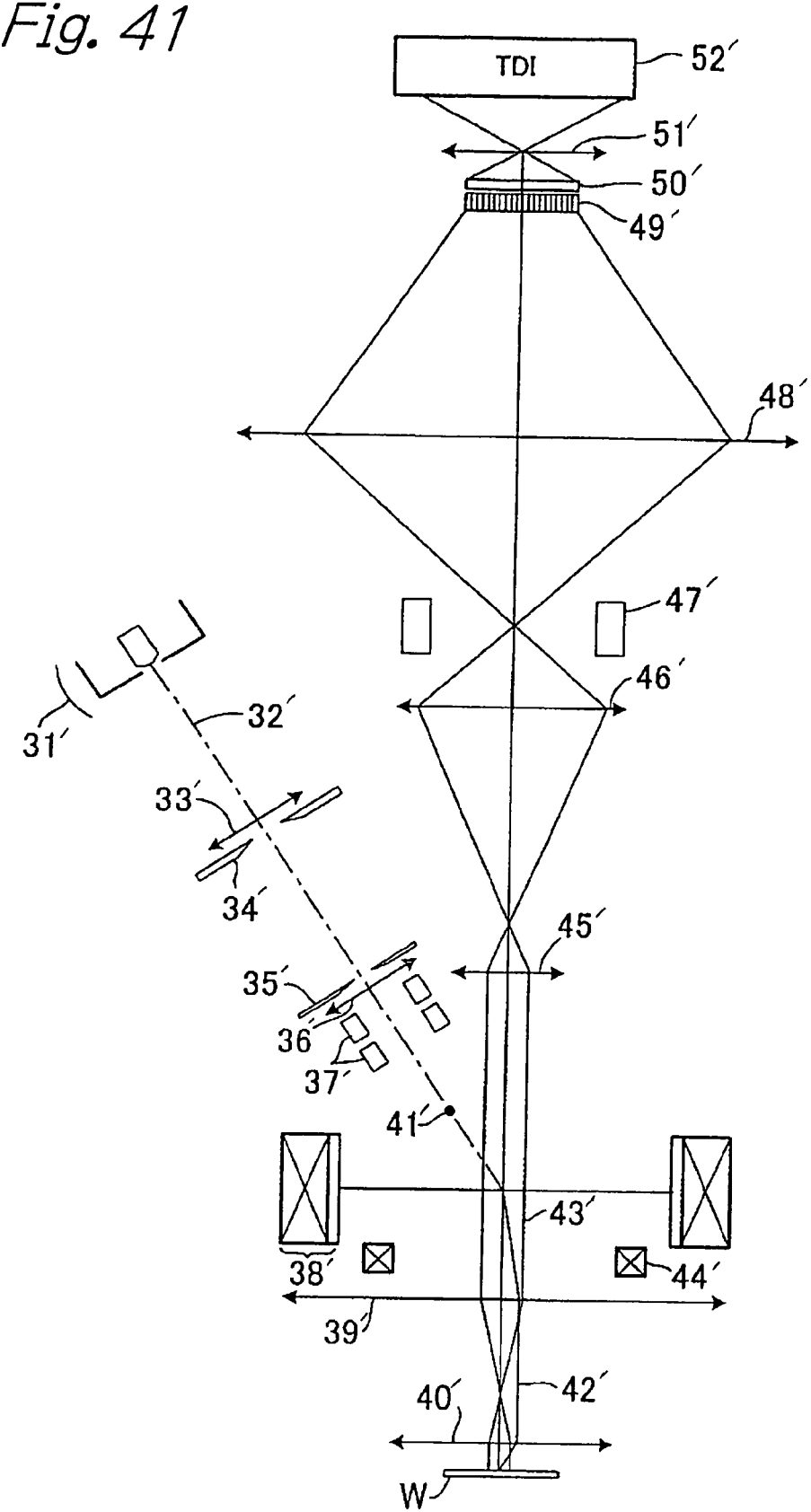
FIG. 41 is a diagram schematically showing an exemplary structure of a defect inspection apparatus applicable to an evaluation method of a resist pattern or a processed wafer according to the tenth invention.

FIG. 41 shows an exemplary structure of a defect inspection apparatus that can be used in an evaluation method of a resist pattern or a processed wafer according to the tenth invention for carrying out the above-described evaluation. A primary beam 32' emitted from an electron gun 31' having a cathode of LaB$_6$ is converged by a condenser lens 33' to form a crossover in an NA aperture 35'. During this step, any electron beams out of the field are removed by a beam shaping aperture 34' of rectangular shape disposed immediately below the condenser lens 33'. The primary beam 32' having passed through the condenser lens 33' forms a rectangular beam on a conjugate plane 41' for a wafer W provided by a doublet-type objective lens 39', 40'.

This rectangular beam is deflected by an E×B separator 38' toward the direction of normal line of the wafer W and focused by the objective lens 39', 40' on the surface of the wafer W. At this time, the trajectory 42' of the primary beam follows a different path away from the trajectory of a secondary beam 43', and so there would be no more fear that the blur of the secondary beam 43' is enhanced by the effect of the space charge pertaining to the primary beam 32'.

The primary beam 32' thus formed by the primary optical system may irradiate an area larger by about 10 μm than an area defined by 51.2 μm×25.6 μm, for example, on the surface of the wafer W. The primary beam 32' is driven by an electrostatic deflector 37' with eight-poles to perform a scanning operation in a direction orthogonal to the paper along a shorter side of the rectangle by a scanning width of 205 μm, for example, while at the same time, the table (not shown) carrying the wafer W thereon is moved continuously in the direction orthogonal to said scanning direction.

The wafer W is applied with a voltage of −4 kV. Accordingly, the secondary beam 43' emanating from the scanned wafer W is accelerated in the normal line direction of the wafer W and converged through the objective lens 40', 39' to form an enlarged image on the deflecting support point of the E×B separator 38'. Since the objective lens 39', 40' is designed in a configuration proximal to the symmetric doublet lens, the distortion and the magnification chromatic aberration has been reduced to be low. The secondary beam 43' passing through the E×B separator 38' without being deflected thereby is magnified by the magnifying lenses 45', 46' and 48' so as to form an enlarged image of the wafer W in front of an MCP (multi-channel plate) 49'.

In the illustrated secondary electronic optical system, in synchronism with the scanning operation of the primary beam 32', a correction is applied to the path of the secondary beam 43' by the deflector 44' so that the secondary beam 43' may pass through the vicinity of the center of the magnifying lens 45', and further a deflection correction is applied by the deflector 47' in order to reduce the aberration. Owing to this, since the aberration induced in the secondary beam 43' is limited almost to that caused by the initial two-stage of lenses 39', 40', the secondary electron optical system can be of low aberration.

After the number of electrons in each pixel of the secondary beam image has been multiplied by about $10^4$ by a MCP 49, the secondary beam 43' is converted to an image of light by a scintillator plate 50'. At this time, although an accelerating voltage is applied between the back surface of the MCP 49' and the scintillator plate 50', owing to a gap on the order of 500 μm provided between the back surface of the MCP 49' and a front surface of the scintillator plate 50', the secondary beam could be diverted over a range of 30μ in the front surface of the scintillator even when the secondary beam having the electron number distribution of delta function enters the front surface of the MCP 49. Accordingly, it is preferred that the magnification of the secondary electron optical system may be selectively set to such a magnification that the pixel of 100 nm, for example, on the surface of the wafer W can be magnified to 60 μm or more on the front surface of the scintillator plate 50', or magnified by a multiple of 600 or more.

The image of light formed in the scintillator plate 50' is focused by a relay lens 51' on a light acceptance surface of a TDI camera 52'. It is to be noted that a difference in size between a pixel in the TDI camera 52' and a pixel in the scintillator plate 50' can be compensated for by selecting the magnification of the relay lens 51' appropriately.

Figure 42:
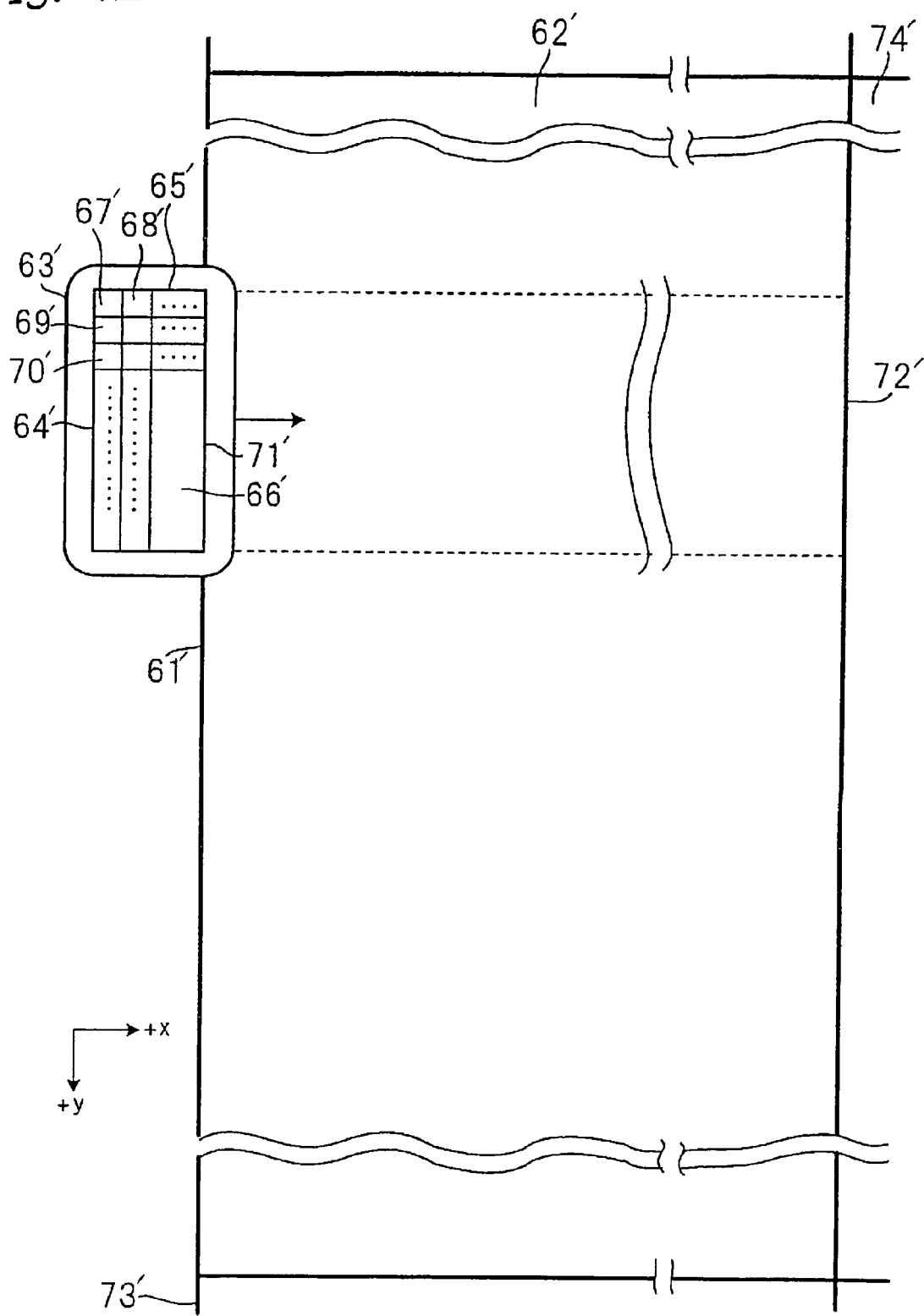
FIG. 42 is a diagram for illustrating a scanning operation performed by the defect inspection apparatus shown in FIG. 41.

Steps for carrying out a defect inspection of the wafer in accordance with an evaluation method of a resist pattern or a processed wafer according to the tenth invention will now be described with reference to FIG. 42. As already explained with respect to FIG. 40, the scanning operation for a single die 61' is carried out for each of the plurality of stripes 62' defining the width in the x-direction in a range of 100 μm to 200 μm. A sectional geometry 63' of the electron beam formed by the defect inspection apparatus shown in FIG. 41 is substantially rectangular on the surface of the wafer 11'. The primary electron beam has a sufficiently uniform intensity within a specific rectangular irradiation area 66' enclosed by the y-directional sides 64' and the x-directional sides 65' in the sectional geometry 63'. FIG. 42 indicates that said irradiation area 66' contains a plurality of pixels, 67', 68', 69', 70' . . . .

While moving the wafer 11' continuously in the +y direction, the defect inspection apparatus moves the electron beam in the +x direction from one end of a single stripe 62' by every pixel width until it reaches the other end, then the beam makes a flyback to the original one end. Specifically, when the side 71' positioned in the right-hand side of the irradiation area 66' in the diagram reaches the left end of the single stripe 62', the defect inspection apparatus starts the detection of the secondary electrons. When the electron beam has traveled from this starting point toward the right by one pixel width on the stripe, meaning that the irradiation area 66' has been transferred by one pixel width, the secondary electron signal indicative of the secondary electrons detected from the pixel falling in the irradiation area 66' among those pixels aligned in the y-direction at the left-most side of the stripe 62' is input to the first pixel column of the TDI camera 52' (FIG. 41).

When the electron beam has been advanced across the stripe 62' toward the right further by one pixel width, the secondary electron signal held in the first pixel column of the TDI camera 52' is transferred to the left, so that the secondary electron signal indicative of the secondary electrons detected from the pixel falling in the irradiation area 66' among those pixels aligned in the y-direction at the left-most side of the stripe 62' is input to the first pixel column, and the secondary electron signal indicative of the secondary electrons detected from the pixel falling in the irradiation area 66' among those pixels aligned in the y-direction at the second from the left of the stripe 62' is input to the second pixel column.

In this way, each time the electron beam is shifted across the stripe 62' toward the right by the width corresponding to one pixel, the secondary electron signal from the pixel falling in the irradiation area 66' among those pixels aligned in the y-direction at the left-most side of the stripe 62' is transferred to the left and accumulated in the TDI camera 52'. Finally, when the side 64' positioned in the left end of the rectangle 66' has passed the pixel aligned in the y-direction at the left-most side of the stripe 62', the pixel of the TDI camera 52' outputs a signal corresponding to the secondary electron signal from the pixel aligned at the left-most side of the stripe 62'.

A similar operation is repeated and when the side 64' positioned at the left side of the irradiation area 66' has passed the right end 72' of the stripe 62', the secondary electron signal from a pixel falling in the irradiation area 66' among the pixels aligned in the y-direction at the right-most side of the stripe 62' is output and thus a one-cycle of the x-directional scanning operation has been completed. When the one-cycle of scanning operation has been completed, the defect inspection apparatus makes a flyback of the electron beam to the left end of the stripe 62'. Since the stage is continuously moving in the y-direction, the die 61' has been moved in the +y direction by a distance corresponding to the length of the side 64'. After that, a scanning operation similar to that discussed above is commenced.

Actually, since the wafer 11' and thus the die 61' is moved continuously in the +y direction in the duration of each scanning operation, the electron beam 61' will be driven also in the −y direction so as to compensate for the moving rate in the +y direction of the die 61'. However, since the sectional geometry 63' of the electron beam has a certain size of irradiation area 66' sufficient to cover a specified number of pixels arranged in the vertical and horizontal directions with some margin, it is not necessary to perform the scanning of extra high precision. If the vibration of the wafer 11' or the uneven rate of moving speed of the wafer 11' in the y-direction is detected, a positional correction is made in the secondary electron optical system so that the position to be measured on the stripe can be formed into an image correctly on the MCP 49'.

In FIG. 42, when the scanning of one die 61' has been completed, subsequently the scanning is applied to a die 73' adjacent to the die 61' in the y-direction, and in this way when the scanning has been completed across one stripe 62' to the die at the end of the wafer 11' in the +y direction, then the defect inspection apparatus performs the scanning operation across a stripe 74' adjacent to the stripe 62', while moving the wafer 11' in the −y direction mechanically.

The defect inspection apparatus determines whether thus detected defect is resultant from the lithography or other types of defect, such as those from particle or the like, and in accordance with the determination, eliminates those defects having no connection with the lithography condition, such as the defect from particle, but picks up exclusively the defects having a connection with the lithography, such as abnormal pattern from the excessive or insufficient compensation for the proximity effect, wherein the distribution of the defect generation resultant from the lithography is examined to evaluate the lithography margin. As a result, the die 14' indicated with a circle mark in FIG. 39 represents the die containing no defect resultant from the lithography.

In this case, it can be concluded from the evaluation as described above that the lithography margin is in a range of 0.1 μm over-focusing to 0.2 μm under-focusing, and the dose is in a range of 1.0 μc/m$^2$ to 1.10 μc/m$^2$.

The evaluation method of a resist pattern or a processed wafer according to the tenth invention can be effectively applied to a semiconductor device manufacturing method shown in FIG. 37 and FIG. 38, for example.

If the evaluation method of a resist pattern according to the tenth invention is used in the chip inspection process in the sixteenth example to carry out the defect inspection, any defects can be detected with high throughput even on a semiconductor device having a fine pattern, enabling not only the 100 percent inspection but also the improvement in yield of the products as well as the prevention of shipping of any defective products.

As can be understood from the above description, since the use of the electron beam can achieve the resolution of 0.1 μm or lower over the resolution of 0.1 μm or higher obtainable by the light, the present invention can bring about a particularly advantageous effect that the lithography margin can be measured with a high resolution over the defect inspection of optical method of the prior art. Since in the present invention, the defect inspection is not applied to every single die but only to the die having a normal line width, the time required for the defect inspection can be shortened.

What is claimed is:

1. An electron beam apparatus comprising:
    an electron gun comprising a cathode for emitting a primary electron beam to a sample,
    a double lens for focusing said primary beam, and
    a detecting unit for detecting secondary electrons or back scattering electrons emanated from said sample,
    wherein said electron gun has a ring configuration for emitting a primary electron as a hollow beam and passing an outer side of said secondary electrons or back scattering electrons.

2. An electron beam apparatus in accordance with claim 1, further comprising a Wehnelt and an anode for controlling said hollow beam, and
    said cathode emits a primary electron beam when being subject to light irradiation or heating,
    said anode has an inner anode and an outer anode, said inner anode disposed on an inside with respect to said cathode and said outer anode disposed on an outside with respect to said cathode,
    wherein said inner anode and said outer anode are insulated from each other and an emission angle of said hollow beam is adjusted by changing a potential of said inner anode or said outer anode.

3. An electron beam apparatus in accordance with claim 1, further comprising a NA aperture for eliminating said secondary electrons or back scattering electrons at a predetermined angle relative to a normal line of said sample.

\* \* \* \* \*